(12) United States Patent
Liebeschuetz et al.

(10) Patent No.: US 6,946,467 B2
(45) Date of Patent: Sep. 20, 2005

(54) SERINE PROTEASE INHIBITORS

(75) Inventors: John Walter Liebeschuetz, Bollington (GB); Christopher William Murray, Swavesey (GB); Stephen Clinton Young, Heaton Moor (GB); Nicholas Paul Camp, Bracknell (GB); Stuart Donald Jones, Macclesfield (GB); William Alexander Wylie, Carrickfergus (GB); John Joseph Masters, Fishers, IN (US); Michael Robert Wiley, Indianapolis, IN (US); Scott Martin Sheehan, Carmel, IN (US); David Birenbaum Engel, Bloomington, IN (US); Brian Morgan Watson, Carmel, IN (US); Peter Robert Guzzo, Niskayuna, NY (US); Michael John Mayer, Guiderland, NY (US)

(73) Assignee: Eli Lilly and Company, Indianapolis, IN (US)

( * ) Notice: Subject to any disclaimer, the term of this patent is extended or adjusted under 35 U.S.C. 154(b) by 351 days.

(21) Appl. No.: 10/030,187

(22) PCT Filed: Dec. 6, 2001

(86) PCT No.: PCT/GB01/02553

§ 371 (c)(1),
(2), (4) Date: Feb. 4, 2002

(87) PCT Pub. No.: WO01/96323

PCT Pub. Date: Dec. 20, 2001

(65) Prior Publication Data

US 2003/0055246 A1 Mar. 20, 2003

(30) Foreign Application Priority Data

Jun. 13, 2000 (GB) .............................. PCT/GB00/02302
Dec. 13, 2000 (GB) .............................................. 0030304

(51) Int. Cl.[7] ................... C07D 401/14; A61K 31/496; A61P 7/02

(52) U.S. Cl. ................................. 514/253.09; 544/364

(58) Field of Search ..................... 546/364; 514/253.09

(56) References Cited

U.S. PATENT DOCUMENTS 5,346,907 A      9/1994   Kerwin et al. ............... 514/312

FOREIGN PATENT DOCUMENTS

| EP | 796866 A1 | 9/1997 |
|---|---|---|
| WO | WO 91/00725 | 1/1991 |
| WO | WO 97/49404 | 12/1997 |
| WO | WO 98/47876 | 10/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/11657 | 3/1999 |
| WO | WO 99/11658 | 3/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 00/71493 | 11/2000 |
| WO | WO 00/71507 | 11/2000 |
| WO | WO 00/71508 | 11/2000 |
| WO | WO 00/76971 | 12/2000 |
| WO | WO 00/76970 | 12/2002 |
| WO | WO 00/77027 | 12/2002 |

OTHER PUBLICATIONS

Jones, Stuart D, et al., Bioorganic & Medicinal Chemistry Letters 11 (2001) 733–736.

*Primary Examiner*—Mark L. Berch
*Assistant Examiner*—Kahsay Habte
(74) *Attorney, Agent, or Firm*—Martin A Hay

(57) ABSTRACT

The compound 1-(indole-6-carbonyl-D-phenylglycinyl)-4-(1-methylpiperidin-4-yl)piperazine and physiologically-tolerable salts thereof are factor Xa inhibitors useful for the treatment of thrombotic disorders.

4 Claims, No Drawings

SERINE PROTEASE INHIBITORS

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, aematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of al protease inhibitor deficiency with emphysema and cirrhosis and Cl esterase inhibitor deficiency with angioedema.

It has now been found that certain aromatic compounds carrying bulky lipophilic side chains are particularly effective as inhibitors of serine proteases, especially proteases with negatively charged Pi specificity pockets, and most especially the serine proteases thrombin, and most importantly Factor Xa. The Factor Xa inhibitors of this invention are potentially useful for the prophylaxis or treatment of thrombotic disorders such as amongst others venous thrombosis, pulmonary embolism, arterial thrombosis, myocardial ischaemia, myocardial infarction, and cerebral thrombosis. They potentially have benefit in the treatment of acute vessel closure associated with thrombolytic-therapy and restenosis, e.g. after transluminal coronary angioplasty or bypass grafting of the coronary or peripheral arteries and in the maintenance of vascular access patency in long term hemodialysis patients.

Factor Xa inhibitors of this invention may, with benefit, form part of a combination therapy with an anticoagulant with a different mode of action or with a thrombolytic agent.

It has been reported in WO99/11658 and WO99/11657 that certain benzamidine and aminoisoquinoline derivatives carrying a bulky lipophilic side chain are excellent inhibitors of serine proteases. Unfortunately, it has since been found that benzamidine compounds of WO 99/11658 in general demonstrate poor oral bioavailability.

Surprisingly, it has now been found that certain other aromatic compounds also show inhibitory activity against serine proteases, in particular Factor Xa, despite the lack of the amidino or 1-aminoisoquinoline functionality previously believed to be crucial for activity as a factor Xa inhibitor. Many of these compounds also possess other structural features that further distinguish them from the compounds of WO99/11658 and WO99/11657.

Where compounds of the invention have been tested, they have generally demonstrated superior oral bioavailability in comparison with benzamidines disclosed in WO 99/11658. Also, it has been found that the compounds of the invention perform excellently in the prothrombin time assay (PT) when compared to aminoisoquinolines of similar factor Xa activity and structure. The PT assay is a coagulation assay and it is widely accepted that direct acting Factor Xa inhibitors which perform well in the PT assay are more likely to be good antithrombotics.

In WO99/09053 certain 2-aminobenzamide compounds are disclosed as potential motilin receptor antagonists and in U.S. Pat. No. 3,268,513 similar 2-aminobenzamide compounds are suggested as potential antibacterial agents. However, the novel compounds of the present invention have not before been suggested as potential serine protease inhibitors.

Thus viewed from one aspect the invention provides a serine protease inhibitor compound of formula (I)

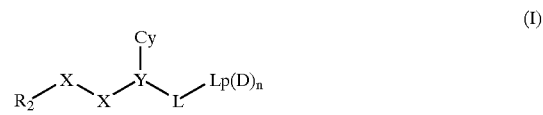

(I)

wherein:
R$_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or R$_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or R$_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that R$_2$ cannot be aminoisoquinolyl;

each X independently is a C, N, O or S atom or a CO, CR$_{1a}$, C(R$_{1a}$)$_2$ or NR$_{1a}$ group, at least one X being C, CO, CR$_{1a}$ or C(R$_{1a}$)$_2$;

each R$_{1a}$ independently represents hydrogen or hydroxyl, alkoxy, alkyl, aminoalkyl, hydroxyalkyl alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or $R_{3i}X_i$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkylthiazolyl, alkyloxazolyl, oxazolyl, alkylsulphonamido, alkylaminosulphonyl, aminosulphonyl, haloalkoxy, haloalkyl, a group of the formula —C($X^3$)N($R^{11}$)$R^{12}$ (wherein $X^3$ is O or S; and $R^{11}$ and $R^{12}$ are independently selected from hydrogen, methyl or ethyl or together with the nitrogen atom to which they are attached form a pyrrolidin-1-yl, piperidin-1-yl or morpholino group), or —OCH$_2$O— which is bonded to two adjacent ring atoms in Cy;

$X_i$ is a bond, O, NH or CH$_2$;

$R_{3i}$ is phenyl, pyridyl or pyrimidinyl optionally substituted by $R_{3a}$;

$R_{1b}$, $R_{1c}$ and $R_{1j}$ are as defined for $R_{1a}$; and

—L—Lp(D)n is of the formula:

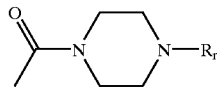

in which $R_r$ is —(CH$_2$)$_c$—$R_c$, —CHR$_e$R$_f$, CH$_2$—CHR$_e$R$_f$, —CH$_2$—CH$_2$—CHR$_e$R$_f$ or $R_g$ in which c is 1 or 2; $R_c$ is thienyl, thiazolyl (which may bear an amino substituent), isothiazolyl, oxazolyl, isoxazolyl, pyrazolyl, imidazolyl, pyridyl (which may bear an alkylsulphonyl, aminosulphonyl, alkylaminosulphonyl, alkylaminocarbonyl, amino, amido, (1–4C)alkoxycarbonyl, carboxy, acetylamino, chloro, fluoro, cyano, (1–3C)alkyl, trifluoromethyl, methoxy, ethoxy, nitro, hydroxy, alkylsulphonylamino, triazolyl or tetrazolyl substituent), pyrimidinyl, pyridazinyl, pyrazinyl or phenyl (which may bear a methyl, methylamino, dimethylamino, carboxy, dialkylaminosulphonyl, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl or tetrazolyl substituent); each of $R_e$ and $R_f$ independently is hydrogen or C$_{1-3}$alkyl; or CHR$_e$R$_f$ is cyclopentyl (which may bear a hydroxy, amino, (1–3C)alkoxy, (1–3C)hydroxyalkyl, (1–3C)alkyl, carboxy, methoxycarbonyl or ethoxycarbonyl substituent at the 3- or 4-position), cyclohexyl (which may bear a hydroxy, amino, (1–3C)alkoxy, (1–3C)hydroxyalkyl, (1–3C)alkyl, carboxy, methoxycarbonyl or ethoxycarbonyl substituent at the 3- or 4-position), tetrahydropyran-4-yl, tetrahydrothiopyran-4-yl, pyrrolidin-3-yl (which may bear a hydroxy, amino, (1–3C)alkoxy, (1–3C)hydroxyalkyl, (1–3C)alkyl, carboxy, methoxycarbonyl or ethoxycarbonyl substituent at the 1-position), piperidin-4-yl (which may bear a hydroxy, amino, (1–3C) alkoxy, (1–3C)hydroxyalkyl, (1–3C)alkyl, carboxy, methoxycarbonyl or ethoxycarbonyl substituent at the 1-position), or indan-2-yl; and $R_g$ is 2-methylsulphonylphenyl which may bear a 4-fluoro substituent or $R_g$ is $\lambda^6$-1,1-dioxobenzo[b]thiophen-7-yl;

or a physiologically-tolerable salt thereof (e.g. a halide, phosphate or sulfate salt or a salt with ammonium or an organic amine such as ethylamine or meglumine); provided that Lp(D)n is not of the formula (K):

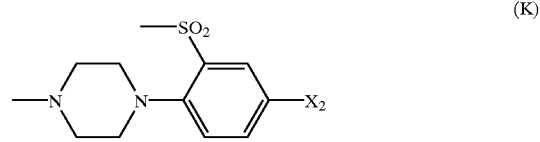

wherein $X_2$ is fluoro or hydrogen.

In another aspect the invention relates to a serine protease inhibitor compound of formula (I)

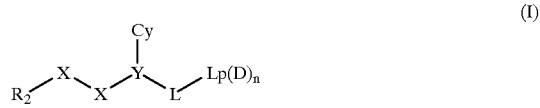

wherein:

$R_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or $R_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independently is a C, N, O or S atom or a CO, $CR_{1a}$, C($R_{1a}$)$_2$ or NR$_{1a}$ group, at least one X being C, CO, $CR_{1a}$ or C($R_{1a}$)$_2$;

each $R_{1a}$ independently represents hydrogen or hydroxyl, alkoxy, alkyl, aminoalkyl, hydroxyalkyl alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R^1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkyl imidazolyl, thiazolyl, alkyl thiazolyl, alkyl oxazolyl, oxazolyl, alkylsulphonamido, alkylaminosulphonyl, aminosulphonyl, haloalkoxy and haloalkyl;

$R_{1b}$, $R_{1c}$ and $R_{1j}$ are as defined for $R_{1a}$; and —L—Lp(D)$_n$ is of the formula:

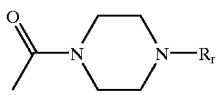

in which $R_r$ is —(CH$_2$)$_c$—$R_c$, —CHR$_e$R$_f$, —CH$_2$—CHR$_e$R$_f$, or $R_g$ in which c is 1 or 2; $R_c$ is pyridyl or phenyl (which phenyl may bear a fluoro, chloro, methyl, CONH$_2$, SO$_2$NH$_2$, methylaminosulphonyl, dimethylaminosulphonyl, methoxy or methylsulfonyl substituent); each of $R_e$ and $R_f$ independently is hydrogen or C$_{1-3}$alkyl; or CHR$_e$R$_f$ is cyclopentyl (which may bear a methyl, ethyl or hydroxymethyl substituent at the 3- or 4-position), cyclohexyl (which may bear a methyl, ethyl or hydroxymethyl substituent at the 3- or 4-position), tetrahydropyran-4-yl, tetrahydrothiopyran-4-yl, pyrrolidin-3-yl (which may bear a 1-methyl substituent), piperidin-4-yl (which may bear a 1-methyl substituent), or indan-2-yl; and $R_g$ is 2-methylsulphonylphenyl which may bear a 4-fluoro substituent or $R_g$ is $\lambda^6$–1,1-dioxobenzo[b]thiophen-7-yl;

or a physiologically-tolerable salt thereof; provided that Lp(D)n is not of the formula (K):

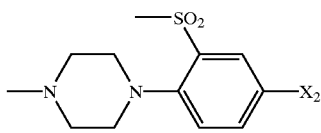

(K)

wherein X$_2$ is fluoro or hydrogen.

In the compounds of the invention, where the alpha atom is carbon it preferably has the conformation that would result from construction from a D-α-aminoacid NH$_2$—CR$_{1b}$(Cy)—COOH where the NH$_2$ represents part of X—X. Likewise the fourth substituent R$_{1b}$ at an alpha carbon is preferably a methyl or hydroxymethyl group or hydrogen. It will be appreciated that the compounds of formula (I) may exist in racemic or chiral form, and that the preferred D-isomer may be administered in a racemic mixture with the L-isomer, or alone.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. C$_{1-6}$ or C$_{1-3}$; cyclic groups preferably have ring sizes of 3 to 8 atoms; and fused multicyclic groups preferably contain 8 to 16 ring atoms.

Examples of particular values for R$_{1a}$ are: hydrogen, methyl or ethyl. R$_{1a}$ is preferably a hydrogen atom.

The linker group (X—X) from the R$_2$ group to the alpha atom is preferably selected from —CH=CH—, —CONH—, —CONR$_{1a}$—, —NH—CO—, —NH—CH$_2$—, —CH$_2$—NH—, —CH$_2$O—, —OCH$_2$—, —COO—, —OC=O— and —CH$_2$CH$_2$—. Preferably, the X moiety nearest to the alpha atom is an NH or O atom, most preferably a NH group. The X moiety alpha to the aromatic ring is preferably a carbon based group such as CH$_2$ or CO, preferably CO. Thus a particularly preferred linker X—X is —CONH—. In an alternative embodiment the linker is a —OCH$_2$— group.

Examples of particular values for R$_{1b}$ are: hydrogen, (1–4C)alkyl, such as methyl or hydroxy(1–4C)alkyl, such as hydroxymethyl. R$_{1b}$ is preferably a hydrogen atom.

The alpha atom (Y) is preferably a CH or C(CH$_3$) group specially the alpha atom (Y) is CH.

Examples of particular values for —CHR$_e$R$_f$ in a —CHR$_e$R$_f$, —CH$_2$—CHR$_e$R$_f$ or —CH$_2$—CH$_2$—CHR$_e$R$_f$ group are 2-propyl, 3-pentyl, cyclopentyl, cyclohexyl, 4-methylcyclohexyl, tetrahydrothiopyran-4-yl, pyrrolidin-3-yl, 1-methylpyrrolidin-3-yl, 1-(2-propyl)pyrrolidin-3-yl, piperidin-4-yl, 1-methylpiperidin-4-yl, 1-(2-propyl)piperidin-4-yl and indan-2-yl.

When R$_r$ is of the formula —CHR$_e$R$_f$ a preferred value for R$_r$ is 1-methylpiperidin-4-yl.

Preferably R$_r$ is of the formula —(CH$_2$)$_c$—R$_c$.

Preferably c is 2.

Preferably —L—Lp(D)$_n$ is of the formula:

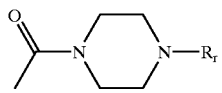

in which R$_r$ is —(CH$_2$)$_c$—R$_c$; in which c is 2; R$_c$ is thienyl, thiazolyl (which may bear an amino substituent), isothiazolyl, oxazolyl, isoxazolyl, pyrazolyl, imidazolyl, pyridyl (which may bear an amino, methoxycarbonyl, carboxy, fluoro, cyano, methyl, methylsulphonyl, aminosulphonyl, methylaminosulphonyl or dimethylaminosulphonyl or trifluoromethyl substituent), pyrimidinyl, pyridazinyl, pyrazinyl or phenyl (which phenyl may bear a fluoro, chloro, cyano, methyl, amino, methylsulphonyl, aminosulphonyl, methyl aminosulphonyl, dimethylaminosulphonyl, methyl amino, dimethylamino, carboxy, methoxycarbonyl or methoxy substituent)

Preferably, Rc is thiazolyl, (which may bear an amino substituent), pyrazolyl, imidazolyl, pyridyl (which may bear a methylsulphonyl, aminosulphonyl, methylaminosuliphonyl, dimethylaminosulphonyl, fluoro, cyano, methyl or trifluoromethyl substituent), pyrimidinyl, pyridazinyl, pyrazinyl or phenyl (which phenyl may bear a fluoro, chloro, cyano, methyl, amino, methylamino, dimethylamino, carboxy, methoxycarbonyl, methylsulphonyl, aminosulphonyl, methylaminosulphonyl, dimethylaminosulphonyl or methoxy substituent).

More preferably, Rc is thiazolyl (which may bear an amino substituent), pyrazolyl, imidazolyl, pyridyl (which may bear a fluoro, cyano, methyl or trifluoromethyl substituent), pyridazinyl or pyrazinyl.

Yet more preferably Rc is thiazol-2-yl, 2-aminothiazol-4-yl, pyrazol-1-yl, pyrazol-4-yl, pyridazin-3-yl, imidazol-1-yl, imidazol-4-yl, pyrazin-2-yl, pyrid-2-yl, pyrid-3-yl, pyrid-4-yl, 3-fluoropyrid-4-yl, 2-cyanopyrid-4-yl, 2-methylpyrid-4-yl or 2-trifluoromethylpyrid-6-yl.

Yet more preferably, R$_c$ is pyrazolyl, imidazolyl, pyridyl, pyridazinyl or pyrazinyl.

Preferably R$_c$ is pyrid-2-yl, pyrid-3-yl or pyrid-4-yl.

Most preferably, L is CO and the lipophilic group —Lp(D)n is selected from the formulae:

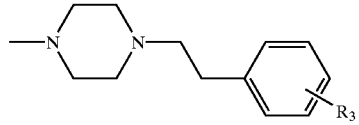

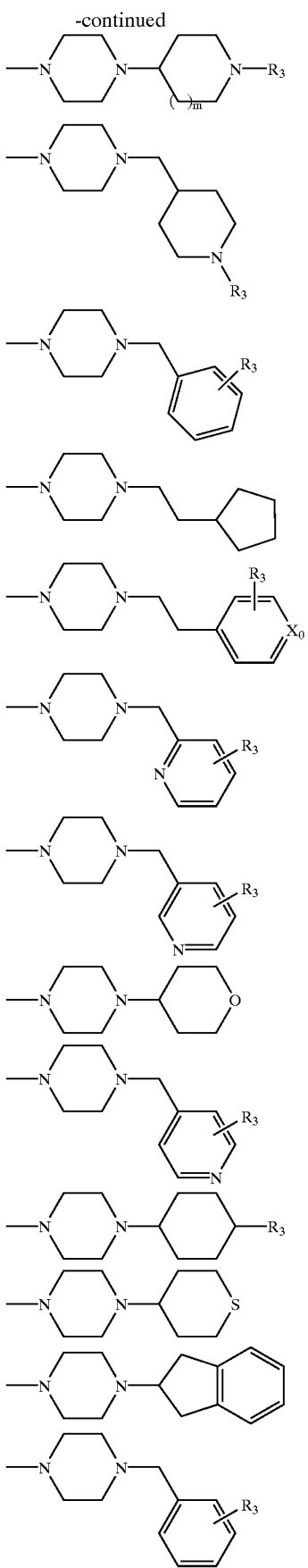

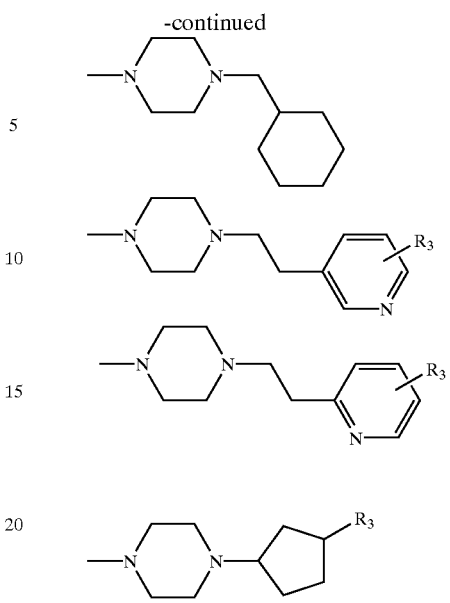

wherein;
    m represents 0 or 1;
    $X^0$ represents CH or N; and
    $R_3$ is as defined for $R_{3a}$.
    Preferably m is 1.
    Examples of particular values for $R_3$ are:
    hydrogen;
    hydroxyl;
    for alkoxy: methoxy or ethoxy;
    for alkyl optionally substituted by hydroxy, alkylamino, alkoxy, oxo, aryl or cycloalkyl: (1–6C)alkyl, such as methyl, ethyl, propyl, 2-propyl, butyl, 2-butyl, t-butyl, pentyl, 2-pentyl or 3- pentyl, (1–6C)alkylamino(1–6C)alkyl, such as isopropylaminomethyl, dimethylaminomethyl, diethylaminomethyl or dimethylaminoethyl, or (1–6C)alkanoyl, such as acetyl;
    for hydroxyalkyl optionally substituted by hydroxy, alkylamino, alkoxy, oxo, aryl or cycloalkyl: (1–6C) hydroxyalkyl, such as hydroxymethyl or hydroxyethyl, carboxy or carboxy(1–5C)alkyl; for alkoxyalkyl: methoxymethyl; for alkoxycarbonyl: methoxycarbonyl or ethoxycarbonyl: for alkylaminocarbonyl: methylaminocarbonyl or dimethylaminocarbonyl;
    for aminoalkyl optionally substituted by hydroxy, alkylamino, alkoxy, oxo, aryl or cycloalkyl: aminomethyl, aminocarbonyl or aminocarbonyl(1–5C)alkyl;
    for alkylamino optionally substituted by hydroxy, alkylamino, alkoxy, oxo, aryl or cycloalkyl: methylamino, dimethylamino, ethylamino, formylamino or acetylamino; amino;
    for halo: fluoro or chloro;
    cyano;
    nitro;
    thiol;
    for alkylthio: methylthio;
    for alkylsulphonyl: methylsulphonyl, ethylsulphonyl or isopropylsulphonyl;
    for alkylsulphenyl: methylsulphenyl ($CH_3SO$);
    for triazolyl: 1,2,4-triazol-2-yl, 1,2,4-triazol-4-yl or 1,2,3-triazol-4-yl;
    for imidazolyl: 1,3-imidazol-1-yl or 1,3-imidazol-4-yl;
    for tetrazolyl: tetrazol-1-yl or tetrazol-5-yl; for alkylsulphonamido: methylsulphonamido, ethylsulphonamido or propylsulphonamido;

for alkylaminosulphonyl: methylaminosulphonyl, ethylaminosulphonyl or propylaminosulphonyl; aminosulphonyl;
for haloalkoxy: trifluoromethoxy; and
for haloalkyl: trifluoromethyl or trichloromethyl.

When $R_3$ is present as a substituent on an aromatic ring, it is preferably selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl and tetrazolyl.

When $R_3$ is present as a substituent on a saturated ring, it is preferably selected from hydrogen, hydroxy, amino, (1–3C)alkoxy, (1–3C)hydroxyalkyl, (1–3C)alkyl, carboxy, methoxycarbonyl and ethoxycarbonyl.

For example specific Lp(D)n groups include

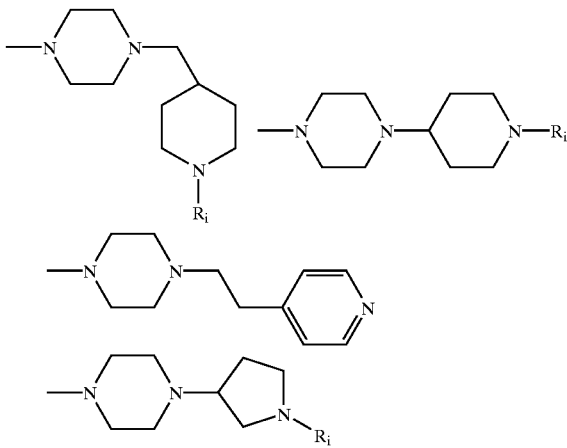

wherein $R_i$ is hydrogen or (1–6C)alkyl.
Preferably Ri is hydrogen, methyl or ethyl.
More preferably Ri is hydrogen or methyl.

The cyclic group (Cy) attached to the alpha carbon is preferably an optionally $R_{3a}$ substituted: phenyl, pyridyl, thienyl, thiazolyl, naphthyl, piperidinyl, furanyl, pyrrolyl, isoxazolyl, isothiazolyl, pyrazolyl, oxazolyl, imidazolyl, 1,2,4-thiadiazolyl, 1,3,4-thiadiazolyl, pyrimidinyl, pyridazinyl, quinolyl, isoquinolyl, benzofuryl, benzothienyl or cycloalkyl group, or a phenyl group substituted by $R_{3i}X_i$ in which $X_i$ is a bond, O, NH or $CH_2$ and $R_{3i}$ is phenyl, pyridyl or pyrimidyl group optionally substituted by $R_{3a}$.

The cyclic group (Cy) attached to the alpha carbon is more preferably an optionally $R_{3a}$ substituted phenyl, pyridyl (such as pyrid-2-yl, pyrid-3-yl or pyrid-4-yl), thienyl (such as thien-2-yl or thien-3-yl), thiazolyl (such as thiazol-2-yl, thiazol-4-yl or thiazol-5-yl), naphthyl (such as naphth-1-yl), piperidinyl (such as piperidin-4-yl) or cycloalkyl, such as a cyclohexyl group.

Examples of particular values for $R_{3a}$ are:
hydrogen;
hydroxyl;
for alkoxy optionally substituted by hydroxy, alkylamino, alkoxy, oxo, aryl or cycloalkyl: alkoxy, such as methoxy or ethoxy, or aralkyloxy, such as benzyloxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl optionally substituted by hydroxy, alkylamino, alkoxy, oxo, aryl or cycloalkyl: hydroxymethyl or carboxy;
for alkoxyalkyl: methoxymethyl;
for alkoxycarbonyl: methoxycarbonyl or ethoxycarbonyl;
for alkylaminocarbonyl: methylaminocarbonyl or dimethylaminocarbonyl;
for aminoalkyl optionally substituted by hydroxy, alkylamino, alkoxy, oxo, aryl or cycloalkyl: aminomethyl, $CONH_2$ or $CH_2CONH_2$;
for alkylamino optionally substituted by hydroxy, alkylamino, alkoxy, oxo, aryl or cycloalkyl: (1–6C)alkanoylamino, such as acetylamino;
for alkoxycarbonylamino: methoxycarbonylaminno, ethoxycarbonylamino or t-butoxycarbonylamino; amino;
for halo: fluoro or chloro;
cyano;
nitro;
thiol;
for alkylthio: methylthio;
for alkylsulphonyl: methylsulphonyl or ethylsulphonyl;
for alkylsulphenyl: methylsulphenyl;
for alkylsulphonamido: methylsulphonylamido or ethylsulphonylamido;
for alkylaminosulphonyl: methylaminosulphonyl or ethylaminosulphonyl;
aminosulphonyl;
for haloalkoxy: trifluoromethoxy;
for haloalkyl: trifluoromethyl;
for a group of the formula —$C(X^3)N(R^{11})R^{12}$ (wherein $X^3$ is O or S and $R^{11}$ and $R^{12}$ are independently selected from hydrogen, methyl, ethyl, or together with the nitrogen atom to which they are attached form a pyrrolidin-1-yl, piperidin-1-yl or morpholino group: —$CONH_2$, —CHNHMe, —$CON(Me)_2$, —$C(S)N_2$ —C(S)NHMe, —$C(S)N(Me)_2$, pyrrolidin-1-ylcarbonylpiperidin-1-ylcarbonyl or morpholinocarbonyl; and —$OCH_2O$— which is bonded to two adjacent ring atoms in Cy.

In another aspect $R_{3a}$ is selected from hydrogen, hydroxyl, alkoxy, alkyl (optionally substituted by hydroxy, alkylamino, alkoxy, oxo, aryl or cycloalkyl), hydroxyalkyl (optionally substituted by hydroxy, alkylamino, alkoxy, oxo, aryl or cycloalkyl), alkoxyalkyl, alkoxycarbonyl, alkylaminocarbonyl, alkoxycarbonylamino, alkylamino (optionally substituted by hydroxy, alkylamino, alkoxy, oxo, aryl or cycloalkyl), aminoalkyl (substituted by hydroxy, alkylamino, alkoxy, oxo, aryl or cycloalkyl), amino, halo, cyano, nitro, thiol, alkylthio, alkylsulphonyl, alkylsulphenyl, alkylsulphonamido, alkylaminosulphonyl, aminosulphonyl, haloalkoxy and haloalkyl.

Preferably $X^3$ is O.

Examples of more specific values for $R_{3a}$ include hydrogen, hydroxyl, methoxy, ethoxy, methyl, ethyl, hydroxymethyl, carboxy, methoxymethyl, methoxycarbonyl, ethoxycarbonyl, methylaminocarbonyl, dimethylamino-carbonyl, aminomethyl, $CONH_2$, $CH_2CONH_2$, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl, bromo, —$OCH_2O$— (which is bonded to two adjacent ring atoms in Cy) and —$C(X^3)N(R^{11})R^{12}$ (wherein $X^3$ is O or S and $R^{11}$ and $R^{12}$ are independently selected from hydrogen, methyl or ethyl or together with the nitrogen atom to which they are attached form a pyrrolidin-1-yl, piperidin-1-yl or morpholino group).

More examples of specific values for $R_{3a}$ include hydrogen, hydroxyl, methoxy, ethoxy, methyl, ethyl, hydroxymethyl, carboxy, methoxymethyl, methoxycarbonyl, ethoxycarbonyl, methylaminocarbonyl, dimethylamino-carbonyl, aminomethyl, $CONH_2$, $CH_2CONH_2$, acetylamino, methoxycarbonylamino, ethoxycarbonylamino, t-butoxycarbonylamino, amino, fluoro, chloro, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy and trifluoromethyl.

Preferably $R_{3a}$ is hydrogen, hydroxyl, methoxy, methyl, amino, fluoro, chloro, ethylsulphonylamino, amido or methylaminocarbonyl.

Preferably Cy is selected from:

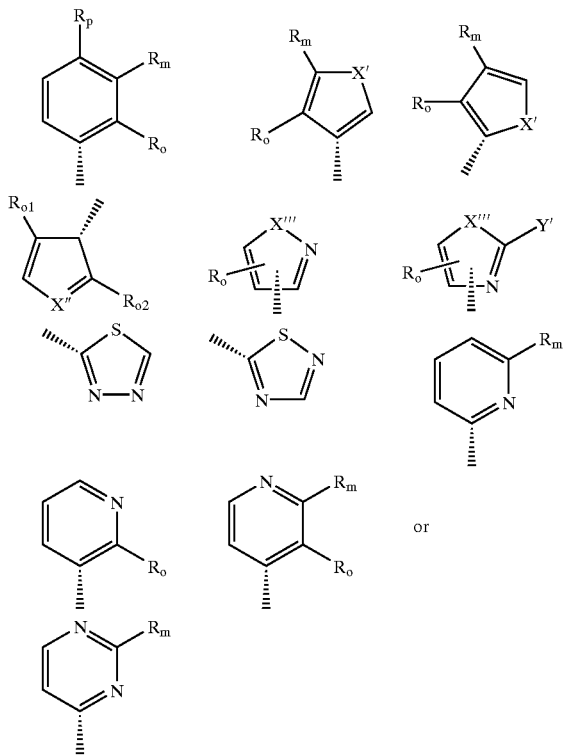

wherein:
X' is selected from O, S and NMe;
X" is selected from O and S;
X''' is selected from O, S, NH and NMe;
Y' is selected from hydrogen, amino and methyl;
$R_o$ is selected from hydrogen, methyl, fluoro, chloro, trifluoromethyl, methoxy, methylthio, methylsulphinyl and methylsulphonyl;
$R_m$ is selected from hydrogen, methyl, fluoro, chloro, trifluoromethyl, methoxy, methylthio, methylsulphinyl, methylsuphonyl, carboxy, methoxycarbonyl and a group of the formula $—C(X^3)N(R^{11})R^{12}$ (wherein $X^3$ is O or S and $R^{11}$ and $R^{12}$ are independently selected from hydrogen, methyl or ethyl or
together with the nitrogen atom to which they are attached form a pyrrol:idin-1-yl, piperidin-1-yl or morpholino group);
$R_p$ is selected from hydrogen and fluoro; or
$R_o$ and $R_m$ or $R_m$ and $R_p$ form an $—OCH_2O—$ group; or
$R_o$ and $R_m$ together with the ring to which they are attached form a 5 or 6 membered aryl or heteroaryl ring (wherein the heteroary ring contains 1 or 2 heteroatoms selected from nitrogen, oxygen and sufur);
one of $R_{o1}$ and $R_{o2}$ is hydrogen and the other is $R_o$.

More preferably Cy is selected from phenyl (optionally substituted by methyl, ethyl, prop-2-yl, phenoxy, hydroxy, ethoxy, benzyloxy, prop-2-yloxy, nitro, amino, acetylamino, methylsulfonylamino, dimethylamino, chloro, methoxy, trifluoromethyl, methylthio, methylsulfonyl, tert-butylthio, tert-butylsulfonyl, aminosulfonyl or carbamoyl), pyridyl, thienyl, furanyl, imidazolyl, thiazolyl (optionally substituted by amino), napththyl, isoquinolinyl and quinolinyl.

Yet more preferably, Cy is selected from phenyl, 2-chlorophenyl, 2-methoxyphenyl, 4-carbamoylphenyl, pyrid-2-yl, pyrid-3-yl, pyrid-4-yl, thien-2-yl, thien-3-yl, furan-2-yl, furan-3-yl, imidazol-2-yl, thiazol-2-yl, thiazol-4-yl, thiazol-5-yl, naphthyl, isoquinolin-5-yl, isoquinolin-8-yl, quinolin-4-yl, quinolin-5-yl, and quinolin-8-yl.

Other examples of values for Cy are 4-aminophenyl, 4-N-methylamidophenyl, 4-(N,N-dimethyl)amidophenyl, 2-methylphenyl, 2-fluorophenyl, 3-fluorophenyl, 4-fluorophenyl, 4-hydroxyphenyl, 4-methoxyphenyl, 4-carboxyphenyl, 3-ethylsulphonylaminophenyl, 2-methylthiazol-4-yl, 1-methylpiperidin-4-yl, cyclopentyl, cyclohexyl, naphth-1-yl, 2-aminothiazol-4-yl, 2-trifluoromethylphenyl, 3-methylthiophenyl, 2-methylsulphonylphenyl, 3-bromophenyl, 3-cyanophenyl and benzo[b]thiophen-3-yl.

Yet more preferably Cy is selected from phenyl, 2-chlorophenyl, 2-methoxyphenyl, 4-carbamoylphenyl, pyrid-2-yl, pyrid-4-yl, thien-2-yl, thien-3-yl, furan-2-yl, furan-3-yl, imidazol-2-yl, thiazol-2-yl, thiazol-4-yl, thiazol-5-yl and quinolin-4-yl.

Most preferably, Cy is selected from phenyl, 2-methoxyphenyl, 4-carbamoylphenyl and pyrid-2-yl.

Most preferably Cy is phenyl.

Examples of particular values for $R_{1c}$ are:
hydrogen;
hydroxyl;
for alkoxy: methoxy or ethoxy; for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl: hydroxymethyl;
for alkoxyalkyl: methoxymethyl;
for alkoxycarbonyl: methoxycabonyl or ethoxycarbonyl;
for alkylaminocarbonyl: methylaminocarbonyl or dimethylaminocarbonyl;
for alkoxycarbonylamino: methoxycarbonylamino, ethoxycarbonylamino or t-butoxycarbonylamino;
for alkylamino optionally substituted by hydroxy, alkylamino, alkoxy, oxo, aryl or cycloalkyl: (1–6C) alkanoylamino, such as acetylamino; and
for aminoalkyl substituted by hydroxy, alkylamino, alkoxy, oxo, aryl or cycloalkyl: aminomethyl, $CONH_2$ or $CH_2CONH_2$.

Referring to $R^2$, examples of a 5 or 6 membered aromatic carbon ring optionally interrupted by a nitrogen, oxygen or sulphur ring atom in $R^2$ are phenyl; pyrrolyl, such as 2-pyrrolyl; pyridyl, such as 3-pyridyl; pyrazinyl, such as 2-pyrazinyl; furyl, such as 2-furyl; and thienyl, such as 2-thienyl or 3-thienyl. Preferably the ring is interrupted (i.e. a carbon atom is replaced) by at most one heteroatom. In another aspect the ring is phenyl, 2-thienyl or 2-pyrrolyl. In yet another aspect, the ring is phenyl.

When the ring is phenyl, the group $R_2$ may be a group of formula

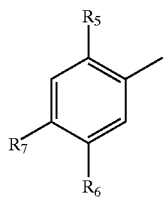

in which $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy.

When the substituents at the 3 and 4 positions taken together form a fused ring which is a 5 or 6 membered carbocyclic or heterocyclic ring, examples of the resultant bicyclic ring are naphthyl, such as 2-naphthyl; benzimidazolyl, such as benzimidazol-5-yl or benzimidazol-6-yl; isoquinolinyl, such as isoquinolin-7-yl; indolyl, such as indol-2-yl, indol-5-yl or indol-6-yl; indazolyl, such as indazol-5-yl; indazol-6-yl; 3,4-methylenedioxyphenyl; dihydroindolyl, such as 2,3-dihydroindol-6-yl; benzothiazolyl, such as benzothiazol-2-yl or benzothiazol-6-yl; benzo[b]thiophenyl, such as benzo[b]thiophen-2-yl; benzofuryl, such as benzofur-2-yl; imidazo[1,2-a]pyrimidinyl, such as imidazo[1,2-a]pyrimidin-2-yl; tetrahydroimidazo[1,2-]pyrimidinyl, such as tetrahydroimidazo[1,2-a]pyrimidin-2-yl; and benzisoxazolyl, such as benzisoxazol-5-yl.

Preferably, $R_2$ is phenyl, thien-2-yl, naphthyl, indol-2-yl, indol-6-yl, benzo[b]furan-5-yl, benzo[b]thiophen-2-yl or benzimidazol-:2-yl (each of which is optionally substituted as hereinabove defined).

It is preferred that at least one of $R_6$ and $R_7$ be other than hydrogen and that $R_6$, if present, is preferably a substituent containing one or more polar hydrogens such as hydroxy, amino, alkylamino, alkylaminoalkyl, aminocarbonyl, alkylaminocarbonyl, hydrazo and alkylhydrazo; alternatively $R_6$ and $R_7$ are joined together in the formation of a naphthyl or indolyl or azaindolyl or diazaindolyl group.

It is especially preferred that $R_6$ be amino and $R_7$ be chloro, bromo, methyl, methoxy or vinyl; or that $R_6$ and $R_7$ taken together form an indolyl ring with the NH at the 6-position or taken together form a naphthyl ring.

In another aspect $R_2$ represents:
(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or $R_1$, and optionally substituted at the 6 position by amino, hydroxy, halo, alkyl, carboxy, alkoxycarbonyl, cyano, amido, aminoalkyl, alkoxy or alkylthio;
(ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;
(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or $R_1$;
(iv) benzimidazol-5-yl or benzothiazol-6-yl optionally substituted at the 2 position by amino;
(v) thien-2-yl or thien-3-yl optionally substituted at the 4 or 5 position by halo, haloalkoxy, haloalkyl, cyano, nitro, amino, hydrazido, alkylthio, alkenyl, alkynyl or $R_1$;
(vi) 3,4-methylenedioxyphenyl, 2,3-dihydroindol-6-yl, 3,3-dichloro-2-oxo-indol-6-yl or 1-methyl-3-aminoindazol-5-yl;
(vii) benzothiazol-2-yl, imidazo[1,2-a]pyrimidin-2-yl or tetrahydroimidazo[1,2-a]pyrimidin-2-yl;
(viii) pyrazol-2-yl optionally substituted at the 5 position by halo, haloalkoxy, haloalkyl, cyano, nitro, amino, hydrazido, alkylthio, alkenyl, alkynyl or $R_1$;
(ix) pyrid-2-yl optionally substituted at the 5 position by halo, haloalkoxy, haloalkyl, cyano, nitro, amino, hydrazido, alkylthio, alkenyl, alkynyl or $R_1$;
(x) pyrid-3-yl optionally substituted at the 6 position by halo, haloalkoxy, haloalkyl, cyano, nitro, amino, hydrazido, alkylthio, alkenyl, alkynyl or $R_1$;
(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;
(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or $R_{1j}$;
(xiii) indol-6-yl substituted at the 5 position by amino, hydroxy, halo (such as fluoro or chloro), alkyl, carboxy, alkoxycarbonyl, cyano, amido, aminoalkyl, alkoxy or alkylthio and optionally substituted at the 3 position by halo (such as chloro), haloalkoxy, haloalkyl, cyano, nitro, amino, hydrazido, alkylthio, alkenyl, alkynyl or $R_{1j}$; or
(xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$.

Examples of particular values for substituents that may be present on $R_2$ are:
for halo: fluoro, chloro, bromo or iodo;
nitro;
thiol;
for haloalkoxy: difluoromethoxy or trifluoromethoxy;
hydrazido;
for alkylhydrazido: methylhydrazido;
amino;
cyano;
for haloalkyl: trifluoromethyl;
for alkylthio: methylthio;
for alkenyl: vinyl;
for alkynyl: ethynyl;
for acylamino: acetylamino;
carboxy;
for acyloxy: acetoxy;
hydroxy;
for alkyl: methyl or ethyl;
amido (CONH$_2$);

for aminoalkyl: aminomethyl; and for alkoxy: methoxy or ethoxy.

Preferably $R_2$ is optionally substituted by 1 or 2 substituents selected from fluoro, chloro, amino, methyl, ethyl and methoxy.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, alkylaminoalkyl, such as dimethylaminomethyl, or alkanoyl, such as acetyl;
for hydroxyalkyl: hydroxymethyl;
for alkoxyalkyl: methoxymethyl;
for alkoxycarbonyl: methoxycarbonyl;
for alkylaminocarbonyl: methylaminocarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

Examples of particular values for $R_{1j}$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, or alkanoyl, such as acetyl;
for hydroxyalkyl: hydroxymethyl;
for alkoxyalkyl: methoxymethyl;
for alkoxycarbonyl: methoxycarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

In yet another aspect $R_2$ represents:
(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl (preferably phenyl substituted in the 4 position by chloro, amino, vinyl, methylamino, methyl or methoxy, optionally at the 3 position with amino or hydroxy, and optionally at the 6 position with amino or hydroxy);
(ii) naphth-2-yl optionally substituted at the 6, position by hydroxy and optionally substituted at the 3 position by amino or hydroxy;
(iii) isoquinolin-7-yl, indol-5-yl, indol-6-yl, indazol-5-yl, indazol-6-yl, benzothiazol-6-yl or benzisoxazol-5-yl optionally substituted at the 3 position by chloro, bromo, amino, methyl or methoxy (preferably indol-6-yl optionally substituted at the 3 position by chloro, bromo, methyl or methoxy);
(iv) benzimidazol-5-yl or benzothiazol-6-yl optionally substituted at the 2 position by amino;
(v) thien-2-yl or thien-3-yl optionally substituted at the 4 or 5 position by methylthio, methyl or acetyl;
(vi) 3,4-methylenedioxyphenyl, 2,3-dihydroindol-6-yl, 3,3-dichloro-2-oxo-indol-6-yl or 1-methyl-3-aminoindazol-5-yl;
(vii) benzothiazol-2-yl, imidazo[1,2-a]pyrimidin-2-yl or tetrahydroimidazo[1,2-a]pyrimidin-2-yl;
(viii) pyrazol-2-yl substituted at the 5 position by methyl;
(ix) pyrid-2-yl optionally substituted at the 6 position by chloro;
(x) pyrid-3-yl optionally substituted at the 4 position by chloro;
(xi) benzofur-2-yl optionally substituted at the 3 position by chloro, methyl or methoxy, at the 5 or 6 position by methyl and at the 6 position by methoxy;
(xii) indol-2-yl optionally substituted on the indole nitrogen atom by methyl and optionally substituted at the 5 or 6 position by fluoro, chloro, bromo, methyl or methoxy;
(xiii) indol-6-yl substituted at the 5 position by chloro, fluoro or hydroxy and optionally substituted at the 3 position by chloro or methyl; or
(xiv) benzo[b]thiophen-2-yl optionally substituted at the 3 position by fluoro, chloro or methyl, and optionally substituted at the 5 or 6 position by fluoro, chloro, methyl, hydroxy, or methoxy.

Particular values for $R_2$ are:
(i) phenyl, 2-aminophenyl, 3-aminophenyl, 2-amino-3-fluorophenyl, 2-amino-4-fluorophenyl, 2-amino-4-chlorophenyl, 2-amino-3-bromophenyl, 2-amino-3-nitrophenyl, 2-amino-4-nitrophenyl, 3,4-dimethoxy-5-aminophenyl, 2-amino-4-methylphenyl, 2-amino-3-methylphenyl, 2-amino-3-methoxyphenyl, 3,4-diaminophenyl, 3,5-diaminophenyl, 3-amino-4-fluorophenyl, 3-amino-4-chlorophenyl, 3-amino-4-bromophenyl, 3-amino-4-hydroxyphenyl, 3-amino-4-carboxymethylphenyl, 3-amino-4-methylphenyl, 3-amino-4-methoxyphenyl, 2-fluorophenyl, 4-fluoro-3-cyanophenyl, 3-chlorophenyl, 3-chloro-4-hydroxphenyl, 3-chloro-5-hydroxyphenyl, 4-chlorophenyl, 4-chloro-2-hydroxyphenyl, 4-chloro-3-hydroxyphenyl, 4-chloro-3-methylphenyl, 4-chloro-3-methoxyphenyl, 4-bromophenyl, 4-bromo-3-methylphenyl, 4-iodophenyl, 2-cyanophenyl, 3-cyanophenyl, 4-cyanophenyl, 3-cyano-5-aminophenyl, 2-hydroxphenyl, 2-hydroxy-4-methoxyphenyl, 3-hydroxphenyl, 3-hydroxy-4-methylphenyl, 2,4-dihydroxyphenyl, 3,4-dihydroxyphenyl, 3-hydroxy-4-methoxyphenyl, 4-difluoromethoxyphenyl, 4-trifluoromethoxphenyl, 4-trifluoromethylphenyl, 4-methylthiophenyl, 4-methoxycarbonylphenyl, 4-acetoxyphenyl, 4-methanesulfonylphenyl, 3-methylphenyl, 3-methyl-5-aminophenyl, 4-methylphenyl, 4-vinylphenyl, 4-methoxyphenyl, 4-ethoxyphenyl, 4-methoxy-3-chlorophenyl, 4-methoxy-3-methylphenyl, 3-methylaminophenyl, 4-methylaminophenyl, 4-ethylaminophenyl or 2-aminomethylphenyl;
(ii) naphth-2-yl, 3-aminonaphth-2-yl, 3-hydroxynaphth-2-yl or 6-hydroxynaphth-2-yl;
(iii) isoquinolin-7-yl, indol-5-yl, indol-6-yl, 3-chloroindol-6-yl, 3-bromoindol-6-yl, 3-methylindol-6-yl, 3-methoxyindol-6-yl, indazol-5-yl, 3-aminoindazol-5-yl, indazol-6-yl, benzothiazol-6-yl, 3-aminobenzisoxazol-5-yl;
(iv) benzimidazol-5-yl, 2-aminobenzimidazol-5-yl, or benzothiazol-6-yl;

(v) thien-2-yl, 5-methylthien-2-yl, 5-methylthio-thien-2-yl, 5-acetylthien-2-yl or thien-3-yl;
(vi) 3,4-methylenedioxyphenyl, 2,3-dihydroindol-6-yl, 3,3-dichloro-2-oxo-indol-6-yl or 1-methyl-3-aminoindazol-5-yl;
(vii) benzothiazol-2-yl, imidazo[1,2-a]pyrimidin-2-yl or tetrahydroimidazo [1,2-a]pyrimidin-2-yl;
(viii) 5-methylpyrazol-2-yl;
(ix) 5-chloropyrid-2-yl;
(x) pyrid-3-yl, 6-chloropyrid-3-yl;
(xi) benzofur-2-yl, 5-chlorobenzofur-2-yl, 3-methylbenzofur-2-yl, 5-methylbenzofur-2-yl, 6-methoxybenzofur-2-yl;
(xii) indol-2-yl, 5-fluoroindol-2-yl, 5-chloroindol-2-yl, 5-methylindol-2-yl, 5-methoxindol-2-yl, 6-methoxyindol-2-yl and 1-methyl-indol-2-yl;
(xiii) 5-fluoroindol-6-yl; or
(xiv) benzo[b]thiophen-2-yl, 5-chloro-benzo[b]thiophen-2-yl or 6-chlorobenzo[b]thiophen-2-yl.

Preferably, $R_2$ is selected from one of the formulae (A') to (H'):

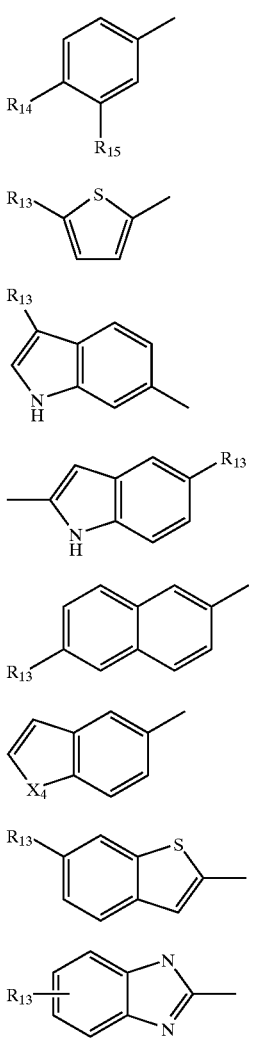

wherein $X_4$ is O or S, $R_{13}$ is selected from hydrogen, fluoro [except for (C')], chloro or methyl and $R_{14}$ is selected from hydrogen, methyl, ethyl, fluoro, chloro, and methoxy and $R_{15}$ is selected from hydrogen, methyl, fluoro, chloro and amino.

More preferably, $R^2$ is of the formula (A') (wherein $R_{14}$ is selected from hydrogen, methyl, ethyl, fluoro, chloro, and methoxy and $R_{15}$ is selected from hydrogen, methyl, fluoro, chloro and amino) or of the formula (B') (wherein $R_{13}$ is chloro) or of the formula (C') (wherein $R_{13}$ is selected from hydrogen, methyl and chloro) or of the formula (D') (wherein $R_{13}$ is selected from hydrogen, methyl, fluoro and chloro) or of the formula (E') (wherein $R_{13}$ is hydrogen) or of the formula (G') (wherein $R_{13}$ is chloro).

Yet more preferably, $R_2$ is 4-chlorophenyl, 4-methoxyphenyl, 3-amino-4-chlorophenyl, indol-2-yl, 5-chloroindol-2-yl, indol-6-yl, 3-chloroindol-6-yl or 3-methylindol-6-yl. Another $R_2$ group of particular interest is 3-aminobenzisoxazol-5-yl.

Yet more preferably, $R_2$ is of the formula (A') or (C') and $R_{13}$, $R_{14}$ and $R_{15}$ are as defined hereinabove.

Most preferably, $R_2$ is of the formula (A') and $R_{14}$ is methoxy and $R_{15}$ is hydrogen or of the formula (C') and $R_{13}$ is hydrogen, methyl or chloro.

Another preferred compound of the present invention is one of the formula:

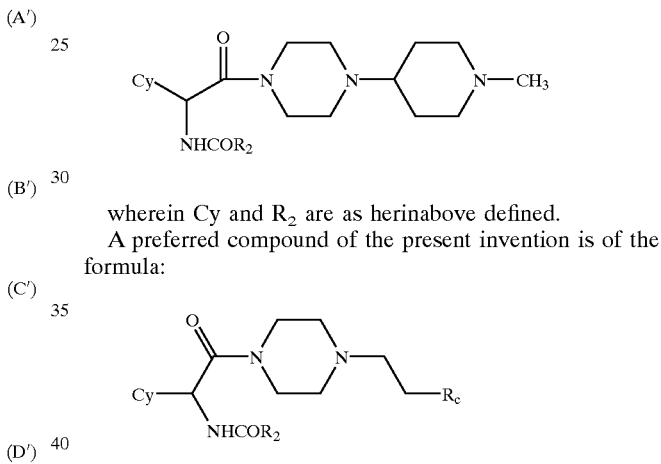

wherein Cy and $R_2$ are as herinabove defined.

A preferred compound of the present invention is of the formula:

wherein Cy, $R_2$ and $R_c$ are as hereinabove defined.

Especial mention may be made of:
1-(Indole-6-carbonyl-D-phenylglycinyl)-4-[2-(4-pyridinyl) ethyl]piperazine;
1-(3-Chloroindole-6-carbonyl-D-phenylglycinyl)-4-[2-(4-pyridinyl) ethyl]piperazine;
1-(4-Methoxybenzoyl-D-phenylglycinyl)-4-(1-methylpiperidin-4-yl)piperazine;
1-(Indole-6-carbonyl-D-phenylglycinyl)-4-(1-methylpiperidin-4-yl)piperazine;
1-(4-Methoxybenzoyl-D-(2-chlorophenyl)glycinyl)-4-(1-methylpiperidin-4-yl)piperazine;
1-(Indole-6-carbonyl-D-(2-chlorophenyl)glycinyl)-4-(1-methylpiperidin-4-yl)piperazine; and
1-(4-Methoxybenzoyl-D-(2-trifluoromethylphenyl) glycinyl)-4-(1-methylpiperidin-4-yl)piperazine;
and physiologically-tolerable salts thereof.

Compounds in this group have been found to have good oral exposure and a desirable pharmacological/toxicological profile.

The compounds of the invention may be prepared by conventional chemical synthetic routes or by routes as illustrated by the following examples.

The compounds of the formula (I) may be prepared by forming the —X—X— bond from appropriate intermediates. For example, when —X—X— is —CONH— or —CO—NR$_{1a}$—, by reacting a compound of the formula (10): H$_2$N—Y—(Cy)—L—Lp(D)$_n$ with a compound of the formula R$_2$—COOH, under conditions known for the formation of an amide bond. The reaction is conveniently carried out in the presence of a benzotriazole-based reagent such as 1-hydroxybenzotriazole or 1-hydroxy-7-azabenzotriazole, in an inert organic solvent such as dimethylformamide and/or methylene chloride. The reaction mixture is usually taken to 0° C. and then a dehydrating agent such as dicyclohexylcarbodiimide or 1-(3-dimethylaminopropyl)-3-ethylcarbodiimide added. Other suitable reagents and solvents are known in the art, for example an acid halide, such as R$_2$—COCl.

Compounds wherein —X—X— is —NHCO— or —NHCH$_2$— may be formed from the appropriate intermediates using reaction conditions for the formation of an amide bond as described above and if necessary subsequent reduction of the resulting amide bond.

Compounds of the formula (I) wherein —X—X— is of the formula —CH$_2$NH— may be prepared by reducing the corresponding compound of the formula (I) wherein —X—X— is —CONH— or by reaction of a compound of formula (10): H$_2$N—Y—(Cy)—L—Lp(D)n with a compound of the formula R$_2$CHO and reducing the intermediate of the formula (I) wherein —X—X— is —C=N— with, for example, sodium cyanoborohydride.

When —X—X— is —CH=CH—, the compounds of the formula (I) may be prepared using the Wittig or Horner-Emmons reactions. The corresponding compound in which —X—X— is —CH$_2$CH$_2$— can be formed by reduction of the —CH=CH— group, for example with hydrogen over a palladium-on-carbon catalyst.

An —X—X— bond of the formula —COO— or —OC(O)— may be formed by reacting the appropriate hydroxy and activated carboxylic acid (e.g. acid chloride or reactive ester) intermediates under conditions known for ester bond formation. Alternatively, a hydroxy and a carboxylic acid intermediate could be reacted together in the presence of diethylazodicarboxylate/triphenylphosphine.

An —X—X— bond of the formula —CH$_2$O— or —OCH$_2$— may be formed by reacting the appropriate hydroxy intermediate with the appropriate alkyl halide in the presence of a base. Conditions for the formation of an ether bond are known in the art.

These reactions can also be used to form intermediates, which contain one of the above —X—X— bonds.

Compounds of the formula (I) in which R$_r$ is —(CH$_2$)$_c$—R$_c$ may also be prepared by reductive coupling a compound of the formula (11):

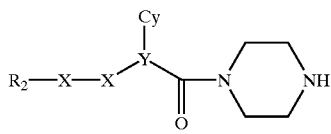

with a compound of formula (12)

OHC—(CH$_2$)$_{c-1}$—R$_c$

The reaction is conveniently performed in the presence of a reducing agent, such as sodium cyanobrohydride. Convenient solvents include alcohols, such as methanol, optionally with a halogenated hydrocarbon as solvent, such as 1,2-dichloroethane, and acetic acid. The coupling is conveniently effected at a temperature in the range of from 0 to 100° C.

The intermediates of formula (11) are believed to be novel, and are provided as a further aspect of the invention.

The intermediates of formula (11) in which X—X is CONH may be prepared by reacting a compound of formula (13)

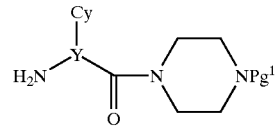

in which Pg$^1$ represents an amino protecting group, such as t-butoxycarbonyl, with a compound of formula R$_2$—COOH, under conditions known for the formation of an amide bond, for example as described hereinabove for forming a compound of formula (I), followed by deprotection.

The compounds of formula (13) may be prepared by reacting an appropriate N-protected glycine of formula (14)

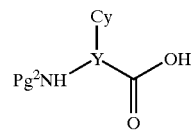

in which Pg$^2$ represents an amino protecting group that can be selectively removed in the presence of Pg$^1$ (for example, when Pg$^1$ is t-butoxycarbonyl, Pg$^2$ may be benzyloxycarbonyl), with a compound of formula (15)

under amide bond forming conditions, followed by selectively removing the protecting group Pg$^2$.

Compounds of the formula (10) in which X is CONH may be prepared by deprotecting a compound of the formula (16):

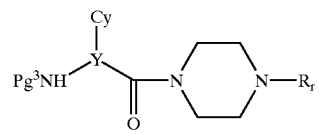

in which Pg$^3$ represents an amino protecting group, such as t-butoxycarbonyl.

The intermediates of formula (16) and the corresponding amines without Pg$^3$ are believed to be novel, and are provided as a further aspect of the invention.

Compounds of formula (16) may be prepared by reacting a compound of formula (14) with a compound of formula (17)

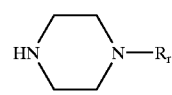

under amide bond forming conditions. The reaction is conveniently performed in the presence of diethylcyanophosphate. Convenient solvents include amides, such as dimethylformamide. The temperature is conveniently in the range of from 0 to 100° C.

Compounds of formula (17) in which $R_r$ is —(CH$_2$)$_c$—$R_c$, may be prepared by reacting a compound of formula (18)

in which Pg$^4$ represents an amino protecting group, such as t-butoxycarbonyl, with a compound of formula (19)

followed by removing the protecting group, Pg$^4$. The reaction is conveniently performed in the presence of an acid, such as acetic acid. Convenient solvents include alcohols, such as ethanol.

Compounds of formula (17) in which $R_r$ is —(CH$_2$)$_c$—$R_c$ may also be prepared by reacting a compound of formula (18) with a compound of formula (19a)

Z—(CH$_2$)$_c$—R$_c$ in which Z represents a leaving atom or group, such as methanesulfonrloxy or benzenesulfonyloxy, followed by removing the protecting group, Pg$^4$.

Compounds of formula (17) in which $R_r$ is —(CH$_2$)$_c$—$R_c$ may also be prepared by reducing compounds of formula (20) or formula (20A)

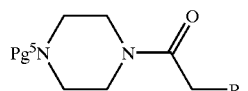

(20)

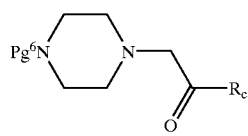

(20a)

in which Pg$^5$ and Pg$^6$ each represent an amino protecting group, such as t-butoxycarbonyl, followed by removing the protecting group, Pg$^5$. The reduction is conveniently performed in the presence of a reducing agent, such as borane, in an ether such as tetrahydrofuran.

Compounds of formula (20) may be prepared by reacting a compound of formula (18) with a compound of formula (21)

HOOC—(CH$_2$)$_{c-1}$—R$_c$ under amide bond forming conditions.

Alternatively, compounds of formula (20) may be prepared by reacting a compound of formula (18) with a compound of formula (21a)

HOOC—(CH)$_c$—X'  (21a)

in which X' is a hydrogen atom, such as bromine, followed by reaction with a compound of formula (21b) HR$_c$ in the presence of a strong base, such as sodium hydride.

Hence the present invention also provides a process for the preparation of a compound of formula (I) comprising:
a) when —X—X is —CONH—, reacting a compound of formula (10) with a compound of formula R$^2$—COOH, under amide bond-forming conditions; or b) when $R_r$ is —(CH$_2$)$_c$—$R_c$, reacting a compound of formula (11) with a compound of (12);
wherein R$_2$, X, Y, Cy, c and $R_r$ are as hereinabove defined and formulae (10) (11) and (12) are as hereinabove defined, followed if a salt is required, by forming a physiologically acceptable salt.

An amino acid of formula (23)

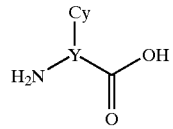

or an N-protected glycine of formula (14) may be prepared (for example) by one or more of the following methods:

(i) from aryl or heteroaryl aldehydes via the Strecker synthesis or modifications thereof, via Bucherer-Bergs hydantoin synthesis, or via the Ugi methodology ("Isonitrile Chemistry", Ugi I. Ed.; Academic: New York, 1971;145-1999, "Multicomponent Reactions with Isocyamides", Domling, A.; Ugi, I. *Angew. Chezn. Int. Ed.* 2000, 39, 3168; "Amino Acid Derivatives by Multicomponent Reactions", Dyker, G. Angew, *Chem. Int. Ed. Engl.* 1997, 36, 1700; and also see "A new Class of Convertible Isocyamides in the Ugi Four-Component Reaction", Lindhorst, T.; Bock H.; Ugi, I. *Tetrahedron,* 1999, 55, 7411.) with removal and replacement of protecting groups;

(ii) from styrenes via Sharpless methodology (J. Am. Chem. Soc. 1998,120, 1207–1217)

(iii) from aryl boronic acids via Petasis methodology (Tetrahedron, 1997, 53, 16463–16470) with removal and replacement of protecting groups;

(iv) from aryl and heteroaryl acetic acids—via Evan's azidation (Synthesis, 1997, 536–540) or by oximation, followed by reduction and addition of protecting groups; or (v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid;

(vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490); or (vii) from oximes of formula

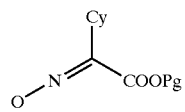

in which Pg is a carboxy protecting group, by reduction. (Oximes in which Cy is a heteroaryl group may be prepared from compounds of formula

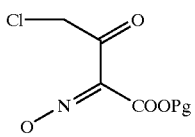

Alternatively, oximes may be prepared by nitrosation of a compound of formula Cy—CH$_2$—COOPg, or by reaction of hydroxylamine with a compound of formula Cy—CH—COOPg).

A starting material for the preparation of a compound of formula (I), where the alpha atom is nitrogen, may be produced, for example, by reaction of a beta protected hydrazine (such protection to be chosen as to be compatible with the subsequent reagents to be employed) with phosgene, diphosgene, triphosgene or N,N'carbonyl diimidazole to give a reactive compound of the type PGNHN(Cy)COCl or PGNHN(Cy)CO-imidazole (wherein PG is a protecting group).

This intermediate may be used as has been described above for the carboxylic starting reagents where the alpha atom is carbon.

The skilled person will be aware that at certain stages in the synthesis of a compound of formula (I) it may be necessary to protect a reactive functional group in the molecule to prevent unwanted side-reactions.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy.

Preferred amino protecting groups include benzyloxycarbonyl (CBz), t-butoxycarbonyl (Boc) and benzyl.

In another aspect the invention relates to a process for preparing a compound of formula I comprising deprotecting a compound of formula (I'):

$$R^{2'}—X—X—Y(Cy')—L—Lp(D)_n'$$ (I)

Wherein $R^{2'}$ is $R^2$ (as hereinabove defined) or protected $R^2$, Cy' is Cy (as hereinabove defined) or protected Cy and $Lp(D)_n'$ is $Lp(D)_n$ (as hereinabove defined) or protected $Lp(D)_n$; providing at least one protecting group is present.

If necessary physiologically tolerable salts can be formed using methods known in the art.

It will be understood that the compounds of formula (I) may be isolated in the form of salts or solvates (which may or may not be physiologically tolerable), and that all such salts and solvates are therefore included within the scope of the present invention.

All novel intermediates described herein, for example the compounds of formula

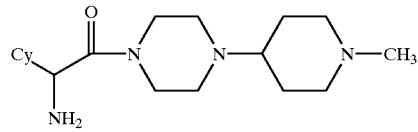

and salts thereof, are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1

Hard Gelatin Capsules are Prepared Using the Following Ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets Each Containing 60 mg of Active Ingredient are Made as Follows:

|  |  |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease inhibitor according to the invention together with at least one pharmaceutically acceptable carrier or excipient. The pharmaceutical composition may also optionally comprise at least one further antithrombotic and/or thrombolytic agent.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor) said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 µmol/kg bodyweight will be administered.

All publications referred to herein are hereby incorporated by reference.

The invention will now be described further with reference to the following non-limiting Examples.

Experimental

Abbreviations used follow IUPAC-IUB nomencalture. The following abbreviations are used throughout: aq. (aqueous), equiv, ([molar] equivalent), Boc (tertiary-butyloxycarbonyl), CMA (chloroform: methanol, concentrated ammonium hydroxide 80:18:2), DCC (1,3-dicyclohexylcarbodiimide), DCM (dichloromethane), DEPC (diethyl cyanophosphonate), DIPEA (diisopropylethylamine), DMEA (dimethylethylamine), DMF (dimethylformamide), DMSO (dimethyl sulfoxide, perdeuterated if for NMR), EDCI (1-(3-dimethylaminopropyl)-3-ethylcarbodiimide hydrochloride), EtOAc (ethyl acetate), EtOH (ethanol), HATU ([O-(7-azabenzotriazol-1-yl)-1,1,3,3-tetramethyluronium hexafluorophosphate]), HOAt (1-hydroxy-7-azabenzotriazole), HOBt (1-hydroxy-benzotriazole), HPLC (high-performance liquid chromatography), IS-MS (ion spray mass spectrum), RPHPLC (reverse phase high-performance liquid chromatography), SCX (strong cation exchange resin), TFA (trifluoroacetic acid), THF (tetrahydrofuran), TLC (thin layer chromatography with $R_f$ as relative mobility), DSC (differential scanning calorimetry), TGA (thermal gravimetric analysis).

All solution concentrations are expressed as %Vol./%Vol. unless otherwise stated. Reagents were obtained from a variety of commercial sources.

IR means an infrared spectrum was obtained. $^1$NMR, NMR, 1H-NMR, or 1H NMR means a proton magnetic resonance spectrum was obtained.

HPLC Analysis (Methods A to D)

(Method A): Vydac C18 (4.6×250 mm), elute with a linear gradient of 90/10 through 50/50 (0.1% TFA in water/0.1% TFA in acetonitrile) over 40 min, 1 mL/min.

(Method B): Waters Symmetry, C18 (4.6×250 mm) column. The elution system consisted of linear gradient from 95:5 (0.2% TFA in H$_2$O)/(0.2% TFA in CH$_3$CN) to 5:95 (0.2% TFA in H$_2$O)/(0.2% TFA in CH$_3$CN) over 20 min, followed by (0.2% TFA in CH$_3$CN) isocratic over 15 min. The flow rate was 1 ml/min. UV Detection was performed at 254 nm unless otherwise noted.

(Method C): Shimadzu LC6 gradient system equipped with an autosampler, a variable wavelength detector at flow rates of 0.4 ml/min. Eluant A consisted of aqTFA (0.1%) and eluant B 90% MeCN in aq TFA(0.1%) with gradient elution (0 min. 20%B then 20% to 100% over 15 min.); Luna C18 (2.1×150 mm, 5 µM particle size).

(Method D): Microsorb-MV C18 (4.6×250 mm) column. The elution system consisted of a linear gradient from 90:10 (2.5% TFA in H$_2$O):(2.5% TFA in acetonitrile) to 10:90 (2.5% TFA in H$_2$O):(2.5% TFA in acetonitrile) over 25 min at 30° C. and a flow rate of 1 mL/min. UV Detection was performed at 254 nm unless otherwise noted.

API-MS (atmospheric pressure chemical ionization mass spectra) were obtained on a PESciex API 150EX with a heated nebulizer and nitrogen as the reagent gas in positive ion mode.

CI-MS (Chemical ionization mass spectra) were obtained on a Shimadzu 5000 direct insertion mass spectrometer in chemical ionization mode utilizing methane as the reagent gas.

MALDI-TOF, Matrix assisted laser desorption ionisation—time of flight mass spectrometry, RT, retention time.

In general in this specification, "D-" or "R-" in the name of a product indicates the product was made beginning with a chiral starting material, for example D-phenylglycine.

Preparation of Starting Materials and Intermediates

Intermediate substituted glycine compounds for starting materials and intermediates, including those in which the amino group and/or the carboxy group is protected, conveniently may be prepared using one of the procedures below, or by a similar procedure. It may be convenient or preferred to change the order of steps in the preparation of a compound of the invention and to use a similar procedure with a different intermediate. In particular, it may be convenient to use an acyl group R$_2$—CO— initially in a preparation, rather than an amino protecting group.

Abbreviations, in addition to others listed herein, include: TEMPO: 2,2,6,6-tetramethyl-1-piperidinyloxy, free radical; (DHQD)$_2$PHAL: hydroquinidine 1,4-phthalazinediyl diether; r.b. or rb, round bottomed; PPh$_3$, triphenylphosphine; Boc$_2$O or Boc anhydride: di-tert-butyl dicarbonate.

Preparation of Intermediates KE-1- KE-5

The following compounds were prepared according to the indicated method (Method KE-A) from the indicated starting materials, unless otherwise described.

Intermediate KE-1

Ethyl oxo-quinolin-8-ylacetate.

Method KE-A

To a stirring solution of 8-bromoquinoline (10.1 g, 48.5 mmol) in THF (500 mL) at −78° C. was added dropwise a 1.3 M solution of sec-butyl lithium (37.3 mL, 48.5 mmol) in cyclohexane. After 5 min, diethyl oxalate (8 mL, 58.3 mmol) was added; and the solution was allowed to slowly warm to room temperature overnight. The next morning, the reaction was quenched with the addition of saturated aqueous NH$_4$Cl; and the solvent was removed in vacuo. The residue was partitioned between ethyl acetate and satd aq. NaHCO$_3$; the layers were separated; and then the aqueous phase was washed with brine, dried with MgSO$_4$, filtered and concentrated in vacuo. The residue was chromatographed over silica gel, eluting with 20% ethyl acetate/hexanes through 25% ethyl acetate/hexanes. The product containing fractions were combined and concentrated in vacuo to give 5.88 g (53%) of the title compound.

1H-NMR

IS-MS, m/e 230.1 (M+1)

Intermediate KE-2

Ethyl oxo-quinolin-5-ylacetate.

Prepared from 5-bromoquinoline and diethyl oxalate using Method KE-A.

1H-NMR

IS-MS, m/e 230.0 (M+1)

Intermediate KE-3

Ethyl oxo-thiazol-5-ylacetate.

To a r.b. flask (500 cm$^3$) under argon, fitted with ethanol thermometer, septum cap, and dropping funnel, was added anhydrous ether (100 cm$^3$) with stirring. This was cooled to −78° C. and 2 M n-butyllithium (60 cm$^3$, 120 mmol) was added.

A solution of silyl thiazole (16 g, 16 cm$^3$, 100 mmol) in anhydrous ether (100 cm$^3$) was then added by dropping funnel over 30 minutes. This was allowed to stir for 1 hour to give a peach suspension. To this was added diethyl oxalate (16.3 cm$^3$, 17.5 g, 120 mmol) rapidly to give a brown solution, resulting in a temperature increase to −30° C. This was allowed to cool back to −78° C. and stirred for 30 minutes. Reaction monitored by $^1$H NMR (CDCl$_3$).

The brown solution was poured onto 5% hydrochloric acid solution (300 cm$^3$) with vigorous stirring for 30 minutes. Ether layer was separated and washed with saturated bicarbonate (ca. 80 cm$^3$), dried over magnesium sulphate, and concentrated in vacuo to give an orange oil. This was purified by flash chromatography (10% ethyl acetate/hexane) to give a yellow oil (7.31 g, 39.47 mmol) [40% Yield].

$^1$H NMR (CDCl$_3$); 1.42 (3H, t), 4.45 (2H, q), 8.89 (1H, s), 9.10 (1H, s).

Intermediate KE-4

Ethyl oxo-thiazol-2-ylacetate.

Prepared from thiazole and diethyl oxalate using Method KE-A. In this case the temperature was held at −35° C. and n-butyllithium in hexane was used in place of sec-butyllithium in cyclohexane.

$^1$NMR

IS-MS, m/e 165.0 (M+1)

Intermediate KE-5

Ethyl oxo-isoquinolin-8-ylacetate.

Prepared from 8-bromoisoquinoline and diethyl oxalate using Method KE-A, substituting n-butyl lithium in hexanes for sec-butyl lithium in cyclohexane.

$^1$NMR

IS-MS, m/e 230.0 (M+1)

| Analysis for C$_{13}$H$_{11}$NO$_3$: | |
|---|---|
| Calcd: | C, 68.11; H, 4.84; N, 6.11; |
| Found: | C, 68.11; H, 5.00; N, 6.14. |

Preparation of Intermediates OX-1- OX-9

The following compounds were prepared according to the indicated method (Method OX-A or Method OX-B) from the indicated starting materials unless otherwise described.

Intermediate OX-1

Ethyl Hydroxyimino-pyridin-2-ylacetate.

Method OX-A

To a stirring solution of ethyl 2-pyridylacetate (12.6 g, 76.3 mmol) in acetic acid (19 mL) at 5° C. was added a solution of sodium nitrite (6.05 g, 87.7 mmol) in water (12 mL) at a rate sufficient to maintain the internal temperature below 15° C. After complete addition and an additional 30 min, an additional 30 mL of water were added. The resulting white precipitate was filtered, washed with water, satd aq. NaHCO$_3$, and again with water. The solid was then dried under vacuum to give 14.1 g (95%) of the title compound.

1H-NMR

IS-MS, m/e 194.9 (M+1)

| Analysis for C$_9$H$_{10}$N$_2$O$_3$: | |
|---|---|
| Calcd: | C, 55.67; H, 5.19; N, 14.43; |
| Found: | C, 55.79; H, 5.14; N, 14.13. |

Intermediate OX-2

Ethyl Hydroxyimino-pyridin-3-ylacetate.

Using the procedure of Tikk et al [Acta. Chimica, Hungarica, 114(3–4), 355], a mixture of ethyl hydroxyiminopyridin-3-yl-acetate and n-butyl hydroxyimino-pyridin-3-yl-acetate was prepared from ethyl 3-pyridinylacetate and n-butyl nitrite.

1H-NMR

IS-MS, m/e 195 (M+1), 223.1 (M+1)

Intermediate OX-3

Ethyl Hydroxyimino-quinolin-8-ylacetate.

Method OX-B

To a stirring solution of ethyl oxo-quinolin-8-yl-acetate (5.5 g, 24 mmol) in ethanol (140 mL) was added sodium acetate (2.16 g, 26.4 mmol) followed by hydroxylamine hydrochloride (2.67 g, 38.4 mmol). The mixture was heated to reflux; and, after 7 h, the heating mantle was removed and the solution was allowed to stir overnight at room temperature. The next morning, the solvent was removed in vacuo and the residue was partitioned between ethyl acetate and satd aq. NaHCO$_3$. The layers were separated and the organic phase was washed with brine, dried with Na$_2$SO$_4$, filtered and concentrated in vacuo.

The resulting foam was recrystalized from dichloromethane/hexanes to give an initial crop of 2.5 g of the title compound as an off-white solid, followed by 0.31 g of a second crop. The mother liquor was then concentrated in vacuo, the residue was dissolved in a minimal amount of dichloromethane. The solution was then chromatographed over silica gel, eluting with 30% ethyl acetate/hexanes, then 40% ethyl acetate/hexanes, and finally with ethyl acetate. The product containing fractions were combined and concentrated in vacuo to give 1.94 g of the title compound for a combined yield of 4.75 g (81%)

1H-NMR
IS-MS, m/e 245.0 (M+1)
Intermediate OX-4
Ethyl Hydroxyimino-quinolin-5-ylacetate.
Prepared from ethyl oxo-quinolin-5-yl-acetate using Method OX-B.
1H-NMR
IS-MS, m/e 245.0 (M+1)
Intermediate OX-5
Ethyl Hydroxyimino-thiazol-5-ylacetate.

To a r.b. flask (500 cm$^3$) was added the ethyl oxo-thiazol-5-ylacetate (6.30 g, 34.02 mmol) to ethanol (ca. 180 cm$^3$) with stirring. Sodium acetate (3.06 g, 37.30 mmol) and hydroxylamine hydrochloride (3.78 g, 54.43 mmol) were then added to give an off-white suspension. This was brought to reflux at 85° C. for 1 hour. Reaction monitored by TLC (60% hexane/ethyl acetate; s.m. r.f 0.5, prod. r.f. 0.3.). Reaction cooled and concentrated in vacuo. Product taken up in ethyl acetate (c.a. 200 cm$^3$) and washed with 5% hydrochloric acid solution. Ethyl acetate layer was dried over magnesium sulphate and evaporated to dryness to give a cream solid (6.372 g, 31.825 mmol) [94% Yield].

$^1$H NMR (CDCl$_3$); 1.40 (3H, m), 4.40 (2H, m), 8.06 (⅓H, s), 8.78 (⅓H, s), 8.95 (⅔H, s), 8.98 (⅔H, s).

Intermediate OX-6
Ethyl α-Oximino-thiazole-4-acetate.

To a 2 necked r.b. flask (100 cm$^3$) with ethanol thermometer, concentrated sulphuric acid (25 cm$^3$) was added and cooled to 0° C. with stirring. To this solution was added the ethyl α-oximino-2-aminothiazole-4-acetate (5.00 g, 23.231 mmol). Water (10 cm$^3$) was then added and cooled to −10° C. A solution of sodium nitrite (1.683 g, 24.393 mmol) in water (5 cm$^3$) was then added slowly over an hour keeping the temperature below −5° C.

To a separate r.b. flask (500 cm$^3$), water (180 cm$^3$) was added and cooled to 3° C. The reaction solution was poured in to the cold water with stirring and then cooled to −5° C. To this solution, 50% hypophosphoric acid (90 cm$^3$) was added dropwise over 10 minutes keeping the temperature at −5° C. The solution was allowed to warm to room temperature and stirred overnight. The product was extracted with diethyl ether (ca. 3×150 cm$^3$) and washed with water. The ether layer was concentrated in vacuo and treated to flash chromatography (50% ethyl acetate/n-hexane) to yield a orange oil upon concentration in vacuo (0.60 g, 3.00 mmol) [13% yield].

$^1$H NMR (CDCl$_3$) 1.35 (3H, m), 4.35 (2H, m), 8.4 (11H, s), 8.9 (1H, s), 14.4 (1H, s).

Intermediate OX-7
Ethyl α-Oximino-2-methylthiazole-4-acetate.

This was prepared from ethyl-γ-chloro-α-oximinoacetoacetate (1.44 g) using the method of Hatanaka et al. (*Journal of Medicinal Chemistry*, 1973, 16(9), 978–984) to yield the titled compound (0.64 g).

$^1$H NMR (CDCl$_3$) 1.35 (3H, t), 2.7 (3H, s), 4.35 (2H, q), 8.2 (1H, s).

Ethyl γ-Chloro-α-oximinoacetoacetate.

This was prepared from ethyl oximinoacetoacetate (1.73 g) using the method of Hatanaka et al. (*Journal of Medicinal Chemistry*, 1973, 16(9), 978–984) to yield the titled compound (1.44 g).

$^1$H NMR (CDCl$_3$) 1.25 (3H, t), 4.3 (2H, q), 4.55 (2H, s), 9.45 (1H, s), contains 20% starting material by NMR.

Ethyl Oximinoacetoacetate

This was prepared from ethyl acetoacetate (10.00 g) using the method of Fischer (*Organic Synthesis Coll. Vol. 3*, 513–516) to yield the titled compound (12.45 g).

$^1$H NMR (CDCl$_3$) 1.25 (3H, t), 2.35 (3H, s), 4.3 (2H, q), 8.8 (1H, br.).

Intermediate OX-8
Ethyl hydroxyimino-thiazol-2-ylacetate.
Prepared from ethyl oxo-thiazol-2-ylacetate using Method OX-B.
$^1$NMR
IS-MS, m/e 198.9(M−1)
Intermediate OX-9 Ethyl hydroxyimino-isoquinolin-8-ylacetate.
Prepared from ethyl oxo-isoquinolin-8-ylacetate using Method OX-B.
$^1$NMR
IS-MS, m/e 245.0(M+1)

| Analysis for $C_{13}H_{12}N_2O_3$: | |
|---|---|
| Calcd: | C, 63.93; H, 4.95; N, 11.47; |
| Found: | C, 63.68; H, 4.60; N, 11.34. |

Preparation of Intermediates AL-1-AL-3

The following compounds were prepared according to the indicated method (Method AL-A or Method AL-B) from the indicated starting materials, unless otherwise described.

Intermediate AL-1
R-3-Bromo-(1- t-butoxycarbonylamino-2-hydroxyethyl)benzene.

Method AL-A

Sodium hydroxide (3.33 g, 83.25 mmol) was dissolved in water (220 mL), and 20 mL of the resulting solution was removed and added to potassium osmate (410 mg, 1.11 mmol). The remaining sodium hydroxide solution (200 mL) was added to a stirred solution of t-butyl carbamate (9.9 g, 84.5 mmol) in n-propanol (110 mL) followed by freshly prepared t-butyl hypochlorite (9.65 mL; 83.5 mmol). After stirring for 5 min, the solution was cooled to 0° C. A solution of (DHQD)$_2$PHAL (1.30 g, 1.67 mmol) in n-propanol (110 mL) was added, followed by a solution of 3-bromostyrene (5 g, 27.31 mmol) in n-propanol (220 mL), followed by dropwise addition of the potassium osmate/sodium hydroxide solution. The reaction was stirred overnight. Saturated aqueous sodium sulfite (150 mL) was added, and the reaction was stirred for 15 min. The aqueous layer was separated and extracted with ethyl acetate (3×200 mL). The combined organic layers were washed with brine and dried over MgSO$_4$. Removal of solvent under vacuum gave the crude product which was purified by chromatography (silica, 3:2 hexane:ethyl acetate then rechromatographed loading with toluene, gradient elution with hexane—4:1 hexane:ethyl acetate) to give the title product (4.18 g, 49%).

Melting Point=90–91° C.
$^1$H NMR (CDCl$_3$).
Intermediate AL-2
R-3-Methoxycarbonyl-(1-t-butoxycarbonylamino-2-hydroxyethyl)benzene.

Method AL-B

In a glass liner containing a stirrer bar was placed Pd(OAc)$_2$ (871 mg, 3.88 mmol), PPh$_3$ (1.96 g, 7.47 mmol, NaOAc (1.48 g, 18.04 mmol) and DMF (82 mL). To this stirred solution was added a solution of R-3-bromo-(1-t-butoxycarbonylamino-2-hydroxyethyl)benzene (4.27 g, 13.5 mmol) in MeOH (82 mL). The resulting solution was purged with nitrogen and placed in a stirred pressure vessel.

The system was charged to 4.1 bar (60 psig) of CO and heated at 95° C for 36 h. The mixture was cooled to room temperature, filtered through diatomaceous earth, and partitioned between ethyl acetate and water. The organic layer was washed with water (3×) and brine (1×) and dried over $MgSO_4$. Removal of solvent under vacuum gave the crude product which was purified by chromatography (silica gel, gradient elution with 30–35% ethyl acetate/hexane) to provide the title product (3.53 g, 89%).

Melting Point 73–75° C. with decomposition $^1H$ NMR $(CDCl_3)$.

API-MS, m/e 240 (M-$C_4H_9$+1).

Intermediate A:L-3

R-3-Cyano-(1-t-butoxycarbonylamino-2-hydroxyethyl)benzene.

Prepared from 3-cyanostyrene using Method AL-A. 3-Cyanostyrene was prepared using the method described below.

Melting Point=76° C.

$^1H$ NMR $(CDCl_3)$.

Preparation of 3-Cyanostyrene.

To a stirred suspension of methyltriphenylphosphonium bromide (75 g, 209.71 mmol) in dry THF (750 mL) at 0° C. under nitrogen was added dropwise n-BuLi (83 mL, 2.5 M in hexanes, 207.50 mmol). The mixture was warmed to room temperature. 3-Cyanobenzaldehyde (25 g, 190.65 mmol) was added as a solid in 5 g batches, and the mixture was stirred at room temperature overnight. The reaction was quenched in water, and the solvent was removed under vacuum. The residue was dissolved in the minimal amount of THF, and triphenylphosphine oxide was precipitated using ether. The solid was filtered through diatomaceous earth, and the filtrate was concentrated. Distillation by Kugelrhor at 90° C./33 Pa (0.25 mm Hg) gave the product as a colorless oil (15.5 g, 62%).

Boiling Point=90° C. at 0.25 mmHg.

$^1H$ NMR $(CDCl_3)$.

Preparation of Intermediates PAE-1-PAE-18

The following compounds were prepared according to the indicated method (Method PAE-A, Method PAE-B, Method PAE-C, Method PAE-D or PAE-E) from the indicated starting materials, unless otherwise described.

Intermediate PAE-1

Boc-D,L-(2-pyridinyl)glycine Ethyl Ester.

Method PAE-A

To a solution of ethyl hydroxyimino-pyridin-2-yl-acetate (7.8 g, 40.15 g) in ethanol (175 mL) and glacial acetic acid (20 mL) was added 5% Pd/C, and the mixture was shaken in a hydrogenation apparatus under an atmosphere of hydrogen at 4.1 bar (45 psig) for 4 h. The mixture was filtered through diatomaceous earth and concentrated in vacuo. The residue was dissolved in THF/$H_2O$ (1/1, 240 mL) and treated with di-tert-butyl dicarbonate (14.23 g, 65.2 mmol) and sodium bicarbonate (27.4 g, 326 mmol). After stirring at room temperature for 2 h, the solution was concentrated in vacuo and the residue was partitioned between EtOAc and water. The organic phase was washed with brine, dried over magnesium sulfate, filtered and concentrated in vacuo. The crude material was purified via chromatography over silica gel, eluting with a stepwise gradient of 10–20% ethyl acetate in dichloromethane to give 8.11 g (72%) of the title compound as a yellow oil.

1H-NMR

IS-MS, m/e 281.1 (M+1)

Intermediate PAE-2

Boc-D,L-(3-pyridinyl)glycine Ethyl Ester.

Prepared from ethyl hydroxyimino-pyridin-3-ylacetate using Method PAE-A.

1H-NMR

IS-MS, m/e 281.1 (M+1)

Intermediate PAE-3

Boc-D,L-(8-quinolinyl)glycine Ethyl Ester.

Method PAE-B

To a stirring solution of ethyl hydroxyimino-quinolin-8-ylacetate (2.4 g, 9.8 mmol) in 50% aq. formic acid (50 mL) at 0° C. was added zinc dust (2 g, 31 mmol). After 1 min, the mixture was filtered through diatomaceous earth and the filtrate was loaded onto an SCX column. After washing the column with methanol, the product was eluted with a 3 to 1 mixture of dichloromethane and (2 N $NH_3$ in methanol). The product containing fractions were combined and concentrated in vacuo to give 2.24 g of light orange oil (IS-MS, m/e 231.0 (M+1)).

The oil (2.14 g, 9.3 mmol) was dissolved in THF (40 mL) and to this stirring solution was added triethylamine (1.4 mL, 10.2 mmol), followed by di-tert-butyl dicarbonate (2.1 g, 9.8 mmol). After 45 min, the solvent was removed in vacuo and the residue was partitioned between ethyl acetate and water. The organic phase was then washed with satd aq. $NaHCO_3$, dried with $Na_2SO_4$, filtered and concentrated in vacuo. The residue was dissolved in a minimum volume of dichloromethane and chromatographed over silica gel, eluting with 5% ethyl acetate in hexanes. The product containing fractions were combined and concentrated to give 2.5 g (81%) of the title compound.

1H-NMR

IS-MS, m/e 331.0 (M+1)

Intermediate PAE-4

Boc-D,L-(5-quinolinyl)glycine Ethyl Ester

Prepared from ethyl hydroxyimino-quinolin-5-ylacetate using Method PAE-B.

1H-NMR

IS-MS, m/e 331.0 (M+1)

Intermediate PAE-5

N-4-Methoxybenzoyl-N-2,4-dimethoxybenzyl-D,L-(2-trifluoromethylphenyl)glycine Methyl Ester.

Method PAE-C

To 2-trifluoromethylbenzaldehyde (1 g, 5.7 mmol) with stirring was added 2,4-dimethoxybenzylamine (0.86 mL, 5.7 mmol) and methanol (2 mL). After 5 min, the solution was diluted with toluene 100 mL and concentrated in vacuo (twice). The residue was then dissolved in anhydrous methanol (12 mL) and 1,1-dimethyl-2-(methoxycarbonyloxy) ethyl isonitrile [Tetrahedron, 55 (1999) 7411–74201 (0.9 g, 5.7 mmol) was added, followed by 4-methoxybenzoic acid (0.87 g, 5.7 mmol). After stirring for 72 h, the solvent was removed in vacuo and the residue was chromatographed over silica gel, eluting with a step gradient of 30% ethyl acetate in hexanes through 50% ethyl acetate in hexanes. The product containing fractions were combined and concentrated in vacuo; and then the residue was dissolved in ethyl acetate, washed with satd aq. $NaHCO_3$, dried with $Na_2SO_4$, filtered and concentrated to give 1.76 g (48%) of thick oil (NMR, IS-MS, m/e 633.0 (M+1)). The oil (0.5 g, 0.79 mmol) was then dissolved in toluene (5 mL) and concentrated in vacuo (twice) to give a white foam. The residue was then dissolved in THF (3 mL) and potassium tert-butoxide (0.11L g, 0.95 mmol) was added. After 15 min, 12 N HCl (0.079 mL, 0.95 mmol) was added and the solution was allowed to stand overnight in the refrigerator. The next morning, the solvent was removed and the residue was chromatographed over silica gel, eluting with 30% ethyl acetate in hexanes. The product containing fractions were combined and concentrated to give 0.32 g (79%) of the title compound.

1H-NMR

IS-MS, m/e 518.0 (M+1)

Intermediate PAE-6

BOC-D,L-(5-thiazolyl)glycine Ethyl Ester.

To a r.b. flask (250 cm$^3$), D,L-(5-thiazolyl)glycine ethyl ester (4.60 g, 24.7 mmol) was added to tetrahydrofuran (c.a. 100 cm$^3$) with stirring to give a yellow solution. BOC anhydride (5.439 g, 24.948 mmol) and triethyl amine (3.79 cm$^3$, 2.75 g, 27.17 mmol) were then added with stirring for 1 hour. Reaction monitored by TLC (60% hexane/ethyl acetate; s.m. r.f 0.05, prod. r.f. 0.5.). The reaction concentrated in vacuo and product taken up in ethyl acetate (c.a. 150 cm$^3$), washed with 5% hydrochloric acid solution (c.a. 30 cm$^3$), and saturated bicarbonate (ca. 30 cm$^3$). Ethyl acetate layer was dried over magnesium sulphate and evaporated to dryness to give an orange oil (7.42 g, ~24.70 mmol) [~100% Yield].

$^1$H NMR (CDCl$_3$); 1.30 (3H, t), 1.48 (9H, s), 4.28 (2H, q), 5.68 (1H, br.), 7.88 (1H, s), 8.78 (1H, s).

D,L-(5-Thiazolyl)glycine Ethyl Ester.

To a r.b. flask (250 cm$^3$), was added 5-thiazolyloximinoacetic acid ethyl ester (6.37 g, 31.825 mmol) to ethanol (c.a. 80 cm$^3$) with stirring. 50% Formic acid solution (50 cm$^3$) was added with zinc dust (5.10 g, 81.83 mmol) and allowed to stir overnight. Reaction monitored by TLC (60% hexane/ethyl acetate; s.m. r.f 0.3, prod. r.f. 0.05.). Reaction solution filtered over diatomaceous earth and filtrate concentrated in vacuo. This was basified to pH 9 with anhydrous potassium carbonate and product taken up in 3:1 chloroform/isopropanol solution (c.a. 200 cm$^3$). This was washed with saturated bicarbonate (c.a. 50 cm$^3$), dried over magnesium sulphate and concentrated in vacuo to give a brown oil (4.60 g, 24.70 mmol) [78% Yield].

1H NMR (CDCl$_3$); 1.25 (3H, t), 1.95 (2H, br.), 4.22 (2H, q), 4.85 (1H, s), 7.80 (1H, s), 8.70 (1H, s).

Intermediate PAE-7

N-Boc-D,L-(4-thiazolyl)glycine ethyl ester

To a solution of D,L-(4-thiazolyl)glycine ethyl ester (0.460 g, 2.470 mmol) in tetrahydrofuran (20 cm$^3$), was added di-tert-butyl dicarbonate (0.530 g, 2.470 mmol) and triethylamine (0.344 cm$^3$, 2.470 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield an orange oil (0.709 g, 2.477 mmol) [-100% yield].

$^1$H NMR (CDCl$_3$) 1.15 (3H, t), 1.35 (9H, s), 4.1 (2H, m), 5.45 (1H, d), 5.75 (1H, d), 7.3 (1H, d), 8.7 (1H, d).

D,L-(4-Thiazolyl)glycine Ethyl Ester.

This was prepared from ethyl-α-oximino-thiazole-4-acetate (0.60 g) using the method of Hatanaka et al. (*Journal of Medicinal Chemistry*, 1973, 16(9), 978–984) to yield the titled compound (0.46 g).

$^1$H NMR (CDCl$_3$) 1.25 (3H, t), 1.8–2.3 (2H, br.), 4.1 (2H, m), 4.75 (1H, s), 7.25 (1H, d), 8.7 (1H, d).

Intermediate PAE-8

N-Boc-D,L-(2-methylthiazol-4-yl)glycine Ethyl Ester

To a solution of D,L-(2-methylthiazol-4-yl)glycine ethyl ester (0.397 g, 1.982 mmol) in tetrahydrofuran (20 cm$^3$), was added di-tert-butyl dicarbonate (0.475 g, 2.180 mmol) and triethylamine (0.304 cm$^3$, 2.180 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield a yellow oil (0.654 g, 2.177 mmol) [~100% yield].

$^1$H NMR (CDCl$_3$) 1.1 (3H, s), 1.35 (9H, s), 2.6 (3H, s), 4.15 (3H, m), 5.3 (1H, d), 5.7 (1H, s), 7.0 (1H, s).

D,L-(2-Methylthiazol-4-yl)glycine Ethyl Ester.

This was prepared from ethyl-α-oximino-2-methylthiazole-4-acetate (0.62 g) using the method of Hatanaka et al. (*Journal of Medicinal Chemistry*, 1973, 16(9), 978–984) to yield the titled compound (0.40 g).

$^1$H NMR (CDCl$_3$) 1.15 (3H, t), 1.95 (2H, br.), 2.6 (3H, s), 4.15 (2H, m), 4.65 (1H, s), 6.95 (1H, s).

Intermediate PAE-9

Boc-R-(4-Hydroxyphenyl)glycine Methyl Ester

To a stirred mixture of R-(4-hydroxyphenyl)glycine methyl ester hydrochloride (14 g) and sodium bicarbonate (11.7 g) in THF (150 mL) and water (50 mL), was added in one portion, di-t-butyl dicarbonate (15.9 g). The mixture was stirred rapidly to allow thorough mixing for 4 h. Hexane (75 mL) was added and the organic layer separated and washed with satd sodium bicarbonate solution, then brine and then dried with magnesium sulphate. The drying agents was filtered off and washed with a little THF and evaporated to dryness, finishing with a high vacuum pump to remove the last traces of di-t-butyl dicarbonate. Yield 19.7 g, 96%.

$^1$H NMR

R-(4-Hydroxyphenyl)glycine Methyl Ester Hydrochloride.

To a dry 250 mL three necked round bottom flask, equipped with a low temperature thermometer, a septum for nitrogen coverage and another for introduction of thionyl chloride by syringe, was added R-4-hydroxyphenylglycine (12.5 g) and dry methanol (24 mL). The mixture was stirred (magnetic stirrer) and cooled to an internal temperature of −20° C. using cardice/acetone. Using a syringe, thionyl chloride was added dropwise to the cooled mixture over a period of 10 min. (Care: the reaction of thionyl chloride with methanol is very exothermic and rate of addition should be such that the thionyl chloride is efficiently stirred into the mixture and that the temperature does not rise above −20° C. Once the addition was complete the mixture was allowed to warm to room temperature overnight (16–18 h). Dry ether (150 mL) was added and the white ppt. that formed was filtered off, washed with a little more ether and dried. Yield 15.5 g, 95%.

$^1$H NMR

Intermediate PAE-10

Boc-R-(4-Trifluoromethanesulphonyloxyphenyl)glycine Methyl Ester Hydrochloride.

To a stirred solution of Boc-R-(4-hydroxyphenyl)glycine methyl ester (19 g) in dichloromethane (400 mL) was added 2,6-lutidine (9.44 mL) and 4-dimethylaminopyridine (1.65 g) and the mixture cooled in an ice bath. Trifluoromethananesulphonic anhydride (13.74 mL) was added over a period of 5 min, and then the reaction left to warm to room temperature over 4 h. The organic solution was washed with water (2×150 mL), 1 N HCl (2×150 mL), and then saturated sodium bicarbonate (150 mL). The organics were dried with magnesium sulphate and then evaporated to an oil. The mixture was purified using flash chromatography (SiO$_2$ 250 g, eluting with 1:1 hexane/dichloromethane and then neat dichloromethane). Pure product fractions were combined and evaporated, finishing with a high vacuum pump to remove all traces of solvent, to give a white solid, 19 g, 77%.
$^1$H NMR Intermediate PAE-11

Boc-R-(4-Methoxycarbonylphenyl) glycine Methyl Ester.

Method PAE-D

Boc-R-4-trifluoromethanesulphonyloxyphenylglycine methyl ester (15 g), methanol (32.6 mL), bis-1,3-diphenylphosphinylpropane (448 mg), palladium (II) acetate (255 mg), triethylamine (10.2 mL) and dimethylformamide (72 mL) were placed in the glass liner of pressure (Parr) reactor and the reactor assembled. The vessel was pressurised to −0.68 bar (10 psig) with nitrogen and the gas released (repeated five times to remove all oxygen from the system). Carbon monoxide gas was then carefully introduced (use extreme care the gas cylinder is pressurised to far beyond the bursting disc pressure of the Parr, ideally use a pressure regulator to reduce the pressure to ~6.8 bar, 100 psig) to ~1.4 bar (20 psig) and released three times (into the back of a fume hood). Carbon monoxide was then added to ~6.8 bar (100 psig) and the stirrer started. The vessel was slowly heated to 65° C. internal temperature and then stirred at 65° C. overnight. (At the early stages more carbon monoxide was added to maintain ~6.8 bar, 100 psig.) A sample was removed after 18 h and examined by tlc. When complete, the reaction was cooled to ~30° C., the gas released and the vessel flushed five times with nitrogen as before. The reaction mixture was partitioned between ethyl acetate and water, and the organic layer washed with 1 M hydrochloric acid and then saturated sodium bicarbonate. The solution was dried with MgSO$_4$ and evaporated. Flash chromatography of the resulting oil gave the product, pure by tlc, 10.6 g, 90%.
$^1$H NMR Intermediate PAE-12

Boc-R-(4-Benzy:Loxycarbonylphenyl)glycine Methyl Ester

Prepared from Boc-R-4-trifluoromethanesulphonyloxy phenylglycine methyl ester and benzyl alcohol using Method PAE-D.
$^1$H NMR Intermediate PAE-13

Boc-R-(4-Carboxyphenyl)glycine Methyl Ester.

Boc-R-(4-benzyloxycarbonylphenyl)glycine methyl ester (500 mg) was dissolved in THF containing Pd/C 10% (100 mg) and hydrogenated at 1 atm for 2 h. Removal of the catalyst by filtration and evaporation of solvent gave Boc-R-(4-carboxyphenyl)glycine methyl ester (330 mg, 87%).
$^1$H NMR Intermediate PAE-14

Boc-R-(4-carboxamidophenyl)glycine Methyl Ester.

Method PAE-E

To a solution of Boc-R-(4-carboxyphenyl)glycine methyl ester (3.5 g) in DMF (30 mL) was added EDCI (2.60 g, 1.36 mmol) and HOBt (1.4 g, 10.4 mmol), and the mixture stirred for 10 min before cooling in a ice bath and bubbling in ammonia gas for 5 min. The mixture was stirred for 2 h at room temperature and then diluted with ethyl acetate and washed with water. The aqueous solution was extracted with a little ethyl acetate and the combined organics washed with brine. The organic solution was evaporated to an oil which was purified by flash chromatography (SiO$_2$—dichloromethane/ethyl acetate 0–25%) to give Boc-R-(4-carboxamidophenyl)glycine methyl ester (1.7 g, 48%).
$^1$H NMR Intermediate PAE-15

Boc-R-(4-methylcarboxamidophenyl)glycine Methyl Ester.

Prepared from Boc-R-(4-carboxyphenyl)glycine methyl ester and methylamine using Method PAE-E.
$^1$H NMR Intermediate PAE-16

N-4-Methoxybenzoyl-N-2,4-dimethoxybenzyl-D,L-(quinolin-4-yl)glycine Methyl Ester.

Prepared from quinoline-4-carboxaldehyde using Method PAE-C.
$^1$H NMR

Intermediate PAE-17

Ethyl Boc-D,L-thiazol-2-ylglycine.

Prepared from ethyl hydroxyimino-thiazol-2-ylacetate using Method PAE-B. In this case, reaction with Zn/formic acid was conducted over 15 min.
$^1$NMR IS-MS, m/e 287.0 (M+1)

Intermediate P.AE-18

Ethyl Boc-D,L-isoquinolin-8-ylglycine.

Prepared from ethyl hydroxyimino-isoquinolin-8-ylacetate using Method PAE-B. In this case, reaction with Zn/formic acid was conducted over 30 min, followed by concentration and partitioning of the residue between 3/1 chloroform/isopropanol and satd aq. NaHCO$_3$. The Boc protection was carried out as previously described. Purification was performed using silica gel chromatography (Biotage Quad System) eluting with 10% ethyl acetate in methylene chloride.
$^1$NMR IS-MS, m/e 331.0 (M+1)

| Analysis for $C_{18}H_{22}N_2O_4$: | |
|---|---|
| Calcd: | C, 65.44; H, 6.71; N, 8.48; |
| Found: | C, 65.05; H, 6.67; N, 8.49. |

Preparation of Intermediates PAA-1-PAA-28

The following compounds were prepared according to the indicated method (Method PAA-A, Method PAA-B, Method PAA-C, Method PAA-D, Method PAA-E or Method PAA-F) from the indicated starting materials, unless otherwise described.

Intermediate PAA-1

Boc-D,L-(2-chlorophenyl)glycine.

Method PAA-A

2-Chlorobenzaldehyde (20 mmol, 2.252 mL) and 2,4-dimethoxybenzylamine (20 mmol, 3.004 mL) were added together and stirred for 2 hours. DCM (5 mL) was added and any water separated and removed. tert-Butyl isonitrile (20 mmol, 2.262 mL) was added and stirred for 10 min, followed by acetic acid (20 mmol, 1.145 mL). Stirring was continued for 3 days. The reaction mixture was then treated with TFA (30 mL) and triethylsilane (5 mL). After 3 h the mixture was evaporated to dryness, 6 M HCl (100 mL) added, and the whole refluxed overnight at 130° C., stirring rapidly. The mixture was allowed to cool and extracted with EtOAc (50 mL×2); the aqueous fraction was evaporated to dryness and treated with 2 M NaOH solution. The mixture was extracted with EtOAc (50 mL×2); excess boc anhydride (5.2 g) in dioxane (20 mL) was added to the aqueous fraction and stirred overnight. The mixture was extracted with diethyl ether (100 mL×2), acidified to pH 1 (conc HCl) and extracted with EtOAc (50 mL×2). The combined organic fractions were washed with water and evaporated to dryness under high vacuum. The product Boc-2-chlorophenylglycine (4.252 g, 74.5%)

$^1$H NMR (CD$_3$CN/D$_2$O) 7.3 (4H, m); 5.5 (1H, s); 1.3 (9H, s). MS 286 (M+1)

Intermediate PAA-1'
(R)-Benzyloxycarbonyl-(2-chlorophenyl)glycine.

Prepared from 2-chlorostyrene using the method of Sharpless et al J.A.C.S. (1998) Vol120 No.6 1207–1217.

Intermediate PAA-1, alternative preparation
Boc-D,L-(2-chlorophenyl)glycine.

Prepared from 2-chlorobenzaldehyde using method PAA-F. In this case, the reaction temperature was not controlled upon addition of 2-chlorobenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 284 (M−1)

Intermediate PAA-2
Boc-D,L-(3-fluorophenyl)glycine.

Prepared from 3-fluorobenzaldehyde using Method PAA-A.

$^1$H NMR (CD$_3$CN/D$_2$O) 7.3 (1H, m), 7.1(3H, m); 5.2 (1H, s); 1.3 (9H, s). MS 270 (M+1)

Intermediate PAA-3
Boc-D,L-(4-fluorophenyl)glycine.

Prepared from 4-fluorobenzaldehyde using Method PAA-A.

$^1$H NMR (CD$_3$CN/D$_2$O) 7.3 (2H, m); 6.9 (2H, m), 5.0 (1H, s); 1.3 (9H, s). MS 270 (M+1)

Intermediate PAA-4
Boc-D,L-(2-methylphenyl)glycine.

Prepared from 2-methylbenzaldehyde using Method PAA-A.

$^1$H NMR (CD$_3$CN/D$_2$O) 7.3 (4H, m); 5.5 (1H, s); 2.5 (3H, s); 1.3 (9H, s). MS 266 (M+1)

Intermediate PAA-5
Boc-D,L-(3-thienyl)glycine.

Prepared from 3-thiophenecarboxaldehyde using Method PAA-A.

$^1$H NMR (CD$_3$CN/D$_2$O) 7.5 (2H, m); 7.1 (1H, d); 5.3 (1H, s); 1.3 (9H, s). MS 258 (M+1)

Intermediate PAA-6
Boc-D,L-(2-fluorophenyl)glycine.

Was obtained by treating D,L-2-fluorophenylglycine (Aldrich) with Boc anhydride (1.1 eq) and 2 M NaOH (1 eq) in ethanol. Aqueous work up as described above yielded the protected amino acid.

$^1$H NMR

Intermediate PAA-7
Boc-D,L-(2-methoxyphenyl)glycine.

Prepared from 2-methoxybenzaldehyde using Method PAA-A.

$^1$H NMR

Intermediate PAA-7, alternative preparation
Boc-D,L-(2-methoxyphenyl)glycine.

Prepared from 2-methoxybenzaldehyde using method PAA-F. In this case, the reaction was cooled to 0° C. before addition of 2-methoxybenzaldehyde and was then allowed to stir at room temperature overnight. Extraction of the intermediate aminonitrile was performed with ethyl ether in place of ethyl acetate and was further purified by addition of 1 M HCl in ethyl ether followed by filtration of the crystalline hydrochloride salt. BOC protection of the amino acid was performed from 0° C. to room temperature over a period of three hours, and the final extraction was performed with dichloromethane in place of ethyl ether.

$^1$H-NMR
IS-MS m/e 280.1 (M−1)

| Analysis for C$_{14}$H$_{19}$NO$_5$ | |
| --- | --- |
| Calcd: | C, 59.78; H, 6.81; N, 4.98; |
| Found: | C, 59.68; H, 6.78; N, 4.95. |

Intermediate PAA-8
Boc-D,L-(2-trifluoromethyl)phenylglycine.

Prepared from 2-trifluoromethylbenzaldehyde using Method PAA-A.

$^1$H NMR

Intermediate PAA-8, alternative preparation
Boc-D,L-(2-trifluoromethylphenyl)glycine.

Prepared from 2-trifluoromethylbenzaldehyde using method PAA-F. In this case, the reaction temperature was not controlled upon addition of 2-trifluoromethylbenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 318 (M−1)

Intermediate PAA-9
Boc-D,L-(8-quinolinyl)glycine.

Method PAA-B

To a stirring solution of Boc-D,L-(8-quinolinyl)glycine ethyl ester (2.29 g, 6.93 mmol) in 1,4-dioxane (11 mL) was added a solution of LiOH hydrate (0.32 g, 7.6 mmol) in water. After 2 h, the solvents were removed in vacuo and the residue was dissolved in water and washed with diethyl ether. The aqueous phase was then acidified to pH 3 with solid citric acid and extracted with ethyl acetate. The organic phase was then washed with brine, dried with Na$_2$SO$_4$, filtered and concentrated to give 2.06 g (98%) of the title compound.

$^1$H-NMR
IS-MS, m/e 303.0 (M+1)

Intermediate PAA-10
Boc-D,L-(5-quinolinyl)glycine.

Prepared from Boc-D,L-(5-quinolinyl)glycine ethyl ester using Method PAA-B.

$^1$H-NMR
IS-MS, m/e 303.0 (M+1)

Intermediate PAA-11
Boc-D-(3-bromophenyl)glycine.

Prepared from R-3-bromo-(1-t-butoxycarbonylamino-2-hydroxyethyl)benzene using Method PAA-C.

Melting Point=130–132° C. with decomposition
$^1$H NMR (CDCl$_3$)
API-MS, m/e 286 (M-CH$_2$H+1)

Intermediate PAA-12
Boc-D-(3-methoxycarbonylphenyl)glycine.

Method PAA-C

To a stirred solution of R-3-methoxycarbonyl-(1-t-butoxycarbonylamino-2-hydroxyethyl)benzene (338 mg, 1.14 mmol) in acetone (7.2 mL) was added 5% NaHCO$_3$ (3 mL). The reaction mixture was cooled to 0° C. To the stirred suspension was added KBr (14 mg, 0.12 mmol), TEMPO (181 mg, 1.16 mmol) and NaOCl dropwise (2.81 mL, 5.25%). After 1 h at 0° C., TEMPO (136 mg, 0.88 mmol) and NaOCl (1.09 mL; 5.25%) were added. The reaction was stirred for a further 0.5 h at 0° C. and 5% NaHCO$_3$ (4.3 mL) was added. The reaction was allowed to warm to room temperature overnight. Acetone was removed under vacuum and the crude product was partitioned between ethyl acetate and water. The aqueous layer was washed with ethyl acetate (2×) and acidified to pH 5 with 10% citric acid and extracted with ethyl acetate (4×). The combined organic extracts were dried over MgSO$_4$. Removal of solvent under vacuum gave the product (305 mg, 86%).

$^1$H NMR (CDCl$_3$)
API-MS, m/e=254 (M-C$_4$H$_9$+1)

Intermediate PAA-13
Boc-D-(3-cyanophenyl)glycine.

Prepared from R-3-cyano-(1-t-butoxycarbonylamino-2-hydroxyethyl)benzene using Method PAA-C.
$^1$H NMR (CDCl$_3$)
API-MS, m/e=221 (M-C$_4$H$_9$+1)

Intermediate PAA-14
Boc-D-(3-ethanesulfonylaminophenyl)glycine.

To a stirring solution of 3-(ethanesulfonylaminophenyl) glycine (20 g, 77.43 mmol) and sodium carbonate (8.2 g, 77.43 mmol) in 3:1 THF:water (200 mL) at 0° C., was added di-tert-butyl dicarbonate (18.5 g, 85.17 mmol). After stirring for 30 min, the cold bath was removed; and after an additional 30 min at room temperature the solvent was removed; and the residue was partitioned between ethyl acetate and water. The aqueous layer was acidified to pH 2 with KHSO$_4$ and extracted twice with ethyl acetate. The combined ethyl acetate extracts were washed with water, dried with Na$_2$SO$_4$, filtered and concentrated in vacuo to give 17.51 g (63%) of a white solid.

1H-NMR
IS-MS, m/e 357.0 (M-1)

Intermediate PAA-1S
N-Boc-D,L-(5-thiazolyl)glycine.

To a r.b. flask (150 cm$^3$), was added Boc-D,L-(5-thiazolyl)glycine ethyl ester (7.00 g, 24.70 mmol) to ethanol (c.a. 100 cm$^3$) with stirring. 2 M Sodium hydroxide solution (25 cm$^3$, 50 mmol) was added and allowed to stir for 1 h. Reaction monitored by TLC (60% hexane/ethyl acetate; s.m. r.f 0.5, prod. r.f. 0.). Reaction concentrated in vacuo and product taken up in saturated bicarbonate (c.a. 50 cm$^3$) and washed with ethyl acetate (c.a. 30 cm$^3$). Aqueous layer was acidified to pH 2 with concentrated hydrochloric acid and product extracted with 3:1 chloroform/isopropanol solution (c.a. 3×60 cm$^3$). The organic layer was dried over magnesium sulphate and evaporated to dryness to give an orange solid (4.47 g, 17.30 mmol) [74% Yield].

$^1$H NMR (CDCl$_3$); 1.35 (9H, s), 5.60 (1H, d), 5.83 (1H, d), 7.88 (1H, s), 8.80 (1H, s).

Intermediate PAA-16
N-Boc-D,L-(4-thiazolyl)glycine.

Method PAA-D

To a solution of N-Boc-D,L-(4-thiazolyl)glycine ethyl ester (0.700 g, 2.470 mmol) in methanol (c.a. 15 cm$^3$), was added 2 M sodium hydroxide (2.47 cm$^3$, 4.940 mmol) and allowed to stir for 90 min. The solution was concentrated in vacuo and taken up in water (c.a. 20 cm$^3$). The aqueous solution was washed with ethyl acetate (c.a. 20 cm$^3$), and then acidified to pH 2 with 5% hydrochloric acid solution (c.a. 50 cm$^3$). The product was extracted with ethyl acetate (c.a. 3×30 cm$^3$), dried over magnesium sulphate, and concentrated in vacuo to yield a pale yellow oil (0.582 g, 2.254 mmol) [91% yield].

$^1$H NMR (CDCl$_3$) 1.35 (9H, s), 5.5 (1H, d), 5.8 (1H, d), 7.35 (1H, d), 8.75 (1H, d), 9.8–10.2 (1H, br.).

Intermediate PAA-17
N-Boc-D,L-(2-methylthiazol-4-yl) glycine.

Prepared from N-Boc-D,L-(2-methylthiazol-4-yl)glycine ethyl ester using Method PAA-D.
$^1$H NMR (CDCl$_3$) 1.35 (9H, s), 2.6 (3H, s), 5.4 (1H, d), 5.9 (1H, s), 7.1 (1H, s).

Intermediate PAA-18
N-Boc-D,L-(2-Benzyloxycarbonylamino-4-thiazolyl) glycine.

Is prepared from D,L-(2-benzyloxycarbonylamino-4-thiazolyl)glycine. The benzyloxycarbonyl protecting group is removed from the thiazolyl amino group at a convenient point in the preparation of a final compound using a conventional method, such as, for example, heating a solution of an intermediate in HBr/acetic acid at 60° C., followed by evaporation and a conventional isolation, such as by using SCX ion exchange chromatography.

D,L-(2-Benzyloxycarbonylamino-4-thiazolyl)glycine.
Was prepared by the method of Hardy, K.; Harrington, F. and Stachulski, A.—J. Chem. Soc. Perkin Trans I (1984) 1227–1235.

Intermediate PAA-19
Boc-R-(4-methoxycarbonylphenyl)glycine.

To a solution of Boc-R-(4-methoxycarbonylphenyl) glycine methyl ester (692 mg) in THF (10 mL) was added a solution of lithium hydroxide hydrate (90 mg) in water (7 mL). The mixture immediately became cloudy and over 15 min cleared. After 30 min, tlc showed the reaction to be complete. Ethyl acetate (20 mL) and water (20 mL) were added, and the aqueous layer separated. The aqueous solution was acidified with 2 M hydrochloric acid and extracted with ethyl acetate (3×20 mL). The organic solution was then washed with water×2 and brine×2, dried with MgSO$_4$ and evaporated to give the monoester (650 mg, 98%), pure by tlc.

$^1$H NMR

Intermediate PAA-20
Boc-R-(4-Methoxyphenyl)glycine.

Boc-R-(4-hydroxyphenyl)glycine methyl ester was converted to Boc-R-4-methoxyphenylglycine using the alkylation method described by Basak et al. (Tetrahedron Lett. 1998, 39 (27), 4883–4886), followed by hydrolysis of the methyl ester with lithium hydroxide in aqueous THF.

$^1$H NMR

Intermediate PAA-21
N-4-Methoxybenzoyl-N-2,4-dimethoxybenzyl-D,L-(2-trifluoromethylphenyl)glycine.

Prepared from N-4-methoxybenzoyl-N-2,4-dimethoxybenzyl-D,L-(2-trifluoromethylphenyl)glycine methyl ester using Method PAA-B (3 equivalents of LiOH hydrate).

¹H NMR
IS-MS, m/e 503.9 (m+1)
Intermediate PAA-22
N-4-Methoxybenzoyl-N-2,4-dimethoxybenzyl-D,L-(thien-2-yl)glycine.

Method PAA-E

To a solution of 2-thiopheneboronic acid (5.0 g, 39.0 mmol, 1 equiv) in 275 mL of methylene chloride at rt was added 3,4-dimethoxybenzylamine (5.89 mL, 39.0 mmol, 1 equiv) followed by glyoxylic acid monohydrate 3.6 g, 39 mmol, 1 eguiv). The reaction was allowed to stir for 56 hours at rt after which time the resultant precipitate was filtered and washed with methylene chloride to afford 9.3 g (78%) of N-2,4-dimethoxybenzyl-D,L-(thien-2-yl)glycine as an off-white solid (IS-MS, m/e 308 (m+1)).

A portion of the solid (5.0 g, 16.3 mmol, 1 equiv.) was dissolved in acetone (20 mL) and 1 N sodium hydroxide (20 mL) at rt. To this solution was simultaneously added anisoyl chloride (2.78 g, 16.3 mmol, 1 equiv.) in 20 mL of acetone and 2 N sodium hydroxide in dropwise fashion. After stirring at rt for 1 h, the reaction was cooled to 0° C. and was acidified to pH 2–3. Diethyl ether was added and the product was extracted into the organic phase. The combined organic phases were washed with brine, dried over sodium sulfate, filtered, and concentrated to afford 5.1 g (71%) of the titled compound as a white solid.

IS-MS, m/e 440 (m+1).
Intermediate PAA-23
N-Boc-N-2,4-dimethoxybenzyl-D,L-(thien-2-yl)glycine.

To a solution of N-2,4-dimethoxybenzyl-D,L-(thien-2-yl)glycine (1.0 g, 3.2 mmol, 1 equiv) in 6 mL of acetone and 6 mL of water at rt was added triethylamine (0.97 mL, 7.0 mmol, 2.1 equiv.) followed by addition of 2-(tert-butoxycarbonyloxyimino)-2-phenylacetonitrile (BOC—ON) (0.76 g, 3.1 mmol, 0.95 equiv). After stirring at rt overnight, the reaction was diluted with water and washed with ether. The aqueous phase was then acidified with 0.5 M citric acid and the product was extracted into diethyl ether. The combined organic phases were washed with brine, dried over sodium sulfate, filtered, and concentrated to afford 0.38 g (29%) of the titled compound as a crude yellow oil.

IS-MS, m/e 408 (m+1).
Intermediate PAA-24
Boc-D,L-isoquinolin-8-ylglycine.

Prepared from ethyl Boc-D,L-isoquinolin-8-ylglycine using Method PAA-B. The product was precipitated from a basic aqueous solution by adjusting the pH to 3 with solid citric acid.

¹NMR
IS-MS, m/e 303.0 (M+1)

| Analysis for $C_{16}H_{18}N_2O_4 \cdot 0.5\ H_2O$: | |
|---|---|
| Calcd: | C, 61.73; H, 6.15; N, 9.00; |
| Found: | C, 61.62; H, 5.66; N, 8.84. |

Intermediate PAA-25
Boc-D,L-Naphthalen-1-ylglycine.

Method PAA-F
Part A: D,L-Naphthalen-1-ylglycine Hydrochloride.

To a solution of sodium cyamide (10.0 g, 0.22 mmol) in 40 mL of water was added ammonium chloride (11.4 g, 0.22 mmol), and the mixture was stirred until dissolution was complete. A solution of 1-naphthaldehyde (31.0 g, 0.22 mmol) in 40 mL of methanol was then added and the resultant mixture was allowed to stir at room temperature for two days. An additional 150 mL of water was then added and the crude product was extracted into EtOAc. The combined organic layers were washed with water, dried over $Na_2SO_4$, filtered and concentrated to afford a crude oil. The crude residue was chromatographed over silica gel, eluting with with 10:1 EtOAc:$CH_2Cl_2$, to give 35 g of a light brown oil. This material was then dissolved in 250 mL of 5 N HCl and was heated to reflux for 9 h. The reaction was allowed to cool to room temperature and the product was allowed to crystallize overnight. Filtration of the mixture afforded 13.6 g (29%) of the title compound as light brown crystals.

¹NMR
IS-MS, m/e 201.9 (M+1)
Part B: Boc-D,L-Naphthalen-1-ylglycine.

To a solution of D,L-naphthalen-1-ylglycine hydrochloride (13.6 g, 57.2 mmol) and 2 N sodium hydroxide (57 mL, 115 mmol) in 120 mL of 1,4-dioxane and 60 mL of water was added $(BOC)_2°$ (15 g, 69 mmol.). The reaction was allowed to stir at room temperature for 3 h after which time the solution was brought to pH 5 by addition of 1 N sulfuric acid. The product was then extracted into EtOAc; and the combined organic extracts were dried over $Na_2SO_4$, filtered, and concentrated to give 14 g (81%) of the title compound as a light brown foam.

¹NMR
IS-MS, m/e 300.1 (M−1)
Intermediate PAA-26
Boc-D,L-(2-methylthiophenyl)glycine.

To a solution of 2-(methylthio)benzaldehyde (15 g, 98.7 mmol) in 100 mL of ethanol was added ammonium carbonate (23.1 g, 296 mmol) and a solution of potassium cyamide (12 g, 148 mmol) in 100 mL water. The reaction was heated and stirred at 70° C. for 3 h after which time the reaction was concentrated under reduced pressure. The product was extracted into ethyl acetate; and the combined organic phases were washed with brine, dried over $Na_2SO_4$, filtered and concentrated. The resultant crude residue was taken up in 70 mL of ethyl acetate, and 70 mL of 5 N sodium hydroxide was added. The reaction was heated to reflux for three days after which time the ethyl acetate was removed under reduced pressure. To the aqueous mixture was sequentially added 100 mL of dioxane, $Boc_2O$ (42 g, 192 mmol), and 100 mL of 2.5 N sodium hydroxide. The reaction was then heated at reflux for 48 h. After cooling to room temperature, the reaction was diluted with water and the aqueous phase was washed with ethyl ether. The aqueous layer was then acidified to pH 2 and the product was extracted into ethyl acetate. The combined organic extracts were washed with brine, dried over $MgSO_4$, filtered, and concentrated to afford 21.7 g of a crude residue. Purification by silica gel chromatography (gradient elution, 97:2:1 to 95:4:1 dichloromethane:methanol:acetic acid) provided 5.0 g (17%) of the title compound.

¹H-NMR
ES-MS m/e 296 (M−1)
Intermediate PAA-27
Boc-D,L-(2-methylsulfonylphenyl)glycine.

To a solution of boc-D,L-(2-methylthiophenyl)glycine (4.5 g, 15.2 mmol) in 75 mL of methanol was added a solution of oxone (14 g, 23 mmol) in water. The reaction was stirred at room temperature for 2 h after which time the methanol was removed under reduced pressure. The product was extracted into ethyl acetate and the combined organic layers were washed with brine, dried over $MgSO_4$, filtered, and concentrated to afford 4.35 g (87%) of the title compound.

¹H-NMR
ES-MS m/e 230(M+1-C₅H₉O₂)
Intermediate PAA-28
Boc-D,L-(benzo[b]thiophen-3-yl)glycine.
May be prepared by the method of Kukolja, S. et al. *J. Med. Chem.* 1985, 28, 1886–1896.

Preparation of Intermediates A-1-A-12

The following compounds were prepared according to the indicated method (Method A—A or Method A-B) from the indicated starting materials, unless otherwise described.
Intermediate A-1
1-[2-(4-Pyridinyl)ethyl]piperazine hydrochloride.

Method A—A
A. 1-Boc-piperazine (30 g, 285 mmol), 4-vinylpyridine (40 g, 216 mmol) and acetic acid (12.9 g, 215 mmol) were mixed in ethanol (400 mL) and heated to reflux for 18 h. The mixture was cooled to room temperature and concentrated under vacuum. The residue was dissolved in water and ethyl acetate and neutralized with satd NaHCO₃. The layers were separated. The water layer was extracted with ethyl acetate. The organic layers were combined, washed with brine, dried (Na₂SO₄), filtered and concentrated. The crude product was purified by SiO₂ chromatography to provide 1-Boc-4-[2-(4-pyridinyl)ethyl]piperazine (55.9 g, 87%) as an off white solid.
1H-NMR (CDCl₃)
CI-MS, m/e=292 (M+1)
B. 1-Boc-4-[2-(4-pyridinyl)ethyl]piperazine (25 g, 85.8 mmol) was dissolved in methanol (100 mL) and was cooled to 0° C. Saturated HCl in methanol (100 mL) was added, and the mixture allowed to warm to room temperature for 1 h. The mixture was concentrated under vacuum and provided 1-[2-(4-pyridinyl)ethyl]piperazine hydrochloride (23.8 g, 92%) as a white solid.
1H-NMR (CD₃OD)
CI-MS, m/e=192 (M+1)
Alternatively, 1-Boc-4-[2-(4-pyridinyl)ethyl]piperazine (1.0 g, 3.43 mmol) was dissolved in ethyl ether. Ethyl acetate (15 mL) saturated with HCl was added, and the mixture stirred for 30 min at room temperature. The mixture was concentrated under vacuum and provided 1-[2-(4-pyridinyl)ethyl]piperazine hydrochloride (900 mg, 87%) as a tan solid.
1H-NMR (CD₃OD)
CI-MS, m/e=192 (M+1)
Intermediate A-2
1-[2-(2-Pyridinyl)ethyl]piperazine.
Prepared from Boc-piperazine and 2-vinylpyridine using Method A—A.
1H-NMR (CD₃OD)
CI-MS, m/e=192 (M+1)
Intermediate A-3
1-[2-(2-Pyrazinyl)ethyl]piperazine.
Prepared from Boc-piperazine and 2-vinylpyrazine using Method A—A.
1H-NMR (CD₃OD)
CI-MS, m/e=193 (M+1)
Intermediate A-4
1-[2-(3-Pyridazinyl)ethyl]piperazine.
Prepared from Boc-piperazine and 3-vinylpyridazine (prepared using the method described in *J. Chem. Soc., Chem. Commun.* 1985, 1632–1633) using Method A—A.
1H NMR (CD₃OD)
API-MS, m/e=193 (M+1)
Intermediate A-S
1-[2-(3-Pyridinyl)ethyl]piperazine.

Method A-B
1-Boc-4-[(3-pyridinyl)acetyl]piperazine (8.0 g, 26.2 mmol) was added to a solution of borane-THF (2.0 M in THF, 39.5 mL, 78.6 mmol) in THF (200 mL) at 0° C. The mixture was heated to reflux for 8 h and cooled to room temperature. The excess borane was quenched with methanol and 3 N HCl. The mixture stirred for 3 h at room temperature, and the solvents were removed under vacuum. The crude product was purified by chromatography (SiO₂, 4:1 CH₂Cl₂:CMA) to provide 1-[2-(3-pyridinyl)ethyl]piperazine (2.82 g, 36%) as a light yellow oil.
¹H NMR (CD₃OD)
API-MS, m/e=192 (M+1)
Intermediate A-6
1-[2-(4-Imidazolyl)ethyl]piperazine.
Prepared from 1-Boc-4-[(4-imidazolyl)acetyl]piperazine using Method A-B.
¹H-NMR
IS-MS, m/e 181.2 (M+1)
Intermediate A-7
1-[2-(1-Imidazolyl)ethyl]piperazine.
Prepared from 1-Boc-4-[(1-imidazolyl)acetyl]piperazine using Method A-B.
¹H-NMR
IS-MS, m/e 181.4 (M+1)
Intermediate A-8
1-[2-(1-Pyrazolyl)ethyl]piperazine.
Prepared from 1-Boc-4-[(1-pyrazolyl)acetyl]piperazine using Method A-B.
¹H-NMR
IS-MS, m/e 181.4 (M+1)
Intermediate A-9
1-(2-Thiazol-2-ylethyl)piperazine.
A. A solution of Boc₂O (26 g, 120 mmol) in methylene chloride (50 mL) was slowly added to a solution of ethyl piperazin-1-ylacetate (20 g, 116 mmol) in CH₂Cl₂ (500 mL). The mixture was stirred for 1 h at room temperature. The solvent was removed under vacuum to provide ethyl 4-Boc-piperazin-1-ylacetate (31.9 g, 100%) as a white solid.
¹H NMR (CDCl₃).
CI-MS, m/e=273 (M+1).
B. N-Methoxy-N-methylamine hydrochloride (4.3 g, 44.1 mmol) was dissolved in methylene chloride (25 mL). The solution was cooled to −78° C., and a solution of trimethylaluminum (44.1 mL, 44.1 mmol, 1 M in heptane) was slowly added. The mixture was stirred at 0° C. for 30 min and was allowed to warm to room temperature and stirred for 30 min. The mixture was then cooled to 0° C., and a solution of ethyl 4-Boc-piperazin-1-ylacetate (10 g, 36.8 mmol) was added dropwise. After 15 min, the cold bath was removed and stirring continued overnight. The mixture was diluted with ethyl acetate and water. The layers were separated, and the water layer extracted with ethyl acetate. The organic layers were combined, washed with brine, dried (Na₂SO₄), filtered, and concentrated to provide N-methoxy-N-methyl-4-Boc-piperazin-1-ylacetamide as a light yellow oil (6.02 g, 57%) that solidified upon standing. The product was used without further purification.
¹H NMR (CDCl₃).
CI-MS, m/e=288 (M+1).
C. n-Butyl lithium (1 M in hexanes, 12.2 mL, 12.2 mmol) was slowly added to a solution of 2-bromothiazole (2.0 g, 12.2 mmol) in diethyl ether (50 mL) at −78° C. The mixture stirred at −78° C. for 1 h. Then, a solution of N-methoxy-N-methyl-4-Boc-piperazin-1-ylacetamide (3.0 g, 10.4 mmol) in tetrahydrofuran was slowly added. The mixture was allowed to slowly warm to −20° C. and stirred for 4 h. The mixture was then diluted with water followed by ethyl acetate. The water layer was extracted with ethyl acetate and the organic layers were combined, washed with brine, dried ($Na_2SO_4$), filtered, and concentrated. The crude product was purified by chromatography ($Sio_2$, 20:1–6:1 $CH_2Cl_2$:CMA) to provide 1-Boc-4-(2-oxo-2-thiazol-2-ylethyl)piperazine (2.2 g, 68%) as a colorless oil.

$^1$H NMR ($CDCl_3$).

CI-MS, m/e=312 (M+1).

D. 1-Boc-4-(2-oxo-2-thiazol-2-ylethyl)piperazine (5.0 g, 16.1 mmol) was dissolved in methanol (25 mL). To this solution, magnesium sulfate (2 g) was added, followed by p-tosylhydrazine (3.9 g, 20.2 mmol). The mixture was stirred for 48 h and then filtered, and the filtrate concentrated under vacuum. The residue (6.0 g, about 12 mmol) was redissolved in methanol (120 mL), and sodium triacetoxyborohydride (10.1 g, 48 mmol) was added. The mixture was heated to reflux overnight. The mixture was cooled to 0° C. and concentrated HCl (15 mL) slowly added. The mixture was allowed to warm to room temperature and stirred for 1 h. The mixture was concentrated to half the volume and placed on an SCX column (30 g, pretreated with 5% acetic acid in methanol) and washed with methanol (500 mL). The product was eluted with saturated ammonium hydroxide in methanol (500 mL) and the solvent removed under vacuum. The crude product was then purified by chromatography ($SiO_2$, 12:1–4:1 $CH_2Cl_2$:CMA) to provide 1-(2-thiazol-2-ylethyl)piperazine (1.9 g, 57%).

$^1$H NMR ($CDCl_3$)

CI-MS, m/e=198 (M+1).

Intermediate A-10

1-[2-(2-Benzyloxycarbonylaminothiazol-4-yl)ethyl]piperazine Hydrochloride.

Using methods substantially equivalent to those described in Method A-B, the title compound was prepared from 1-Boc-4-[2-(2-benzyloxycarbonylaminothiazol-4-yl)acetyl]piperazine (85%).

$^1$H NMR ($CD_3OD$).

CI-MS, m/e=347 (M+1).

Intermediate A-1

1-[2-(3-Fluoropyridin-4-yl)ethyl]piperazine Trihydrochloride.

A. n-Butyl lithium (1.8 M in hexanes, 35 mL, 64.4 mmol) was charged to a round bottom flask and diluted with THF (25 mL). The solution was cooled to 0° C., and a solution of N,N-diisopropylamine (9.0 mL, 65 mmol) in THF (25 mL) was slowly added. The mixture was stirred at 0° C. for 20 min and was cooled to −78° C. A solution of 3-fluoropyridine (20 g, 206 mmol) was added dropwise (temperature of mixture kept below −70° C.), resulting in the formation of a red precipitate. The mixture was stirred at −78° C. for 4 h. Ethylene oxide (4.6 M in THF, 67.2 mL, 309 mmol) was slowly added, and the mixture allowed to warm to room temperature overnight. The mixture was diluted with water and $CH_2Cl_2$. The layers were separated, and the water layer extracted with $CH_2Cl_2$. The organic layers were combined, washed with brine, dried ($Na_2SO_4$), filtered, and concentrated to provide a dark brown oil. The residue was purified by chromatography ($SiO_2$, 19:1–6:1 $CH_2Cl_2$:CMA) to provide 3-fluoro-4-(2-hydroxyethyl)pyridine (6.7 g, 23%) as a tan oil.

$^1$H NMR ($CDCl_3$).

CI-MS, m/e=142 (M+1).

B. 3-Fluoro-4-(2-hydroxyethyl)pyridine (4.0 g, 28.3 mmol) and triethylamine (8.3 mL, 60 mmol) were dissolved in $CH_2Cl_2$ (40 mL) and cooled to 0° C. To this solution, methanesulfonyl chloride (2.0 mL, 31.2 mmol) was added dropwise. The mixture stirred at 0° C. for 1 h. The mixture was diluted with water, and the layers separated. The water layer was extracted with $CH_2Cl_2$. The organic layers were combined, washed with brine, dried ($Na_2SO_4$), filtered, and concentrated under vacuum to provide 3-fluoro-4-(2-methanesulfonyloxyethyl)pyridine (5.2 g, 83%) as a pink oil.

$^1$H NMR ($CDCl_3$).

CI-MS, m/e=220 (M+1).

C. 3-Fluoro-4-(2-methanesulfonyloxyethyl)pyridine (5.2 g, 23.7 mmol) was dissolved in DMF (65 mL). 1-Boc-piperazine (8.85 g, 47.4 mmol), $K_2CO_3$ (3.3 g, 23.7 mmol), NaI (3.6 g, 23.7 mmol) and $Cs_2CO_3$ (7.7 g, 23.7 mmol) were added, and the mixture heated to 55° C. for 18 h. The mixture was cooled to room temperature and diluted with water and ethyl acetate. The layers were separated, and the water layer extracted with ethyl acetate. The organic layers were combined, washed with brine, dried ($Na_2SO_4$), filtered, and concentrated under vacuum to provide a solution of product and DMF. The residue was dissolved in diethyl ether and water. The layers were separated, and the water layer extracted with diethyl ether. The organic layers were combined, washed with brine, dried ($Na_2SO_4$), filtered, and concentrated under vacuum. The crude product was purified by chromatography ($SiO_2$, 15:1–6:1 $CH_2Cl_2$:CMA) to give 1-Boc-4-[2-(3-fluoropyridin-4-yl)ethyl]piperazine (6.2 g, 84%).

$^1$H NMR ($CDCl_3$).

CI-MS, m/e=310 (M+1)

D. 1-Boc-4-[2-(3-fluoropyridin-4-yl)ethyl]piperazine (6.0 g, 19.4 mmol) was dissolved in methanol (20 mL) and anisole (6 mL). To this solution, concentrated hydrochloric acid (15 mL) was added and the mixture stirred for 1 h. The solvents were removed under vacuum to provide a yellow solid. The residue was suspended in diethyl ether and sonicated for 1 h. The product was recovered by vacuum filtration, and the solid dried under vacuum to provide 1-[2-(3-fluoropyridin-4-yl)ethyl]piperazine trihydrochloride (5.2 g, 84%) as an off white solid.

$^1$H NMR ($CD_3OD$).

CI-MS, m/e=210 ($C_{11}H_{16}FN_3$+1).

Intermediate A-12

1-[2-(2-Cyanopyridin-4-yl)ethyl]piperazine.

A. Ethyl 4-pyridylacetate (20 g, 121 mmol) was added to a suspension of $LiAlH_4$ (9.2 g, 242 mmol) in diethyl ether (600 mL). Diatomaceous earth (about 50 mL) was added to aid stirring. The mixture stirred overnight. The mixture was cooled to 0° C. and aqueous NaOH (15%) was added until degassing ceased. The mixture was allowed to stir for 1 h. The solids were removed by filtration and the filtrate was concentrated under vacuum. The crude product was purified by chromatography ($SiO_2$, 40:1–20:1 $CH_2Cl_2$:methanol) to provide 4-(2-hydroxyethyl)pyridine (8.1 g, 54%) as an amber liquid.

$^1$H NMR ($CDCl_3$).

CI-MS, m/e=124 (M+1).

B. 4-(2-Hydroxyethyl)pyridine (8.1 g, 65.8 mmol) and triethylamine (10.1 mL, 66 mmol) were dissolved in $CH_2Cl_2$ (100 mL) and cooled to −78° C. To this solution, tert-butyldimethylsilyl chloride (11.0 g, 66 mmol) was added. The mixture was allowed to warm to room temperature overnight. The mixture was placed directly on a bed of $SiO_2$ and eluted with 100:0–10:1 $CH_2Cl_2$ methanol to provide 4-[2-(tert-Butyldimethylsilyloxy)ethyl]pyridine (15.3 g, 97%).

¹H NMR (CDCl₃).
CI-MS, m/e=238 (M+1)
C. 4-[2-(tert-Butyldimethylsilyloxy)ethyl]pyridine (15.2 g, 64 mmol) was dissolved in CH₂Cl₂ (200 mL). To this solution, m-chloroperbenzoic acid was added and the solution stirred at room temperature for 72 h. The solution was washed with aqueous NaOH (1 M) and layers separated. The water layer was extracted with CH₂Cl₂. The organic layers were combined, dried (K₂CO₃), filtered and concentrated under vacuum to provide 4-(2-(tert-butyldimethylsilyloxy)ethyl]pyridine-N-oxide (13.4 g, 83%).
¹H NMR (CDCl₃).
CI-MS, m/e 254 (M+1).
D. 4-[2-(tert-Butyldimethylsilyloxy)ethyl]pyridine-N-oxide (13.4 g, 52.9 mmol) was dissolved in triethylamine (14.8 mL, 105 mmol). Trimethylsilyl cyamide (28.4 mL, 212 mmol) was added and the mixture heated to 90° C. for 3 h. The mixture was allowed to cool to room temperature and stand overnight. The mixture was partitioned between water and CH₂Cl₂. The layers were separated and water layer extracted with CH₂Cl₂. The organic layers were combined, washed with water and brine, dried (K₂CO₃), filtered and concentrated to provide a dark oil (14 g). The residue was purified by chromatography (SiO₂, 40:1 CH₂Cl₂:ethyl acetate) to provide 4-[2-(tert-butyldimethylsilyloxy)ethyl]-2-cyanopyridine (12.8 g, 92%) as a yellow oil.
¹H NMR (CDCl₃).
CI-MS, m/e=263 (M+1).
E. 4-[2-(tert-Butyldimethylsilyloxy)ethyl]-2-cyanopyridine (12.8 g, 48.8 mmol) and a solution of tetrabutylammonium fluoride (1 M in THF, 73 mL, 73 mmol) were charged to a round bottom flask and stirred at room temperature overnight. The mixture was diluted with water and ethyl acetate. The layers were separated and the water layer extracted with ethyl acetate. The organic layers were combined, washed with water and brine, dried (Na₂SO₄), filtered and concentrated. The residue was purified by chromatography (SiO₂, 50:1 CH₂Cl₂: methanol) to provide 2-cyano-4-(2-hydroxyethyl)pyridine (4.4 g, 61%) as an off white solid.
¹H NMR (CDCl₃).
CI-MS, m/e=149 (M+1).
F. 2-Cyano-4-(2-hydroxyethyl)pyridine (4.3 g, 29 mmol) was dissolved in pyridine (2.85 mL, 34.8 mmol) and CH₂Cl₂ (40 mL) and cooled to 0° C. To this solution, benzenesulfonyl chloride (4.5 mL, 34.8 mmol) was added and the mixture allowed to stir at room temperature overnight. The solvent was removed under vacuum and the residue was purified by chromatography (SiO₂, 20:1 CH₂Cl₂: ethyl acetate) to provide a 2:1 mixture of 2-cyano-4-[2-(benzenesulfonyloxy)ethyl]pyridine and 2-cyano-4-(2-chloroethyl)pyridine (6.0 g, 84%).
¹H NMR (CDCl₃).
CI-MS, m/e 167 ($C_8H_7ClN_2$+1) and 289 ($C_{14}H_{12}N_2O_3S$+1).
G. 1-Boc-piperazine (6.8 g, 36 mmol), NaI (2.7 g, 18 mmol), K₂CO₃ (3.0 g, 21.6 mmol) and a mixture of 2-cyano-4-[2-(benzenesulfonyloxy)ethyl]pyridine and 2-cyano-4-(2-chloroethyl)pyridine (2:1, 4.5 g, 18 mmol) was dissolved in DMF (50 mL) and heated to 80° C. overnight. The mixture was allowed to cool to room temperature and diluted with water and ethyl acetate. The layers were separated and the water layer extracted with ethyl acetate. The organic layers were combined, washed with water and brine, dried (Na₂SO₄), filtered and concentrated under vacuum to proved a dark oil (6.0 g). The crude product was purified by chromatography (SiO₂, 1000:10:1–200:10:1 CH₂Cl₂:methanol:concentrated ammonium hydroxide) to provide 1-Boc-4-[2-(2-cyanopyridin-4-yl)ethyl]piperazine (4.0 g, 70%).

¹H NMR (CDCl₃).
TLC $R_f$=0.5 (200:10:1 CH₂Cl₂:methanol:concentrated ammonium hydroxide).
H. 1-Boc-4-[2-(2-cyanopyridin-4-yl)ethyl]piperazine (4.0 g, 12.64 mmol) was dissolved in methanol (60 mL) and cooled to 0° C. Concentrated hydrochloric acid (10.4 mL, 126 mmol) was added and the mixture stirred for 1 h. The solvents were removed under vacuum and co-evaporated twice with methanol, a 1:1 mixture of methanol/toluene, and finally with methanol. The residue was dried under vacuum overnight to provide crude product (4.5 g). Half of the product was dissolved in methanol, concentrated ammonium hydroxide was added, and solvents were removed under vacuum. The residue was purified by chromatography (SiO₂, 100:10:1 CH₂Cl₂:methanol:concentrated ammonium hydroxide) to provide 1-[2-(2-cyanopyridin-4-yl)ethyl]piperazine (1.05 g, 69%).
¹H NMR (CDCl₃).
CI-MS, m/e=217 (M+1).

Preparation of Intermediates B-1- B-5

The following compounds were prepared according to the indicated method (Method B-A, Method B—B or Method B-C) from the indicated starting materials, unless otherwise described.
Intermediate B-1
1-Boc-4-[(3-pyridinyl)acetyl]piperazine.

Method B-A

1-Boc-piperazine (12 g, 64 mmol), 3-pyridylacetic acid (8.85 g, 64 mmol), and HOBt (8.64 g, 64 mmol) were dissolved in DMF. To this solution, EDCI (14.7 g, 76.8 mmol) was added in portions. The mixture became homogenous and was stirred for 3 h. The mixture was diluted with water and ethyl acetate. The layers were separated, and the aqueous layer extracted with ethyl acetate. The organic layers were washed with water and brine, dried (Na₂SO₄), filtered, and concentrated to provide a yellow solid. The crude product was purified by recrystallization from hexanes:dichloromethane to provide 1-Boc-4-[(3-pyridinyl)acetyl]piperazine (13.5 g, 69%) as a white solid.
¹H-NMR (CDCl₃)
CI-MS, m/e=306 (M+1)
Intermediate B-2
1-Boc-4-[(imidazol-4-yl)acetyl]piperazine.

Method B—B

To a stirring suspension of sodium 4-imidazolylacetate (0.5 g, 3.4 mmol) in DMF (25 mL) was added diethyl cyanophosphonate (0.6 mL, 4 mmol). After 5 min, Boc-piperazine (0.57 g, 3.1 mmol) was added, followed by a solution of triethylamine (0.47 mL, 3.4 mmol) in DMF (20 mL). After 72 h, the solvent was removed in vacuo and the residue was dissolved in ethyl acetate and washed with satd aq. NaHCO₃ and brine, dried with MgSO₄, filtered and concentrated to give 0.95 g of pink oil.
¹H-NMR
IS-MS, m/e 295.1 (M+1)
Intermediate B-3
1-Boc-4-[(1-imidazolyl)acetyl]piperazine.
Preparation of Starting Materials:
1-Boc-4-bromoacetylpiperazine.

To a stirring solution of bromoacetyl bromide (29.8 g, 148 mmol) in THF (250 mL) at 0° C. was added via an addition funnel a solution of Boc-piperazine (25 g, 134 mmol) and triethylamine (14.9 g, 148 mmol) in THF (75 mL). After 1 h, a few grams of ice were added and the mixture was diluted with ethyl acetate and cold water. The layers were separated and the organic phase was washed with 1 M aq. citric acid, brine, satd aq. NaHCO$_3$ and again with brine. The organic phase was then dried with MgSO$_4$, filtered, and concentrated in vacuo to give 38.2 g (93%) of an off-white powder.

$^1$H-NMR

IS-MS, m/e 251.3 (M-C$_4$H$_9$+1)

Method B-C

To a stirring suspension of NaH (60% dispersion in mineral oil, 2.34 g, 59 mmol) in THF (75 mL) was added imidazole (1.46 g, 22 mmol) in small portions. After complete addition and complete gas evolution, a solution of 1-Boc-4-(bromoacetyl)piperazine (6 g, 19.5 mmol) in THF (40 mL) was added via an addition funnel. After 2 h, the reaction was quenched with the slow addition of water and then diluted with ethyl acetate. The organic phase was washed with satd aq. NaHCO$_3$, followed by brine, then dried with MgSO$_4$, filtered and concentrated in vacuo. The residue was suspended in diethyl ether with sonication, then filtered and dried to give 4.64 g (81%) of an off white powder.

$^1$H-NMR

IS-MS, m/e 295.2 (M+1)

Intermediate B-4

1-Boc-4-[(1-pyrazolyl) acetyl]piperazine.

Prepared from pyrazole and 1-Boc-4-bromoacetylpiperazine using Method B-C.

$^1$H-NMR

IS-MS, m/e 295.1 (M+1)

Intermediate B-5

1-Boc-4-[(2-Benzyloxycarbonylamino) thiazol-4-ylacetyl] piperazine.

A. (2-Aminothiazol-4-yl)acetic acid (10 g, 63.2 mmol) was dissolved in 1,4-dioxane (100 mL) and aqueous NaOH (6 M, 100 mL), and the solution was cooled to 0° C. Benzyl chloroformate (20 mL, 82.2 mmol) was added, and the mixture was stirred at room temperature overnight. The mixture was diluted with diethyl ether, and the layers separated. The water layer was cooled to 0° C., and the pH adjusted to approximately 4 with aqueous HCl (6 M). The white precipitate formed was collected by vacuum filtration, washed with water and diethyl ether, and dried under vacuum to provide (2-benzyloxycarbonylaminothiazol-4-yl) acetic acid (7.5 g, 41%).

$^1$H NMR (DMSO-d$_6$).

CI-MS, m/e=293 (M+1).

B. Using methods substantially equivalent to those described in Method B-A, the title compound was prepared from (2-benzyloxycarbonylaminothiazol-4-yl) acetic acid and 1-Boc-piperazine (95%).

$^1$H NMR (CDCl$_3$).

CI-MS, m/e=461 (M+1)

Preparation of Intermediates C-1-C-28

The following compounds were prepared according to the indicated method (Method C-A, Method C-B, Method C—C or Method C-D) from the indicated starting materials, unless otherwise described.

Intermediate C-1

1-(Boc-D-Phenylglycinyl)-4-[2-(4-pyridinyl)ethyl] piperazine.

Method C-A

D-Boc-Phenylglycine (8.4 g, 33.3 mmol) and 1-[2-(4-pyridinyl)ethyl]piperazine hydrochloride (10 g, 33.3 mmol) were dissolved in DMF (500 mL) and cooled to approximately −15° C. in an ice-methanol bath. Diethyl cyanophosphonate (5.5 mL, 36.6 mmol) was slowly added to the mixture. Triethylamine (18.6 mL, 133.2 mmol) was added dropwise to the solution. The mixture was stirred at −15° C. for 2 h and was allowed to gradually warm to-room temperature overnight. The mixture was diluted with ethyl acetate and water. The layers were separated, and the water layer extracted with ethyl acetate. The organic layers were combined, washed with brine, dried (Na$_2$SO$_4$), filtered, and concentrated under vacuum. The crude product was filtered through a plug of silica gel (1.2 kg) using 1:1 hexanes:ethyl acetate as eluent to provide 1-(Boc-D-phenylglycinyl)-4-[2-(4-pyridinyl)ethyl]piperazine (10.6 g, 75%) as a light yellow oil.

$^1$H-NMR (CDCl$_3$)

CI-MS, m/e=425 (M+1)

Intermediate C-2

1-(Boc-D-Phenylglycinyl)-4-[2-(2-pyridinyl)ethyl] piperazine.

Prepared from Boc-D-phenylglycine and 1-[2-(2-pyridinyl)ethyl]piperazine using Method C-A.

$^1$H-NMR (CDCl$_3$)

CI-MS, m/e=425 (M+1)

Intermediate C-3

1-(Boc-D-Phenylglycinyl)-4-[2-(2-pyrazinyl)ethyl] piperazine.

Prepared from Boc-D-phenylglycine and 1-[2-(2-pyrazinyl)ethyl]piperazine using Method C-A.

$^1$H-NMR (CDCl$_3$)

CI-MS, m/e=426 (M+1)

Intermediate C-4

1-(Boc-D-Phenylglycinyl)-4-[2-(3-pyridazinyl)ethyl] piperazine.

Prepared from Boc-D-phenylglycine and 1-[2-(3-pyridazinyl)ethyl]piperazine using Method C-A.

$^1$H NMR (CDCl$_3$)

TLC R=0.65 (100:10:1 CH$_2$Cl$_2$:MeOH:NH$_4$OH, SiO$_2$, Analtech No. 02521)

Intermediate C-5

1-(Boc-D-Phenylglycinyl)-4-[2-(3-pyridinyl)ethyl] piperazine.

Prepared from Boc-D-phenylglycine and 1-[2-(3-pyridinyl)ethyl]piperazine using Method C-A.

$^1$H-NMR (CDCl$_3$)

CI-MS, m/e=425 (M+1)

Intermediate C-6

1-(Boc-D-Phenylglycinyl)-4-[2-(4-imidazolyl)ethyl] piperazine

Prepared from Boc-D-phenylglycine and 1-[2-(4-imidazolyl)ethyl]piperazine using Method C-A.

$^1$H-NMR

IS-MS, m/e 414.2 (M+1)

Intermediate C-7

1-(Boc-D-Phenylglycinyl)-4-[2-(4-pyrazolyl)ethyl] piperazine.

Prepared from Boc-D-phenylglycine and 1-[2-(4-pyrazolyl)ethyl]piperazine using Method C-A.

$^1$H-NMR

IS-MS, m/e 414.2 (M+1)

Intermediate C-8
1-(Boc-D-Phenylglycinyl)-4-[2-(1-imidazolyl)ethyl]piperazine.

Prepared from Boc-D-phenylglycine and 1-[2-(1-imidazolyl)ethyl]piperazine using Method C-A.
$^1$H-NMR
IS-MS, m/e 414.2 (M+1)

Intermediate C-9
1-(Boc-D-Phenylglycinyl)-4-[2-(1-pyrazolyl)ethyl]piperazine.

Prepared from Boc-D-phenylglycine and 1-[2-(1-pyrazolyl)ethyl]piperazine using Method C-A.
$^1$H-NMR
IS-MS, m/e 414.2 (M+1)

Intermediate C-10
1-[Boc-D,L-(Pyridin-2-yl)glycinyl]-4-[2-(4-pyridinyl)ethyl]-piperazine.

Method C-B

To a stirring solution of ethyl Boc-D,L-(pyridin-2-yl)glycine (16.3 g, 58.2 mmol) in 1,4-dioxane (100 mL) was added a solution of LiOH hydrate (2.68 g, 64 mmol) in water (100 mL). After 2 h, another solution of LiOH hydrate (1.34 g, 32 mmol) in water (50 mL) was added. After another 2 h, the solvent was evaporated in vacuo to give 13.56 g of off-white solid.

A portion of the solid (3 g, 11.6 mmol) was dissolved in DMF (75 mL) and cooled to 0° C. To this solution was added diethyl cyanophosphonate (2.3 g, 13.9 mmol), N,N-diisopropylethylamine (6 g, 46.4 mmol) and then 1-[2-(4-pyridyl)ethyl]piperazine hydrochloride (3.8 g, 12.8 mmol), and the reaction was allowed to slowly warm to room temperature overnight. The next morning, the solvents were removed in vacuo and the residue was dissolved in ethyl acetate and washed with satd aq. NaHCO$_3$ and brine, then dried with Na$_2$SO$_4$, filtered, and concentrated in vacuo. The residue was then dissolved in a minimal volume of dichloromethane and chromatographed over silica gel, eluting with a step gradient of 2% through 10% methanol (with 2 N NH$_3$) in dichloromethane. The product containing fractions were combined and concentrated in vacuo to give 2.31 g (47%) of an off-white foam.
$^1$H-NMR
IS-MS, m/e 426.3 (M+1)

Intermediate C-1
1-[Boc-D,L-(2-Methoxy-phenyl)glycinyl]-4-[2-(4-pyridinyl)ethyl]piperazine.

Method C—C

To a stirring solution of Boc-D,L-(2-methoxyphenyl)glycine (2 g, 7.1 mmol) and 1-[2-(4-pyridinyl)ethyl]piperazine trihydrochloride (2.4 g, 7.8 mmol) in DMF (50 mL), was added HOBt (1.06 g, 7.8 mmol), and triethylamine (4.96 mL, 35.6 mmol) followed by DCC (1.61 g, 7.8 mmol). After stirring overnight at room temperature, the mixture was filtered; and the filtrate was concentrated in vacuo. The residue was dissolved in ethyl acetate and washed with satd aq. NaHCO$_3$ followed by brine, then dried with MgSO$_4$, filtered and concentrated in vacuo. The residue was then dissolved in a minimum amount of dichloromethane and chromatographed over silica gel, eluting with a step gradient of dichloromethane through 10% (2 N NH$_3$/methanol) in dichloromethane. The product containing fractions were combined and concentrated in vacuo to give 2.5 g (77%) of the title compound.

$^1$H-NMR
IS-MS, m/e 455.1 (M+1)

Intermediate C-12
1-(Boc-D-Phenylglycinyl)-4-[2-(thiazol-2-yl)ethyl]piperazine.

Prepared from 1-[2-(thiazol-2-yl)ethyl]piperazine dihydrochloride and Boc-D-phenylglycine using Method C-A, except using dichloromethane in place of DMF (80%).
$^1$H NMR (CDCl$_3$)
CI-MS, m/e=431 (C$_{22}$H$_{30}$N$_4$O$_3$S+1).

Intermediate C-13
1-(Boc-D-Phenylglycinyl)-4-[2-(2-benzyloxycarbonylaminothiazol-4-yl)ethyl]piperazine.

Prepared from 1-[2-(2-benzyloxycarbonylaminothiazol-4-yl)ethyl]piperazine hydrochloride and Boc-D-phenylglycine using Method C-A (76%).
$^1$H NMR (CDCl$_3$).
APCI-MS, m/e=580 (M+1).

Intermediate C-14
1-(Boc-D-Phenylglycinyl)-4-[2-(3-fluoropyridin-4-yl)ethyl]piperazine.

Prepared from 1-(Boc-D-phenylglycinyl)-4-[2-(3-fluoropyridin-4-yl)ethyl]piperazine using Method C-A, except using N,N-diisopropylethylamine in place of triethylamine and dichloromethane in place of DMF (89%).
$^1$H NMR (CDCl$_3$).
APCI-MS, m/e=443 (M+1).

Intermediate C-15
1-(Boc-D-Phenylglycinyl)-4-[2-(2-cyanopyridin-4-yl)ethyl]-piperazine.

Method C-D

1-[2-(2-cyanopyridin-4-yl)ethyl]piperidine (1.0 g, 4.6 mmol) and Boc-D-phenylglycine (1.39 g, 4.63 mmol) were dissolved in CH$_2$Cl$_2$ (20 mL) and cooled to −10° C. To this solution, diethyl cyanophosphonate (0.94 mL, 4.63 mmol) was added, followed by a solution of triethylamine (0.97 mL, 6.9 mmol) in CH$_2$Cl$_2$ (10 mL). The mixture was allowed to slowly warm to room temperature overnight. The mixture was diluted with water and the layers separated. The water layer was extracted with CH$_2$Cl$_2$. The organic layers were combined, washed with brine, dried (Na$_2$SO$_4$), filtered and concentrated under vacuum to provide crude product (3.0 g). The crude product was purified by chromatography (SiO$_2$, 1000:10:1–400:10:1 CH$_2$Cl$_2$:methanol:concentrated ammonium hydroxide) to provide 1-(Boc-D-phenylglycinyl)-4-[2-(2-cyanopyridin-4-yl)ethyl]piperazine (1.61 g, 78%).
$^1$H NMR (CDCl$_3$).
CI-MS, m/e=450 (M+1).

Intermediate C-16
1-[Boc-D,L-(2-Chlorophenyl)glycinyl]-4-(1-methylpiperidin-4-yl)piperazine.

Prepared from Boc-D,L-(2-chlorophenyl)glycine and 1-(1-methylpiperidin-4-yl)piperazine using Method C—C, with EDCI in place of DCC and HOAt in place of HOBt.
1H NMR
IS-MS, m/e 451.0 (M+1)

Intermediate C-17
1-[Boc-D,L-(Quinolin-8-yl)glycinyl]-4-(1-methylpiperidin-4-yl)piperazine.

Prepared from Boc-D,L-(quinolin-8-yl)glycine and 1-(1-methylpiperidin-4-yl)piperazine using Method C—C, with EDCI in place of DCC and HOAt in place of HOEt.
1H NMR Intermediate C-18
1-[Boc-D,L-(2-Trifluoromethylphenyl)glycinyl]-4-(1-methylpiperidin-4-yl)piperazine.

Prepared from Boc-D,L-(2-trifluoromethylphenyl)glycine and 1-(1-methylpiperidin-4-yl)piperazine using Method C—C, with DIEA in place of TEA.

1H NMR

IS-MS, m/e 485.0 (M+1)

Intermediate C-19
1-[Boc-D-Cyclopentylglycinyl]-4-(1-methylpiperidin-4-yl)piperazine.

Prepared from Boc-D-cyclopentylglycine and 1-(1-methylpiperidin-4-yl)piperazine using Method C—C, with EDCI in place of DCC and HOAt in place of HOBt.

1H NMR

IS-MS, m/e 409.3 (M+1)

Intermediate C-20
1-[Boc-D-Cyclohexylglycinyl]-4-(1-methylpiperidin-4-yl)piperazine.

Prepared from Boc-D-cyclohexylglycine and 1-(1-methylpiperidin-4-yl)piperazine using Method C—C, with EDCI in place of DCC and HOAt in place of HOBt.

1H NMR

IS-MS, m/e 423.3 (M+1)

Intermediate C-21
1-[Cbz-D-Phenylglycinyl]-4-(2-phenethyl)piperazine.

Prepared from 4-(Cbz-D-phenylglycinyl)piperazine and phenylacetaldehyde using Method I-A, with sodium triacetoxyborohydride in place of sodium cyanoborohydride and dichloroethane in place of methanol (71%).

1H NMR (CDCl$_3$).

APCI-MS, m/e=458 (M+1).

Intermediate C-22
1-[Boc-D,L-(thiazol-2-yl)glycinyl]-4-(1-methylpiperidin-4-yl)piperazine.

Prepared from ethyl Boc-D,L-thiazol-2-ylglycine and 1-(1-methylpiperidin-4-yl)piperazine using Method C-B.

IS-MS, m/e 424.0 (M+1)

Intermediate C-23
1-[Boc-D,L-(Benzo[b]thiophen-3-yl)glycinyl]-4-(1-methylpiperidin-4-yl)piperazine.

Prepared from Boc-D,L-(benzo[b]thiophen-3-yl)glycine and 1-(1-methylpiperidin-4-yl)piperazine using Method C—C, substituting EDCI for DCC, N,N-diisopropylamine for triethylamine, and substituting dichloromethane for DMF.

1H-NMR

LCMS m/z 473.4 (M+1)

Intermediate C-24
1-[Boc-D,L-(Naphthalen-1-yl)glycinyl]-4-(1-methylpiperidin-4-yl) piperazine.

Prepared from Boc-D,L-naphthalen-1-ylglycine and 1-(1-methylpiperidin-4-yl)piperazine using Method C—C, substituting EDCI for DCC and substituting N,N-diisopropylamine for triethylamine.

1H-NMR

IS-MS, m/e 467.1 (M+1)

Intermediate C-25
1-[Boc-D,L-(2-Methylsulfonylphenyl)glycinyl]-4-(1-methylpiperidin-4-yl)piperazine.

Prepared from Boc-D,L-(2-methylsulfonylphenyl)glycine and 1-(1-methylpiperidin-4-yl)piperazine using Method C—C, substituting EDCI/HOAt for DCC/HOBt and substituting N,N-diisopropylethylamine for triethylamine.

1H-NMR

IS-MS, m/e 495 (M+1)

| Analysis for $C_{24}H_{38}N_4O_5S$: | |
|---|---|
| Calcd: | C, 58.27; H, 7.74; N, 11.32; |
| Found: | C, 58.05; H, 7.63; N, 11.43. |

Intermediate C-26
1-[Boc-D,L-Thiazol-5-ylglycinyl]-4-[2-(pyridin-4-yl)ethyl]-piperazine.

To a solution of Boc-D,L-thiazol-5-ylglycine (1.33 g, 5.15 mmol), HOAt (772 mg, 5.67 mmol), 1-[2-(pyridin-4-yl)ethyl]piperazine dihydrochloride (1.55 g, 5.15 mmol) and triethylamine (1.58 mL, 11.3 mmol) in DMF (41 mL) was added EDCI (1.09 g, 5.67 mmol), and the mixture stirred at room temperature for 18 h. The solvent was removed in vacuo, the residues taken up in chloroform: isopropyl alcohol (2:1) and washed with water, satd aqueous sodium bicarbonate, dried (MgSO$_4$) and concentrated in vacuo to an orange-brown oil. The crude reaction product thus obtained was carried on to the next step without further purification.

Intermediate C-27
1-[Boc-D,L-(2-Methylthiazol-4-yl)glycinyl]-4-[2-(pyridin-4-yl)ethyl]piperazine.

Prepared from Boc-D,L-(2-methylthiazol-4-yl)glycine and 1-[2-(pyridin-4-yl)ethyl]piperazine dihydrochloride using procedures substantially equivalent to those described for the preparation of Intermediate C-26.

Intermediate C-28
1-[Boc-D,L-(2-Benzyloxycarbonylaminothiazol-4-yl)glycinyl]-4-[2-(pyridin-4-yl)ethyl]piperazine.

Prepared from Boc-D,L-(2-benzyloxycarbonylaminothiazol-4-yl)glycine and 1-[2-(pyridin-4-yl)ethyl]piperazine dihydrochloride using procedures substantially equivalent to those described for the preparation of Intermediate C-26.

Preparation of Intermediates D-1-D-28

The following compounds were prepared according to the indicated method (Method D-A, Method D-B, Method D-C, Method D—D or Method D-F) from the indicated starting material, unless otherwise described.

Intermediate D—1
1-(D-Phenylglycinyl)-4-[2-(4-pyridinyl)ethyl]piperazine Hydrochloride.

Method D-A 1-(Boc-D-phenylglycinyl)-4-[2-(4-pyridinyl)ethyl]piperazine (13 g, 30.6 mmol) and anisole (50 mL) were dissolved in methanol and cooled to 0° C. Concentrated hydrochloric acid (40 mL, 300 mmol) was added dropwise to the solution, and the mixture allowed to warm to room temperature. The mixture stirred for 1 h, and the solvent and anisole were removed under vacuum. The residue was suspended in diethyl ether and sonicated for 1 h. The solid product was filtered and dried under vacuum (0.5 torr, 66 Pa at 50–60° C.) to give 1-(D-phenylglycinyl)-4-[2-(4-pyridinyl)ethyl]piperazine hydrochloride (11.8 g, 89%) as a white, hygroscopic solid.

1H NMR (CD$_3$OD)

API-MS, m/e=325 (M+1)

Intermediate D-2
1-(D-Phenylglycinyl)-4-[2-(2-pyridinyl)ethyl]piperazine.
Prepared from 1-(Boc-D-phenylglycinyl)-4-[2-(2-pyridinyl)ethyl]piperazine using Method D-A.
$^1$H NMR (CD$_3$OD)
API-MS, m/e=325 (M+1)

Intermediate D-3
1-(D-Phenylglycinyl)-4-[2-(2-pyrazinyl)ethyl]piperazine.
Prepared from 1-(Boc-D-phenylglycinyl)-4-[2-(2-pyrazinyl)ethyl]piperazine using Method D-A.
1H NMR (CD$_3$OD)
API-MS, m/e=326 (M+1)

Intermediate D-4
1-(D-Phenylglycinyl)-4-[2-(3-pyridazinyl)ethyl]piperazine.
Prepared from 1-(Boc-D-phenylglycinyl)-4-[2-(3-pyridazinyl)ethyl]piperazine using Method D-A.
1H-NMR (CD$_3$OD)
IS-MS, m/e 326 (M+1)

Intermediate D-5
1-(D-Phenylglycinyl)-4-[2-(3-pyridinyl)ethyl]piperazine.
Prepared from 1-(Boc-D-phenylglycinyl)-4-[2-(3-pyridinyl)ethyl]piperazine using Method D-A.
1H NMR (CD$_3$OD)
API-MS, m/e=325 (M+1)

Intermediate D-6
1-(D-Phenylglycinyl)-4-[2-(4-imidazolyl)ethyl]piperazine.
Prepared from 1-(Boc-D-phenylglycinyl)-4-[2-(4-imidazolyl)ethyl]piperazine using Method D-A.
$^1$H-NMR
IS-MS, m/e 314.1 (M+1)

Intermediate D-7
1-(D-Phenylglycinyl)-4-[2-(4-pyrazolyl)ethyl]piperazine.
Prepared from 1-(Boc-D-phenylglycinyl)-4-[2-(4-pyrazolyl)ethyl]piperazine using Method D-A.
1H-NMR
IS-MS, m/e 314.3 (M+1)

Intermediate D-8
1-(D-Phenylglycinyl)-4-[2-(1-imidazolyl)ethyl]piperazine.
Prepared from 1-(Boc-D-phenylglycinyl)-4-[2-(1-imidazolyl)ethyl]piperazine using Method D-A.
$^1$H-NMR
IS-MS, m/e 314.1 (M+1)

Intermediate D-9 (PD7-H7C-045, -046)
1-(D-Phenylglycinyl)-4-[2-(1-pyrazolyl)ethyl]piperazine.
Prepared from 1-(Boc-D-phenylglycinyl)-4-[2-(1-pyrazolyl)ethyl]piperazine using Method D-A.
1H-NMR
IS-MS, m/e 314.1 (M+1)

Intermediate D-10
1-[D,L-(Pyridin-2-yl)glycinyl]-4-[2-(4-pyridinyl)ethyl3-piperazine.

Method D-B

To a stirring solution of 1-[Boc-D,L-(pyridin-2-yl)glycinyl-4-[2-(4-pyridinyl)ethyl]piperazine (2.31 g, 5.4 mmol) in dichloromethane (45 mL) was added TFA (5 mL). After 6 h, the solvents were removed in vacuo. The residue was partitioned between ethyl acetate and satd aq. NaHCO$_3$, and the layers were separated. The aqueous phase was extracted with 50% ethyl acetate/dichloromethane, then 5% methanol/dichloromethane. The combined organic extracts were dried with MgSO$_4$, filtered and concentrated to give 1.66 g (94%) of the title compound.
1H-NMR
IS-MS, m/e 326.1 (M+1)

Intermediate D-11
1-[D,L-(2-Methoxyphenyl)glycinyl]-4-[2-(1-pyrazolyl)ethyl]piperazine.
Prepared from 1-[Boc-D,L-(2-methoxyphenyl)glycinyl]-4-[2-(1-pyrazolyl)ethyl]piperazine using Method D-B.
1H-NMR
IS-MS, m/e 355.1 (M+1)

Intermediate D-12
1-(D-Phenylglycinyl)-4-[2-(thiazol-2-yl)ethyl]piperazine Trihydrochloride.
Prepared from 1-(Boc-D-phenylglycinyl)-4-[2-(thiazol-2-yl)ethyl]piperazine using methods substantially equivalent to those described in Method D-A (80%).
$^1$H NMR (CD$_3$OD).
CI-MS, m/e=331 (C$_{17}$H$_{22}$N$_{40}$S+1).

Intermediate D-13
1-(D-Phenylglycinyl)-4-[2-(2-benzyloxycarbonylaminothiazol-4-yl)ethyl]piperazine Trihydrochloride.

Method D-C 1-(Boc-D-Phenylglycinyl)-4-[2-(2-benzyloxycarbonylaminothiazol-4-yl)ethyl]piperazine (520 mg, 0.898 mmol) was dissolved in ethyl acetate (10 mL) and anisole (1 mL). The mixture was cooled to 0° C., and a saturated solution of HCl in ethyl acetate was added. The mixture was allowed to warm to room temperature and stirred for 4 h. The solvent was removed under vacuum to provide the title compound as a white solid (530 mg, quantitative).
$^1$H NMR (CD$_3$OD).
APCI-MS, m/e=480 (C$_{25}$H$_{29}$N$_5$O$_3$S+1).

Intermediate D-14
1-(D-Phenylglycinyl)-4-[2-(3-fluoropyridin-4-yl)ethyl]-piperazine Trihydrochloride.
Prepared from 1-(Boc-D-phenylglycinyl)-4-[2-(3-fluoropyridin-4-yl)ethyl]piperazine using a method substantially equivalent to Method D-A (98%).
$^1$H NMR (CD$_3$OD).
APCI-MS, m/e=353 (C$_{19}$H$_{23}$FN$_4$O+1).

Intermediate D-15
1-(D-Phenylglycinyl)-4-[2-(2-cyanopyridin-4-yl)ethyl]piperazine Trihydrochloride.

Method D—D 1-(Boc-D-phenylglycinyl)-4-[2-(2-cyanopyridin-4-yl)ethyl]piperazine (580 mg, 1.29 mmol) and anisole (5.0 g, 4.64 mmol) were dissolved in methanol (10 mL) and cooled to −15° C. To this solution, concentrated (6 N) hydrochloric acid (1.2 mL, 11.6 mmol) was added, and the mixture stirred at −10° C. for 1 hour. The solvents were removed under vacuum and the residue co-evaporated with methanol, methanol and toluene, and methanol and ethyl acetate to provide 1-(D-phenylglycinyl)-4-[2-(2-cyanopyridin-4-yl)ethyl]piperazine trihydrochloride (600 mg, 100%) as an off white solid.
$^1$H NMR (CD$_3$OD).
CI-MS, m/e 350 (M+1).

Intermediate D-16
1-[D,L-(2-Chlorophenyl)glycinyl]-4-(1-methylpiperidin-4-yl)piperazine.
Prepared from 1-[Boc-D,L-(2-chlorophenyl)glycinyl]-4-(1-methylpiperidin-4-yl)piperazine using Method D-E.
1H NMR
IS-MS, m/e (M+1)

Intermediate D-17
1-[D,L-(Quinolin-8-yl)glycinyl]-4-(1-methylpiperidin-4-yl)piperazine.

Method D-E

To a stirring solution of 1-[Boc-D,L-(quinolin-8-yl)glycinyl]-4-(1-methylpiperidin-4-yl)piperazine (0.53 g, 1.13 mmol) and anisole (0.62 mL, 5.67 mmol) in dichloromethane (22 mL) was added TFA (2.2 mL). After 4 h, the solvents were removed in vacuo, and the residue was dissolved in methanol and loaded onto an SCX column (pretreated with 5% acetic acid in methanol and washed with methanol). The column was washed with methanol and then the product was eluted with 30% (2 N ammonia/methanol) in dichloromethane. The product containing fractions were combined and concentrated in vacuo to give approximately 0.4 g (quantitative) of the title compound.

1H NMR

Intermediate D-18
1-[D,L-(2-Trifluoromethylphenyl)glycinyl]-4-(1-methylpiperidin-4-yl)piperazine.

Prepared from 1-(Boc-D,L-(2-trifluoromethylphenyl)glycinyl]-4-(1-methylpiperidin-4-yl)piperazine using Method D-E.

1H NMR
IS-MS, m/e 385.1 (M+1)

Intermediate D-19
1-[D-Cyclopentylglycinyl]-4-(1-methylpiperidin-4-yl)piperazine.

Prepared from 1-[Boc-D-cyclopentylglycinyl]-4-(1-methylpiperidin-4-yl)piperazine using Method D-E.

1H NMR
IS-MS, m/e 309.2 (M+1)

Intermediate D-20
1-[D-Cyclohexylglycinyl]-4-(1-methylpiperidin-4-yl-)piperazine.

Prepared from 1-[Boc-D-cyclohexylglycinyl]-4-(1-methylpiperidin-4-yl)piperazine using Method D-E.

IS-MS, m/e 323.3 (M+1)

Intermediate D-21
1-[D-Phenylglycinyl]-4-(2-phenethyl)piperazine.

Method D-F 1-(Cbz-D-Phenylglycinyl)-4-(2-phenethyl)piperazine (1.66 g; 3.63 mmol) was dissolved in methanol (46 mL) with 10% Pd/C (394 mg) and reaction mixture was subjected to a balloon of hydrogen for 15 h. Only 50% conversion was observed; so the catalyst was filtered through diatomaceous earth, and the mixture was re-subjected to the same conditions for 17 h. The catalyst was filtered through diatomaceous earth, and the solvent was removed under vacuum to give the title compound (1.03 g; 88%).

$^1$H NMR (CDCl$_3$).

APCI-MS, m/e=324 (M+1).

Intermediate D-22
1-[D,L-(Thiazol-2-yl)glycinyl]-4-(1-methylpiperidin-4-yl)piperazine Trihydrochloride.

Prepared from 1-[Boc-D,L-(thiazol-2-yl)glycinyl]-4-(1-methylpiperidin-4-yl)piperazine using Method A—A. In this procedure, saturated HCl in 1,4-dioxane was used in place of saturated HCl in methanol. Concentration of the reaction mixture provided the title compound as a crude residue that was used directly without purification.

Intermediate D-23
1-[D,L-(Benzo[b]thiophen-3-yl)glycinyl]-4-(1-methylpiperidin-yl)piperazine Trihydrochloride.

Prepared from 1-[Boc-D,L-(benzo[b]thiophen-2-yl)glycinyl]-4-(1-methylpiperidin-4-yl)piperazine using Method A, Part B. In this procedure, saturated HCl in 1,4-dioxane was used in place of saturated HCl in methanol.

LCMS m/z 373.5 (M+1)

Intermediate D-24
1-[D,L-(Naphthalen-1-yl)glycinyl]-4-(1-methylpiperidin-4-yl)piperazine Trihydrochloride.

Prepared from 1-[Boc-D,L-(naphthalen-1-yl)glycinyl]-4-(1-methylpiperidin-4-yl)piperazine using Method A—A, Part B. In this procedure, saturated HCl in 1,4-dioxane was used in place of saturated HCl in methanol.

1H-NMR
IS-MS m/e 367.0 (M+1)

Intermediate D-25
1-D,L-(2-Methylsulfonylphenyl)glycinyl-4-(1-methylpiperidin-4-yl)piperazine.

Prepared from 1-[Boc-D,L-(2-methylsulfonylphenyl)glycinyl]-4-(1-methylpiperidin-4-yl)piperazine using Method D—D.

1H-NMR
IS-MS, m/e 395 (M+1)

Intermediate D-26
1-[D,L-(Thiazol-5-yl)glycinyl]-4-[2-(pyridin-4-yl)ethyl]-piperazine.

To a stirred solution of crude 1-[D,L-(thiazol-5-yl)glycinyl]-4-[2-(pyridin-4-yl)ethyl]piperazine (circa 5.15 mmol) and anisole (11.2 mL) in dichloromethane (42 mL) at room temperature was added TFA (10.5 mL), and the mixture stirred at room temperature for 16 h before concentrating in vacuo. The product was isolated using SCX ion exchange chromatography.

Intermediate D-27
1-[D,L-(2-Methylthiazol-4-yl)glycinyl]-4-[2-(pyridin-4-yl)ethyl]piperazine.

Prepared from 1-[Boc-D,L-(2-methylthiazol-4-yl)glycinyl]-4-[2-(pyridin-4-yl)ethyl]piperazine using procedures substantially equivalent to those described in the preparation of Intermediate D-26.

NMR

Intermediate D-28
1-[D,L-(2-Aminothiazol-4-yl)glycinyl]-4-[2-(pyridin-4-yl)ethyl]piperazine.

A stirred solution of 1-(Boc-D,L-2-benzyloxycarbonylaminothiazol-4-ylglycinyl)-4-[2-(pyridin-4-yl)ethyl]piperazine (crude, circa 4.2 mmol) in a mixture of HBr-acetic acid (50%, 35 mL) and acetic acid (70 ml) was heated at 60° C. for 6 h, cooled and then concentrated in vacuo. The title product was isolated using SCX ion exchange chromatography.

NMR

Preparation of Intermediates E

The following compounds were prepared according to the indicated method (Method E-A) from the indicated starting material, unless otherwise described.

Intermediate E-1
1-Boc-4-(Cbz-D-phenylglycinyl)piperazine.

Method E-A

D-Cbz-phenylglycine (58.0 g, 203 mmol) and 1-Boc-piperazine (41.7 g, 224 mmol) were dissolved in DMF (1 L) and cooled to approximately −15° C. in an ice-methanol bath. Diethyl cyanophosphonate (37.0 mL, 244 mmol) was slowly added to the mixture. Triethylamine (59.4 mL, 426 mmol) was added dropwise to the solution. The mixture was stirred at −15° C. for 2 h and was allowed to gradually warm to room temperature overnight. The mixture was diluted with ethyl acetate and water. The layers were separated, and the water layer extracted with ethyl acetate. The organic layers were combined, washed with 10% citric acid (2×500 mL) and brine, dried ($Na_2SO_4$), filtered and concentrated under vacuum. The crude product was filtered through a plug of silica gel (1.2 kg) using 1:1 hexanes:ethyl acetate as eluent to provide 1-Boc-4-(Cbz-D-phenylglycinyl) piperazine (69.9 g, 76%) as a colorless oil.

1H-NMR ($CDCl_3$)

API-MS, m/e 454 (M+1)

Preparation of Intermediates F

The following compounds were prepared according to the indicated method (Method F-A) from the indicated starting material, unless otherwise described.

Intermediate F-1

1-Boc-4-(D-phenylglycinyl)piperazine.

Method F-A

1-Boc-4-(Cbz-D-phenylglycinyl)piperazine (69.5 g, 153 mmol) was dissolved in ethanol (500 mL). The mixture was degassed with nitrogen and 10% Pd/C (6.8 g) was added. Hydrogen was bubbled through the mixture for 1 h, and it was maintained under a hydrogen atmosphere for 16 h. The Pd/C was removed by filtration through cellulose. The filter cake was rinsed with ethanol and ethyl acetate. The filtrate was concentrated under vacuum to give 1-Boc-4-(D-phenylglycinyl)piperazine (45.3 g, 93%) as a light yellow solid.

1H-NMR ($CDCl_3$)

API-MS, m/e=320 (M+1)

Preparation of Intermediates G

The following compounds were prepared according to the indicated method (Method G-A) from the indicated starting material, unless otherwise described.

Intermediate G-1

1-Boc-4-(4-Methoxybenzoyl-D-phenylglycinyl)piperazine.

Method G-A

1-Boc-4-(D-phenylglycinyl)piperazine (42.0 g, 131.5 mmol) was dissolved in 1,4-dioxane (420 mL) and water (210 mL) and was cooled to 10° C. Potassium carbonate (36.4 g, 263 mmol) was added, followed by p-methoxybenzoyl chloride (24.7 g, 144 mmol). The mixture stirred at room temperature overnight. The mixture was diluted with water and ethyl acetate. The layers were separated and the water layer extracted with ethyl acetate. The organic layers were combined, washed with brine, dried, filtered and concentrated to provide 1-Boc-4-(4-methoxybenzoyl-D-phenylglycinyl)piperazine (58.7 g, 98%) as an off-white solid.

1H-NMR ($CDCl_3$)

API-MS, m/e=454 (M+1)

Preparation of Intermediates H

The following compounds were prepared according to the indicated method (Method H-A) from the indicated starting material, unless otherwise described.

Intermediate H-1

1-(4-Methoxybenzoyl-D-phenylglycinyl)piperazine Trifluoroacetate.

Method E-A

1-Boc-4-(4-Methoxybenzoyl-D-phenylglycinyl) piperazine (20.0 g, 44.1 mmol) was dissolved in dichloromethane (50 mL) and anisole (20 mL). To this vigorously stirred mixture was added trifluoroacetic acid (50 mL). The mixture was stirred for 25 min at room temperature. The solvents were removed under vacuum. The residue was triturated in ether and sonicated for 60 min. The solid was collected by filtration and dried in a vacuum pistol overnight to provide 1-(4-methoxybenzoyl-D-phenylglycinyl) piperazine trifluoroacetate (18.2 g, 88%) as a light yellow solid.

1H-NMR ($CD_3OD$)

API-MS, m/e=354 (M+1)

PREPARATION OF EXAMPLES

The following examples of formula (I) were prepared according to the indicated method (Method I-A, Method I-B, Method I-C, Method I-D, Method I-E, Method I-F or Method I-G) from the indicated starting materials, unless otherwise described.

Example 1

1-(4-Methoxybenzoyl-D-phenylglycinyl)-4-phenethylpiperazine.

Method I-A

To a stirring solution of 1-(4-methoxybenzoyl-D-phenylglycinyl)piperazine (0.05 g, 0.14 mmol) in methanol (1 mL) was added phenylacetaldehyde (0.17 mL, 1.4 mmol), followed by acetic acid (0.05 mL, 0.87 mmol) and then sodium cyanoborohydride (0.014 g, 0.21 mmol). After 2 h, the solution was loaded onto an SCX column, which was pretreated with 5% acetic acid/methanol. The column was washed with methanol and then the product was eluted with 10/1 dichloromethane:(2 N $NH_3$ in methanol). The product containing fractions were combined and concentrated to give 63 mg of thick oil (90% pure by analytical HPLC). The crude product was dissolved in a minimal volume of dichloromethane and chromatographed over silica gel, eluting with dichloromethane, followed by ethyl acetate, followed by a gradient of 2% through 10% (2 N $NH_3$/methanol) in dichloromethane. The product containing fractions were combined and concentrated to give 0.022 g (34%) of the title compound.

1H-NMR

IS-MS, m/e 458.0 (M+1)

HPLC Analysis (Method A): 100% $t_r$=27.44 min.

Example 2

1-(4-Methoxybenzoyl-D-phenylglycinyl)-4-[2-(4-pyridinyl) ethyl]piperazine Diydrochloride.

Method I-B 1-(D-Phenylglycinyl)-4-[2-(4-pyridinyl)ethyl]piperazine trihydrochloride (1.0 g, 2.31 mmol) and potassium carbonate (2.0 g, 144.4 mmol) were dissolved in 1,4-dioxane (5 mL) and water (1 mL). To this solution, p-anisoyl chloride (650 AL, 4.62 mmol) was added. The mixture stirred at room temperature for 3 h. The mixture was diluted with water, and the mixture extracted with ethyl acetate. The organic layers were combined, washed with brine, dried (Na$_2$SO$_4$), filtered and concentrated. The residue was dissolved in methanol and loaded onto an SCX column (10 g, pretreated with 5% acetic acid in methanol and washed with methanol). The by-products were eluted with methanol (about 20 mL), and desired product eluted with saturated ammonia in methanol. The product was further purified by column chromatography (SiO$_2$, CH$_2$Cl$_2$:CMA 20:1 to 9:1 gradient). The product was dissolved in methanol, and HCl in diethyl ether was added to provide 1-(4-methoxybenzoyl-D-phenylglycinyl)-4-[2-(4-pyridinyl)ethyl]piperazine hydrochloride (370 mg, 37%) as an off white solid.

1H-NMR (CDCl$_3$)

CL-MS, m/e=459 (M+1)

| Analysis for C$_{27}$H$_{30}$N$_4$O$_3$.2.2 HCl.1.1 H$_2$O.0.4 NH$_4$Cl: | |
| --- | --- |
| Calcd: | C, 55.91; H, 6.26; N, 10.63; |
| Found: | C, 56.04; H, 6.55; N, 10.46. |

HPLC Analysis (Method B): 99.7%, t$_R$=10.98 min.

Example 3

1-(Indole-6-carbonyl-D-phenylglycinyl)-4-[2-(4-pyridinyl)ethyl]piperazine.

Method I-C 1-(D-Phenylglycinyl)-4-[2-(4-pyridinyl)ethyl]piperazine (1.0 g, 2.31 mmol), 6-carboxyindole (371 mg, 2.31 mmol), HOBt (312 mg, 2.31 mmol), Et$_3$N (1.3 mL, 9.24 mmol), and DCC (620 mg, 3.00 mmol) were stirred in DMF at room temperature overnight. The precipitate was removed by filtration, and the filtrate concentrated under vacuum to a thick paste. The residue was dissolved in methanol and purified by ion exchange chromatography (SCX resin, methanol then saturated NH$_3$ in methanol) to provide the crude product as a brown solid. The crude product was purified by chromatography (SiO$_2$, 20:1 CH$_2$Cl$_2$:CMA to 6:1 CH$_2$Cl$_2$:CMA) to provide 1-(indole-6-carbonyl-D-phenylglycinyl)-4-[2-(4-pyridinyl)ethyl]piperazine (350 mg, 32%) as an off white solid.

Melting Point=75–80° C.

IR (thin film)

1H NMR (CDCl$_3$)

| Analysis for C$_{28}$H$_{29}$N$_4$O$_3$: | |
| --- | --- |
| Calcd: | C, 50.12; H, 5.06; N, 7.54; |
| Found: | C, 49.81; H, 5.33; N, 7.39. |

HPLC Analysis (Method B): >99% t$_r$=12.4 min.

Example 3a 1-(Indole-6-carbonyl-D-phenylglycinyl)-4-[2-(4-pyridinyl)ethyl]piperazine Dihydrochloride.

Prepared from 1-(indole-6-carbonyl-D-phenylglycinyl)-4-[2-(4-pyridinyl)ethyl]piperazine using Method I-D (but using dichloromethane as the initial solvent).

1H NMR

IS-MS, m/e 468.2 (M+1)

| Analysis for C$_{28}$H$_{29}$N$_5$O$_2$.1.9 HCl.2.0 H$_2$O: | |
| --- | --- |
| Calcd: | C, 58.70; H, 6.14; N, 12.22; Cl, 11.76; |
| Found: | C, 58.86; H, 5.62; N, 12.07; Cl, 11.78. |

HPLC Analysis (Method A): 100% t$_r$=19.24 min.

Example 4

1-(3-Chloroindole-6-carbonyl-D-phenylglycinyl)-4-[2-(4-pyridinyl)ethyl]piperazine.

Prepared from 3-chloroindole-6-carboxylic acid and 1-(D-phenylglycinyl)-4-[2-(4-pyridinyl)ethyl]piperazine using Method I-C.

Melting point=100–105° C.

1H-NMR (CDCl$_3$)

API-MS, m/e 502 (M+1)

| Analysis for C$_{28}$H$_{28}$ClN$_5$O$_2$.1.2 H$_2$O: | |
| --- | --- |
| Calcd: | C, 64.23; H, 5.85; N, 13.37; |
| Found: | C, 64.38; H, 5.74; N, 13.22. |

HPLC Analysis (Method B): 97.2% t$_r$=13.8 min.

Example 4a 1-(3-Chloroindole-6-carbonyl-D-phenylglycinyl)-4-[2-(4-pyridinyl)ethyl]piperazine Dihydrochloride.

Prepared from 1-(3-chloroindole-6-carbonyl-D-phenylglycinyl)-4-[2-(4-pyridinyl)ethyl]piperazine using Method I-D (but using dichloromethane as the initial solvent).

1H NMR

IS-MS, m/e 502.1 (M+1)

| Analysis for C$_{28}$H$_{28}$ClN$_5$O$_2$.2.0 HCl.1.8 H$_2$O: | |
| --- | --- |
| Calcd: | C, 55.37; H, 5.58; N, 11.53; Cl, 17.51; |
| Found: | C, 55.03; H, 5.34; N, 11.30; Cl, 17.26. |

HPLC Analysis (Method A): 100% t$_r$=24.55 min.

Example 5

1-(5-Chloroindole-2-carbonyl-D-phenylglycinyl)-4-[2-(4-pyridinyl)ethyl]piperazine.

Prepared from 5-chloroindole-2-carboxylic acid and 1-(D-phenylglycinyl)-4-(2-(4-pyridinyl)ethyl]piperazine using Method I-C.

Melting Point=106–110° C.

IR (thin film)

1H-NMR (CDCl$_3$)

API-MS, m/e=502 (M+1)

HPLC Analysis (Method B): 88.7% t$_r$=14.9 min.

Example 6
1-(Indole-2-carbonyl-D-phenylglycinyl)-4-[2-(4-pyridinyl)ethyl]piperazine.

Prepared from indole-2-carboxylic acid and 1-(D-phenylglycinyl)-4-[2-(4-pyridinyl)ethyl]piperazine using Method I-C.

Melting point=95–100° C.
1H-NMR (CDCl$_3$)
IR (thin film)
API-MS, m/e 468 (M+1)

| Analysis for C$_{28}$H$_{29}$N$_5$O$_2$.1.7 H$_2$O: | |
|---|---|
| Calcd: | C, 67.51; H, 6.55; N, 14.06; |
| Found: | C, 67.00; H, 6.10; N, 14.02. |

HPLC Analysis (Method B): 96.5% t$_r$=13.5 min.

Example 7
1-(3-Methylindole-6-carbonyl-D-phenylglycinyl)-4-[2-(4-pyridinyl)ethyl]piperazine.

Prepared from 3-methylindole-6-carboxylic acid and 1-(D-phenylglycinyl)-4-[2-(4-pyridinyl)ethyl]piperazine using Method I-C.

Melting point=62–65° C.
1H-NMR (CDCl$_3$)
IR (thin film)
API-MS, m/e 482 (M+1)

| Analysis for C$_{29}$H$_{31}$N$_5$O$_2$.1.6 H$_2$O: | |
|---|---|
| Calcd: | C, 68.24; H, 6.75; N, 13.72; |
| Found: | C, 68.25; H, 6.66; N, 13.78. |

HPLC Analysis (Method B): 93.6% t$_r$=13.3 min.

Example 8
1-(4-Methoxybenzoyl-D-phenylglycinyl)-4-(2-(2-pyridinyl)ethyl]piperazine.

Prepared from 4-methoxybenzoyl chloride and 1-(D-phenylglycinyl)-4-[2-(2-pyridinyl)ethyl]piperazine using Method I-B.

Melting point=168–180° C.
$[\alpha]^{25}_D$ –87.7 (c 1.00, methanol)
1H-NMR (CD$_3$OD)
CI-MS, m/e=459 (M+1)

| Analysis for C$_{27}$H$_{30}$N$_4$O$_2$.2.0 HCl.0.9 H$_2$O: | |
|---|---|
| Calcd: | C, 59.21; H, 6.22; N, 10.23; Cl, 12.95, |
| Found: | C, 58.88; H, 6.25; N, 10.19; Cl, 13.26. |

HPLC Analysis (Method B): 97.5% t$_r$=12.2 min.

Example 9
1-(3-Chloroindole-6-carbonyl-D-phenylglycinyl)-4-[2-(2-pyridinyl)ethyl]piperazine.

Prepared from 3-chloroindole-6-carboxylic acid and 1-(D-phenylglycinyl)-4-[2-(2-pyridinyl)ethyl]piperazine using Method I-C.

Melting point=93–96° C.
$[\alpha]^{25}_D$ –72.4 (c 0.61, chloroform)
1H-NMR (CDCl$_3$)
CI-MS, m/e=502 (M+1)

| Analysis for C$_{28}$H$_{28}$N$_5$O$_2$.0.4 H$_2$O: | |
|---|---|
| Calcd: | C, 66.04; H, 5.07; N, 13.75; Cl, 6.96; |
| Found: | C, 65.94; H, 5.61; N, 13.74; Cl, 6.91. |

HPLC Analysis (Method B): 98.3% t$_r$=14.1 min.

Example 10
1-(Indole-6-carbonyl-D-phenylglycinyl)-4-[2-(2-pyridinyl)ethyl]piperazine.

Prepared from indole-6-carboxylic acid and 1-(D-phenylglycinyl)-4-[2-(2-pyridinyl)ethyl]piperazine using Method I-C.

Melting point=73–78° C.
$[\alpha]^{25}_D$ –90-9 (c 0.25, chloroform)
1H-NMR (CDCl$_3$)
CI-MS, m/e 468 (M+1)

| Analysis for C$_{28}$H$_{28}$N$_5$O$_2$.0.6 H$_2$O: | |
|---|---|
| Calcd: | C, 70.30; H, 6.36; N, 14.64; |
| Found: | C, 70.39; H, 6.30; N, 14.62. |

HPLC Analysis (Method B): 98.3% t$_r$=14.1 min.

Example 11
1-[4-Methoxybenzoyl-D,L-(pyridin-2-yl)glycinyl]-4-[2-(4-pyridinyl)ethyl]piperazine Trihydrochloride.

Prepared from 4-methoxybenzoic acid and 1-[D,L-(pyridin-2-yl)glycinyl]-4-[2-(4-pyridinyl)ethyl]piperazine using Method I-C.

1H-NMR
IS-MS, m/e 460.3 (M+1)

| Analysis for C$_{26}$H$_{29}$N$_5$O$_3$.3.5 HCl.4 H$_2$O: | |
|---|---|
| Calcd: | C, 47.37; H, 6.19; N, 10.62; |
| Found: | C, 47.17; H, 5.75; N, 10.56. |

HPLC Analysis (Method A): 100% t$_r$=10.48 min.

Example 12
1-[3-Chloroindole-6-carbonyl-D,L-(pyridin-2-yl)glycinyl]-4-[2-(4-pyridinyl)ethyl]piperazine Trihydrochloride.

Prepared from 3-chloroindole-6-carboxylic acid and 1-[D,L-(pyridin-2-yl)glycinyl]-4-[2-(4-pyridinyl)ethyl]-piperazine using Method I-C.

1H-NMR
IS-MS, m/e 503.5 (M+1)

| Analysis for C$_{27}$H$_{27}$N$_6$O$_2$Cl.3 HCl.5 H$_2$O: | |
|---|---|
| Calcd: | C, 46.16; H, 5.74; N, 11.96; Cl, 20.19; |
| Found: | C, 46.10; H, 5.59; N, 11.68; Cl, 20.29. |

HPLC Analysis (Method A): 99% t$_r$=18.64 min.

Example 13
1-[3-Methylindole-6-carbonyl-D,L-(pyridin-2-yl)glycinyl]-4-[2-(4-pyridinyl)ethyl]piperazine.

Prepared from 3-methylindole-6-carboxylic acid and 1-[D,L-(pyridin-2-yl)glycinyl]-4-[2-(4-pyridinyl)ethyl]-piperazine using Method I-C.
1H-NMR
IS-MS, m/e 483.5 (M+1)
HPLC Analysis (Method A): 99% $t_r$=16.14 min.

Example 14
1-[Indole-6-carbonyl-D,L-(pyridin-2-yl)glycinyl]-4-[2-(4-pyridinyl)ethyl]piperazine.

Prepared from indole-6-carboxylic acid and 1-[D,L-(pyridin-2-yl)glycinyl]-4-[2-(4-pyridinyl)ethyl]piperazine using Method I-C.
IS-MS, m/e 469.3 (M+1)
HPLC Analysis (Method A): 100% $t_r$=12.87 min.

Example 15
1-(Indole-6-carbonyl-D-phenylglycinyl)-4-[2-(3-pyridinyl)ethyl]piperazine.

Prepared from indole-6-carboxylic acid and 1-(D-phenylglycinyl)-4-[2-(3-pyridinyl)ethyl]piperazine using Method I-C.
Melting point=82–87° C.
$[\alpha]^{25}_D$ –116.0 (c 0.25, methanol)
IR (thin film)
1H-NMR (CDCl$_3$)
API-MS, m/e=468 (M+1)

| Analysis for $C_{28}H_{29}N_5O_2$·1.25 H$_2$O: | |
|---|---|
| Calcd: | C, 68.62; H, 6.48; N, 14.29; |
| Found: | C, 68.49; H, 6.39; N, 14.13. |

HPLC Analysis (Method B): >99% $t_r$=12.3 min.

Example 16
1-(Indole-6-carbonyl-D-phenylglycinyl)-4-[2-(2-pyrazinyl)ethyl]piperazine.

Prepared from indole-6-carboxylic acid and 1-(D-phenylglycinyl)-4-[2-(2-pyrazinyl)ethyl]piperazine using Method I-C.
Melting Point=53–58° C.
$[\alpha]^{25}_D$ –91.4 (c 0.23, chloroform)
1H-NMR (CDCl$_3$)
IR (thin film)
API-MS, m/e 469 (M+1)

| Analysis for $C_{27}H_{28}N_6O_2$·1.6 H$_2$O: | |
|---|---|
| Calcd: | C, 65.20; H, 6.32; N, 16.90; |
| Found: | C, 65.49; H, 6.02; N, 16.54. |

HPLC Analysis (Method B): 98.5% $t_r$=13.6 min.

Example 17
1-(Indole-6-carbonyl-D-phenylglycinyl)-4-[2-(1-imidazolyl)ethyl]piperazine.

Prepared from indole-6-carboxylic acid and 1-(D-phenylglycinyl)-4-[2-(1-imidazolyl)ethyl]piperazine using Method I-C.
1H-NMR
IS-MS, m/e 457.3 (M+1)

| Analysis for $C_{26}H_{28}N_6O_2$·1.1 H$_2$O: | |
|---|---|
| Calcd: | C, 65.55; H, 6.39; N, 17.64; |
| Found: | C, 66.01; H, 6.23; N, 17.14. |

HPLC Analysis (Method A): 99% $t_r$=19.66 min.

Example 18
1-(Indole-6-carbonyl-D-phenylglycinyl)-4-[2-(1-pyrazolyl)ethyl]piperazine.

Prepared from indole-6-carboxylic acid and 1-(D-phenylglycinyl)-4-[2-(1-pyrazolyl)ethyl]piperazine using Method I-C.
1H-NMR
IS-MS, m/e 457.2 (M+1)

| Analysis for $C_{26}H_{28}N_6O_2$·1.3 H$_2$O: | |
|---|---|
| Calcd: | C, 65.06; H, 6.43; N, 17.51; |
| Found: | C, 65.39; H, 6.53; N, 16.98. |

HPLC Analysis (Method A):>97% $t_r$=22.98 min.

Example 19
1-(Indole-6-carbonyl-D-phenylglycinyl)-4-[2-(4-imidazolyl)ethyl]piperazine Dihydrochloride.

Prepared from indole-6-carboxylic acid and 1-(D-phenylglycinyl)-4-[2-(4-imidazolyl)ethyl]piperazine using Method I-C.
1H-NMR
IS-MS, m/e 457.3 (M+1)

| Analysis for $C_{26}H_{28}N_6O_2$·2.1 HCl·4.0 H$_2$O: | |
|---|---|
| Calcd: | C, 51.60; H, 6.35; N, 13.89; Cl, 12.30; |
| Found: | C, 51.82; H, 6.04; N, 13.56; Cl, 12.12. |

HPLC Analysis (Method A): 94% $t_r$=17.78 min.

Example 20
1-(Indole-6-carbonyl-D-phenylglycinyl)-4-[2-(4-pyrazolyl)ethyl]piperazine Hydrochloride.

Prepared from indole-6-carboxylic acid and 1-(D-phenylglycinyl)-4-[2-(4-pyrazolyl)ethyl]piperazine using Method I-C.
1H-NMR
IS-MS, m/e 457.3 (M+1)

| Analysis for $C_{26}H_{28}N_6O_2$·1.3 HCl·1.75 H$_2$O: | |
|---|---|
| Calcd: | C, 58.32; H, 6.17; N, 15.70; Cl, 8.61; |
| Found: | C, 58.31; H, 5.72; N, 15.48; Cl, 8.37. |

HPLC Analysis (Method A): >98% $t_r$=19.95 min.

Example 21
1-(Indole-6-carbonyl-D-phenylglycinyl)-4-[2-(3-pyridazinyl)ethyl]piperazine.

Prepared from indole-6-carboxylic acid and 1-(D-phenylglycinyl)-4-[2-(3-pyridazinyl)ethyl]piperazine using Method I-C.

Melting Point=219–222° C. with decomposition
1H NMR (CDCl$_3$)
[α]$^{25}_D$ −53.9° (c 0.25, dimethyl sulfoxide)
API-MS, m/e=469 (M+1)
HPLC Analysis (Method B): >99% t$_r$=12.8 min.

Example 22

1-[4-Methoxybenzoyl-D,L-(2-methoxyphenyl)glycinyl]-4-[2-(4-pyridinyl)ethyl]piperazine.

Prepared from 4-methoxybenzoic acid and 1-[D,L-(2-methoxyphenyl)glycinyl]-4-[2-(4-pyridinyl)ethyl]piperazine using Method I-C.
1H-NMR
IS-MS, m/e 489.1 (M+1)

| Analysis for C$_{28}$H$_{32}$N$_4$O$_4$.0.5 H$_2$O: | |
|---|---|
| Calcd: | C, 67.59; H, 6.68; N, 11.26; |
| Found: | C, 67.57; H, 6.49; N, 11.11. |

HPLC Analysis (Method A): 97.2% t$_r$=16.02 min.

Example 23

1-[Indole-6-carbonyl-D,L-(2-methoxyphenyl)glycinyl]-4-[2-(4-pyridinyl)ethyl]piperazine Dihydrochloride.

Prepared from indole-6-carboxylic acid and 1-[D,L-(2-methoxyphenyl)glycinyl]-4-[2-(4-pyridinyl)ethyl]piperazine using Method I-C, followed by Method I-D.
1H-NMR
IS-MS, m/e 498.0 (M+1)

| Analysis for C$_{29}$H$_{31}$N$_5$O$_3$.2.1 HCl.2.5 H$_2$O: | |
|---|---|
| Calcd: | C, 56.25; H, 6.20; N, 11.31; Cl, 12.02; |
| Found: | C, 56.56; H, 5.83; N, 11.21; Cl, 12.13. |

HPLC Analysis (Method A): 100% t$_r$=17.24 min.

Methods for Examples 24–25

The compounds of Examples 24 and 25 were prepared by coupling Boc-D-4-carboxamidophenylglycine to the appropriate amine with EDCI/HOAt (similar to Method C—C), deprotection with TFA/DCM (similar to Method D-B) and coupling to 3-amino-4-chlorobenzoic acid with EDCI/HOAt (similar to Method I-C).

Example 24

1-[3-Amino-4-chlorobenzoyl-D-(4-carboxamidophenyl)glycinyl]-4-(2-phenylethyl)piperazine.
HPLC (Method C) rt 11.1 min.
LCMS M+1 521.
NMR Example 25

1-[3-Amino-4-chlorobenzoyl-D-4-carboxamidophenylglycinyl]-4-benzylpiperazine.
HPLC (Method C) rt 11.4 min.
LCMS M+1 512.
NMR Example 26

1-[Indole-6-carbonyl-D-(4-carboxyphenyl)glycinyl]-4-(1-methylpiperidin-4-yl)piperazine.

By coupling of Boc-D-4-carboxymethylphenylglycine with 1-(1-methylpiperidin-4-yl)piperazine using HOAt and EDCI (similar to Method C—C), followed by TFA deprotection (similar to Method D-B), coupling to indole-6-carboxylic acid using HOAt and EDCI (similar to Method I-C) followed by hydrolysis of the methyl ester with lithium hydroxide.
HPLC (Method C) rt, 6.05 min
LCMS M+1 504
Nmr.

Example 27

1-(4-Methoxybenzoyl-D-phenylglycinyl)-4-(4-piperidinylmethyl)piperazine Trifluoroacetate.
Preparation of Starting Materials
1-Boc-isonipecotic Acid.

Isonipecotic acid (15.0 g, 116 mmol) was dissolved in THF (300 mL), water (150 mL) and 6 N NaOH (40 mL), Di-tert-butyl dicarbonate (26.6 g, 122 mmol) was added and the mixture stirred overnight. The mixture was diluted with water and ethyl acetate, and the layers separated. The water layers were extracted with ethyl acetate, and the organic layers discarded. The water layer was diluted with KHSO$_4$ (2 N, pH-4) and extracted with ethyl acetate. The organic layer was washed with brine, dried (Na$_2$SO$_4$), filtered and concentrated to provide 1-Boc-isonipecotic acid (23.9 g, 90%) as a white solid.
1H-NMR (CDCl$_3$)
API-MS, m/e=230 (M+1)
1-Boc-piperidine-4-methanol.

1-Boc-isonipecotic acid (10.0 g, 214 mmol) was dissolved in THF (400 mL) and cooled to 0° C. A solution of BH$_3$-THF (180 mL, 1 N in THF, 180 mmol) was added slowly. The mixture stirred for 1 h at 0° C. and was allowed to warm to room temperature for 12 h. The mixture was carefully quenched with water and diluted with ethyl acetate. The water layer was extracted with ethyl acetate. The organic layers were combined, washed with brine, dried (Na$_2$SO$_4$), filtered and concentrated to provide 1-Boc-piperidine-4-methanol (7.98 g, 85%) as a white solid.
1H-NMR (CDCl$_3$)
API-MS, m/e=220 (M+1)
1-Boc-piperidine-4- carboxaldehyde.

Dimethyl sulfoxide (3.5 mL, 48.7 mmol) was dissolved in dichloromethane (100 mL) and was cooled to −78° C. Oxalyl chloride (3.65 mL, 41.8 mmol) was added. The mixture stirred for 30 min. To this solution was added a solution of 1-Boc-piperidine-4-methanol (7.5 g, 34.8 mmol) in dichloromethane (15 mL), and the mixture stirred for 1 h. Triethylamine (9.7 mL, 69.6 mmol) was added slowly and the mixture stirred at −78° C. for 30 min and warmed to room temperature over the course of 1 h. The mixture was diluted with water and the layers separated. The water layer was extracted with dichloromethane and the organic layers combined, dried (Na$_2$SO$_4$), filtered and concentrated to provide 1-Boc-piperidine-4-carboxaldehyde (6.75 g, 91%) as a yellow oil.
1H-NMR (CDCl$_3$)
API-MS, m/e=214 (M+1)
1-(4-Methoxybenzoyl-D-phenylglycinyl)-4-(1-Boc-piperidin-4-ylmethyl)piperazine.

Prepared from 1-(4-methoxybenzoyl-D-phenylglycinyl)piperazine trifluoroacetate and 1-Boc-piperidine-4-carboxaldehyde using Method I-A (but using sodium triacetoxyborohydride in 1,2-dichloroethane)(85%).
1H-NMR (CDCl$_3$)
1-(4-Methoxybenzoyl-D-phenylglycinyl)-4-(4-piperidinylmethyl)piperazine trifluoroacetate.

Prepared from 1-(4-methoxybenzoyl-D-phenylglycinyl)-4-(1-Boc-piperidin-4-ylmethyl)piperazine using Method H-A (90%).

Melting Point=70–72° C. with decomposition
IR (KBr)
1H-NMR (CD$_3$OD)
API-MS, m/e=451 (M+1)

| Analysis for C$_{26}$H$_{34}$N$_4$O$_3$.2.5 TFA.0.4 H$_2$O: | |
|---|---|
| Calcd: | C, 50.12; H, 5.06; N, 7.54; |
| Found: | C, 49.81; H, 5.33; N, 7.39. |

HPLC Analysis (Method B): 97.1% RT=14.3 min.

Methods for Examples 28–29

Unless otherwise indicated, using Method I-A, the title compounds were prepared from 1-(4-methoxybenzoyl-D-phenylglycinyl)-4-(4-piperidinylmethyl)piperazine trifluoroacetate and the indicated aldehyde or ketone.

Example 28
1-(4-Methoxybenzoyl-D-phenylglycinyl)-4-(1-methylpiperidin-4-ylmethyl)piperazine.
Prepared from paraformaldehyde (56%).
IR (KBr)
1H-NMR (CD$_3$OD)
CI-MS, m/e=465 (M+1)

Example 29
1-(4-Methoxybenzoyl-D-phenylglycinyl)-4-(1-isopropylpiperidin-4-ylmethyl)piperazine Trihydrochloride.
Prepared from acetone using Method I-A, followed by Method I-D (but using methanol in place of ether/dichloromethane) (72%).
Melting Point=172–180° C. with decomposition
IR (KBr)
1H-NMR (CD$_3$OD)
CI-MS, m/e=493 (M+1)

| Analysis for C$_{29}$H$_{40}$N$_4$O$_3$.3 HCl: | |
|---|---|
| Calcd: | C, 55.85; H, 7.34; N, 8.98; |
| Found: | C, 55.63; H, 7.32; N, 8.66. |

HPLC Analysis (Method B): 98.2% RT=14.4 min.

Example 30
1-(4-Methoxybenzoyl-D-phenylglycinyl)-4-(2-cyclopentylethyl)piperazine
Preparation of Starting Materials:
Cyclopentylacetaldehyde.
Prepared from 2-cyclopentylethanol using the Dess-Martin oxidation (Dess, D. B.; Martin, J. C.; J. Am. Chem. Soc., 1991, 113, 7277). The aldehyde was used with trace amounts of ether and methylene chloride present due to volatility of product.
1H NMR (CDCl$_3$)
1-(4-Methoxybenzoyl-D-phenylglycinyl)-4-(2-cyclopentylethyl)piperazine.
Prepared from cyclopentylacetaldehyde using Method I-A (58%).
1H NMR (CDCl$_3$)

Example 30A
1-(4-Methoxybenzoyl-D-phenylglycinyl)-4-(2-cyclopentylethyl)piperazine Hydrochloride Hydrate.
Method I-D
To a stirred solution of 1-(4-methoxybenzyl-D-phenylglycinyl)-4-(2-cyclopentylethyl)piperazine (260 mg, 0.58 mmol) in ether (10 mL) and methylene chloride (1 mL) was added hydrogen chloride as a 2 N solution in ether (about 2 mL), and the resulting precipitate was filtered to give 1-(4-methoxybenzoyl-D-phenylglycinyl)-4-(2-cyclopentylethyl)piperazine hydrochloride as a pale yellow solid.
1H NMR (CD$_3$OD)
IS-MS, m/e=450 (M+1)

| Analysis for C$_{27}$H$_{35}$N$_3$O$_3$.HCl.0.5 H$_2$O: | |
|---|---|
| Calcd: | C, 65.51; H, 7.53; N, 8.49; |
| Found: | C, 65.67; H, 7.58; N, 8.13. |

HPLC Analysis (Method D): >99%, RT=15.84
Melting Point=190–192° C.

Example 31
1-(4-Methoxybenzoyl-D-phenylglycinyl)-4-(3-pyrrolidinyl) piperazine Trifluoroacetate.
Preparation of Starting Materials
(R)-(+)-1-Boc-3-pyrrolidinol.
To a stirred solution of (R)-(+)-3-pyrrolidinol (2 g, 22.96 mmol) in tetrahydrofuran (60 mL) and water (30 mL) was added di-tert-butyl dicarbonate (5.27 g, 24.15 mmol) and 3 N sodium hydroxide (16 mL), and the resulting solution was stirred for 6 h. Another portion of di-tert-butyl dicarbonate (0.74 g, 0.34 mmol) was added and the solution was stirred overnight. The reaction was diluted with water (40 mL) and extracted with ethyl acetate (2×150 mL). The combined organic extracts were washed with 2 N potassium hydrogen sulfate (200 mL), saturated sodium bicarbonate (2×150 mL), brine (150 mL) and dried over magnesium sulfate. Removal of solvent in vacuo gave (R)-(+)-1-Boc-3-pyrrolidinol (4.21 g, 98%) as a yellow oil.
1H-NMR (CDCl$_3$)
1-Boc-3-pyrrolidinone.
Prepared from (R)-(+)-1-Boc-3-pyrrolidinol using the Dess-Martin oxidation (Dess, D. B.; Martin, J. C.; J. Am. Chem. Soc., 1991, 113, 7277)(85%).
1H NMR (CDCl$_3$)
1-(4-Methoxybenzyl-D-phenylglycinyl)-4-(1-Boc-3-pyrrolidinyl)piperazine.
Prepared from 1-(4-methoxybenzyl-D-phenylglycinyl) piperazine trifluoroacetate and 1-Boc-3-pyrrolidinone using Method I-A (69%).
1H NMR (CDCl$_3$)
1-(4-Methoxybenzoyl-D-phenylglycinyl)-4-(3-pyrrolidinyl) piperazine Trifluoroacetate.
Prepared from 1-(4-methoxybenzoyl-D-phenylglycinyl)-4-(1-Boc-3-pyrrolidinyl)piperazine using Method H-A.
1H NMR (CD$_3$OD)

Methods for Examples 32–33

Using Method I-A (but using sodium triacetoxyborohydride in 1,2-dichloroethane), the title compounds were prepared from 1-(4-methoxybenzoyl-D-phenylglycinyl)-4-(3-pyrrolidinyl)piperazine trifluoroacetate and the indicated aldehyde or ketone.

Example 32
1-(4-Methoxybenzoyl-D-phenylglycinyl)-4-(1-methylpyrrolidin-3-yl)piperazine.
Prepared from paraformaldehyde (20%).
1H-NMR (CDCl$_3$)

Example 33
1-(4-Methoxybenzoyl-D-phenylglycinyl)-4-(1-isopropylpyrrolidin-3-yl)piperazine.
Prepared from acetone (59%).
1H-NMR (CDCl$_3$)

Methods for Examples 34–46

Unless otherwise indicated, the products of Examples 34–46 were obtained from 1-(4-methoxybenzoyl-D-phenylglycinyl)piperazine and the indicated aldehyde or ketone using Method I-A.

Example 34
1-(4-Methoxybenzoyl-D-phenylglycinyl)-4-(2-pyridylmethyl)piperazine.
Prepared from 2-pyridinecarboxaldehyde (48%).
1H-NMR
IS-MS, m/e 444.9 (M+1)
Analytical RPHPLC, Method A, RT=21.70 min (100%)

Example 35
1-(4-Methoxybenzoyl-D-phenylglycinyl)-4-(3-pyridylmethyl)piperazine.
Prepared from 3-pyridinecarboxaldehyde (42%).
1H-NMR
IS-MS, m/e 444.9 (M+1)
Analytical RPHPLC, Method A, RT=17.84 min (99%)

Example 36
1-(4-Methoxybenzoyl-D-phenylglycinyl)-4-(4-pyridylmethyl)piperazine.
Prepared from 4-pyridinecarboxaldehyde (45%).
1H-NMR
IS-MS, m/e 444.9 (M+1)
Analytical RPHPLC, Method A, RT=18.36 min (99%)

Example 37
1-(4-Methoxybenzoyl-D-phenylglycinyl)-4-(3-pentyl)piperazine.
Prepared from 3-pentanone (88%).
1H-NMR
IS-MS, m/e 424.0 (M+1)
Analytical RPHPLC, Method A, RT=23.62 min (100%)

Example 38
1-(4-Methoxybenzoyl-D-phenylglycinyl)-4-cyclopentylpiperazine.
Prepared from cyclopentanone (95%).
1H-NMR
IS-MS, m/e 422.0 (M+1)
Analytical RPHPLC, Method A, RT=20.76 min (100%)

Example 39
1-(4-Methoxybenzoyl-D-phenylglycinyl)-4-(4-methylcyclohexyl)piperazine.
Prepared from 4-methylcyclohexanone (46%).
1H-NMR
IS-MS, m/e 450.0 (M+1)
Analytical RPHPLC, Method A, RT=27.07 min (isomer 1), 27.74 min (isomer 2).

Example 40
1-(4-Methoxybenzoyl-D-phenylglycinyl)-4-(tetrahydrothiopyran-4-yl)piperazine.
Prepared from tetrahydro-4H-thiopyran-4-one (86%).
1H-NMR
IS-MS, m/e 453.9 (M+1)
Analytical RPHPLC, Method A, RT=22.96 min (100%)

Example 41
1-(4-Methoxybenzoyl-D-phenylglycinyl)-4-(2-indanyl)piperazine.
Prepared from 2-indanone (92%).
1H-NMR
IS-MS, m/e 469.9 (M+1)
Analytical RPHPLC, Method A, RT=26.32 min (100%)

Example 42
1-(4-Methoxybenzoyl-D-phenylglycinyl)-4-benzylpiperazine. Prepared from benzaldehyde (87%).
1H-NMR
IS-MS, m/e 444.0 (M+1)
Analytical RPHPLC, Method A, RT 25.78 min (96%)

Example 43
1-(4-Methoxybenzoyl-D-phenylglycinyl)-4-(cyclohexylmethyl)piperazine.
Prepared from cyclohexanecarboxaldehyde (86%).
1H-NMR
IS-MS, m/e 450.2 (M+1)
Analytical RPHPLC, Method A, RT=28.07 min (94%)

Example 44
1-(4-Methoxybenzoyl-D-phenylglycinyl)-4-(4-heptyl)piperazine.
Prepared from 4-heptanone (89%).
1H-NMR
IS-MS, m/e 452.0 (M+1)
Analytical RPHPLC, Method A, RT=29.62 min (94%)

Example 45
1-(4-Methoxybenzoyl-D-phenylglycinyl)-4-(4-pyranyl)piperazine.
Prepared from pyran-4-one (95%).
1H-NMR
IS-MS, m/e 437.9 (M+i)
Analytical RPHPLC, Method A, RT=18.46 min (97.5%)

Example 46
1-(4-Methoxybenzoyl-D-phenylglycinyl)-4-cyclohexylpiperazine. Prepared from cyclohexanone (quantitative).
1H-NMR
IS-MS, m/e 436.0 (M+1)
Analytical RPHPLC, Method A, RT=23.43 min (100%)

Examples 47–50
Preparation of Starting Materials
1-(Cbz-D-Phenylglycinyl)piperazine.
Prepared from 1-(Cbz-D-phenylglycinyl)-4-Boc-piperazine using Method H-A. The crude product was dissolved in ethyl acetate and washed with satd aq. NaHCO$_3$, followed by brine, then dried with MgSO$_4$, filtered and concentrated in vacuo (85%).
1H-NMR
IS-MS, m/e 354.2 (M+1)

| Analysis for C₂₀H₂₃N₃O₃.0.2 H₂O: | |
|---|---|
| Calcd: | C, 67.28; H, 6.61; N, 11.77; |
| Found: | C, 67.10; H, 6.46; N, 11.63. |

1-(Cbz-D-phenylglycinyl)-4-(1-methylpiperidin-4-yl)piperazine.

Prepared from (Cbz-D-phenylglycinyl)piperazine and 1-methylpiperidin-4-one using Method I-A (but using sodium triacetoxyborohydride in 1,2-dichloroethane)(49%).
1H—NMR
IS-MS, m/e 451.3 (M+1)

| Analysis for C₂₆H₃₄N₄O₃: | |
|---|---|
| Calcd: | C, 69.31; H, 7.61; N, 12.43; |
| Found: | C, 69.36; H, 7.71; N, 13.14. |

1-D-Phenylglycinyl-4-(1-methylpiperidin-4-yl)piperazine Dihydrochloride.

To a stirring suspension of 5% Pd/C (0.6 g) in ethanol (25 mL) under nitrogen was added a solution of 1-(Cbz-D-phenylglycinyl)-4-(1-methylpiperidin-4-yl)piperazine (2.6 g, 5.77 mmol) and acetic acid (1.6 mL) in ethanol (50 mL). The flask was placed under vacuum and the atmosphere was replaced with hydrogen (balloon). After 4 h, diatomaceous earth was added and the mixture was filtered through a pad of diatomaceous earth and concentrated in vacuo. The residue was dissolved in ethyl acetate and HCl gas was bubbled through the stirring solution to precipitate the dihydrochloride salt. The mixture was filtered and the solid was dried in vacuo to give 2.6 g (quantitative) of the title compound.
1H-NMR
IS-MS, m/e 317.3 (M+1)

1-Boc-D-Phenylglycinyl-4-(1-methylpiperidin-4-yl)piperazine.

Boc-D-Phg-OH (40.0 g, 159.2 mmol) and 1-(1-methylpiperidin-4-yl)piperazine (32.1 g, 175.1 mmol) were slurried in anhydrous dichloromethane (1.5 L) under N₂. The mixture was then cooled to −15° C. in an ice/MeOH bath. Triethylamine (26.6 mL, 191.0 mmol) was added slowly, maintaining the temperature at −15° C., followed by slow addition of diethyl cyanophosphonate (29.0 mL, 191.0 mmol), again maintaining temp at −15° C. The reaction mixture was allowed to warm to room temperature overnight. The reaction was then quenched with the addition of satd NaHCO₃ (500 mL), and the layers were separated. The aqueous layer was then extracted with dichloromethane (3×1 L). The organic layers were combined, dried over Na₂SO₄, filtered and concentrated in vacuo to give a crude oil. Purification using (Biotage) Flash Chromatography with 7.5% (2 M NH₃ in MeOH) in THF gave 53.6 g (81%) of the title compound.

¹H NMR (DMSO-d₆) δ 7.33 (m, 5H), 7.12 (d, J=8.1 Hz, 1H), 5.53 (d, J=8.1 Hz, 1H), 3.31 (m, 5H), 2.72 (d, J=11.3 Hz, 2H), 2.3 (m, 3H), 2.09 (s, 3H), 2.03–1.86 (m, 2H), 1.76 (dt, J=9.7, 1.8 Hz, 2H), 1.56 (m, 2H), 1.36 (s, 9H)
IS-MS, m/e 416.27 (M+1).

Chiral HPLC indicated no racemization had occurred.

1-D-Phenylglycinyl-4-(1-methylpiperidin-4-yl)piperazine Trihydrochloride.

1-Boc-D-phenylglycinyl-4-(1-methylpiperidin-4-yl)piperazine (49.6 g, 119.1 mmol) was dissolved in anhydrous MeOH (1 L) and HCl (gas) was bubbled through the solution for 2 h 15 min, noting the formation of a white precipitate. The solvents were removed in vacuo to give 48.3 g (95%) of the title compound as an off-white foam.

¹H NMR (DMSO-d₆) δ 12.08 (bs, 1H), 11.03 (bs, 1H), 8.92 (bs, 2H), 8.79 (bs, 1H), 7.54 (m, 2H), 7.47 (m, 3H), 5.66 (s, 1 H), 4.49 (m, 1H), 4.26 (bd, 1H), 3.91 (bs, 2H), 3.5–2.8 (m, 9H), 2.69 (s, 3H), 2.4–1.8 (m, 4H). IS-MS, m/e 316.24 (M+1).

General Procedure:

Except as otherwise described, the product of each of Examples 47–50 was prepared from 1-(D-phenylglycinyl)-4-(1-methylpiperidin-4-yl)piperazine dihydrochloride and the indicated acid using Method I-C (with EDCI in place of DCC).

Example 47

1-(4-Methoxybenzoyl-D-phenylglycinyl)-4-(1-methylpiperidin-4-yl)piperazine. Prepared from 4-methoxybenzoic acid (19%).
1H-NMR
IS-MS, m/e 451.0 (M+1)
Analytical RPHPLC, Method A, RT=16.76 min (100%)

Example 47a 1-(4-Methoxybenzoyl-D-phenylglycinyl)-4-(1-methylpiperidin-4-yl)piperazine Dihydrochloride.

Prepared from 1-(4-methoxybenzoyl-D-phenylglycinyl)-4-(1-methylpiperidin-4-yl)piperazine using Method I-D (but using dichloromethane as the initial solvent).
1H NMR

| Analysis for C₂₈H₂₈ClN₅O₂.2.0 HCl.0.5 H₂O: | |
|---|---|
| Calcd: | C, 58.64; H, 7.00; N, 10.22; |
| Found: | C, 58.92; H, 6.79; N, 10.19. |

HPLC Analysis (Method A): 100% t$_r$=17.14 min.

Example 47

Alternative Synthesis 1-(4-Methoxybenzoyl-D-phenylglycinyl)-4-(1-methylpiperidin-4-yl)piperazine.

1-D-Phenylglycinyl-4-(1-methylpiperidin-4-yl)piperazine trihydrochloride (5.0 g, 11.7 mmol) was slurried in anhydrous dichloromethane (100 mL). To the slurry was added triethyamine (6.9 mL, 49.3 mmol), causing the solid to go into solution after approximately 15 min. p-Anisoyl chloride (2.1 mL, 14.1 mmol) was added, and the reaction stirred for 1 h. The reaction was quenched with the addition of water (100 mL), and the layers were separated. The aqueous layer was extracted with dichloromethane (3×100 mL). The aqueous layers were combined, dried over Na₂SO₄, filtered and concentrated. The crude material was purified twice using (Biotage) Flash Chromatography, eluting with 5% (NH₃ in MeOH) in dichlormethene to give 1.4 g (26%-) of the title compound.

¹H NMR (DMSO-d₆) δ 8.65 (d, J=7.7 Hz, 1H), 7.88 (d, J=8.8 Hz, 2H), 7.35 (m, 5H), 6.97 (d, J=8.8 Hz, 1H), 6.40 (d, J=7.7 Hz, 1H), 3.80 (s, 3H), 3.48 (m, 3H), 2.72 (d, J=11.3 Hz, 2H), 2.39 (m, 3H), 2.09 (s, 3H), 2.02 (m, 2H), 1.77 (dt, J=1.8, 10.2 Hz, 2H), 1.59 (d, J=11.0 Hz, 2H), 1.30 (m, 2H).
IS-MS m/e 450.26 (M+1).
[α]$_D^{20}$=−87.62 (c=0.02, MeOH).

| Analysis for C$_{26}$H$_{34}$N$_4$O$_3$.H$_2$O: | |
|---|---|
| Calcd: | C, 66.64; H, 7.74; N, 11.96; |
| Found: | C, 66.79; H, 7.41; N, 11.94. |

Example 48
1-(Indole-6-carbonyl-D-phenylglycinyl)-4-(1-methylpiperidin-4-yl)piperazine.

Prepared from indole-6-carboxylic acid (65%).
1H-NMR
IS-MS, m/e 460.2 (M+1)
Analytical RPHPLC, Method A, RT=16.68 min (100%)

Example 48a
1-(Indole-6-carbonyl-D-phenylglycinyl)-4-(1-methylpiperidin-4-yl)piperazine Dihydrochloride.

May be prepared from 1-(indole-6-carbonyl-D-phenylglycinyl)-4-(1-methylpiperidin-4-yl)piperazine using Method I-D (but using dichloromethane as the initial solvent).

Example 48 (Alternative Synthesis)
1-(Indole-6-carbonyl-D-phenylglycinyl)-4-(1-methylpiperidin-4-yl)piperazine.

Indole-6-carboxylic acid (16.0 g, 99.3 mmol) and 1-D-phenylglycinyl-4-(1-methylpiperidin-4-yl)piperazine trihydrochloride (42.3 g, 99.3 mmol) were slurried in anhydrous dichloromethane (1 L) under N$_2$. The mixture was then cooled to −15° C. in an ice/MeOH bath. Triethylamine (58.1 mL, 416.9 mmol) was added slowly, maintaining the temperature at −15° C., followed by slow addition of diethyl cyanophosphonate (18.1 mL, 119.1 mmol), maintaining the temperature at −15° C. The reaction mixture was allowed to warm to room temperature overnight. The reaction was then quenched with the addition of satd NaHCO$_3$ (500 mL), and the layers were separated. The aqueous layer was then extracted with dichloromethane (3×500 mL). The organic layers were combined, dried over Na$_2$SO$_4$, filtered and concentrated to give a crude oil. Purification was performed using (Biotage) Flash Chromatography, eluting with 8.3% (2 M NH$_3$ in MeOH) in CHCl$_3$. The product containing fractions were combined and concentrated in vacuo to give 45.1 g (99%) of the title compound.

$^1$H NMR (DMSO-d$_6$) δ 11.35 (s, 1H), 8.65 (d, J=7.7 Hz, 1H), 7.98 (s, 1H), 7.60–7.45 (m, 5H), 7.40–7.25 (m, 3H), 6.48 (t, J=2.0 Hz, 1H), 6.0 g (d, J=7.7 Hz, 1H), 3.5 (m, 3H), 2.72 (d, J=11.3 Hz, 2H), 2.40 (m, 2H), 2.09 (s, 3H), 2.05 (m, 2H), 1.77 (dt, J=1.1, 10.2 Hz, 2H), 1.59 (d, J=11.3 Hz, 2H), 1.31 (m, 2H).

$^{13}$C NMR (DMSO-d$_6$) δ 168.0, 166.4, 138.0, 135.1, 129.9, 128.4, 128.2, 128.0, 127.6, 126.6, 119.4, 118.1, 111.5, 101.2, 79.1, 60.6, 54.7, 53.7, 48.5, 48.3, 45.8, 45.4, 42.2, 27.7, 27.6.

IS-MS, m/e 459.26 (M+1).
$[\alpha]_D^{20}$=−73.08 (c=0.02, MeOH).

A portion of the free base was isolated from a chloroform—ethyl acetate solvent system as crystalline material which was birefringent by microscopy. From DSC and TGA, the material was found to be a solvate containing 0.5 mol chloroform per mol of free base. The chloroform solvate was found to have a broad endotherm about 148–158° C., followed by a sharper endotherm (peak at 194.4° C.) as the melting point of the desolvated free base.

Example 48a

Alternative Synthesis
1-(Indole-6-carbonyl-D-phenylglycinyl)-4-(1-methylpiperidin-4-yl)piperazine Hydrochloride.

To a solution of 1-(indole-6-carbonyl-D-phenylglycinyl)-4-(1-methylpiperidin-4-yl)piperazine (14.5 g, 31.6 mmol) in anhydrous dichloromethane (300 mL) and anhydrous MeOH (150 mL) at 0° C. was added HCl in Et$_2$O (32.2 mL, 32.2 mmol). After approximately 5 min, the solvents were removed in vacuo to give 15.1 g (96%) of the title compound.

$^1$H NMR (DMSO-d$_6$) δ 11.40 (s, 1H), 10.3 (bs, 1H), 8.68 (m, 1H), 7.99 (s, 1H), 7.6–7.4 (m, 5H), 7.4–7.3 (m, 3H), 6.48 (s, 1H), 6.11 (d, J=7.3 Hz, 1H), 4.08 (bs, 1H), 3.6–1.5 (bm, 15H), 2.66 (s, 3H).

IS-MS, m/e 459.26 (M+1).
$[\alpha]_D^{20}$=−83.67 (c=0.01, MeOH).

| Analysis for C$_{27}$H$_{33}$N$_5$O$_2$.1.1 HCl.1.7 H$_2$O: | |
|---|---|
| Calcd: | C, 61.03; H, 7.30; N, 13.18; Cl, 7.34; |
| Found: | C, 60.95; H, 6.91; N, 13.03; Cl, 7.00. |

The product prepared by both the method of Example 48a and Example 48a (Alternative Synthesis) was found to be the mono-hydrochloride salt and to be amorphous. Analysis by microscopy showed glassy non-birefringent particles; and analysis by DSC failed to reveal a melting point, in agreement with amorphous material. Using a microbalance flow system, the original material was cycled through a vapor pressure isotherm determination, where the material deliquesced, then allowed to deydrate. Upon dehydration, there were formed crystals which were birefringent by microscopy; and a melting point of about 174° C. was demonstrated for the newly crystallized, hygroscopic material.

Example 48b
1-(Indole-6-carbonyl-D-phenylglycinyl)-4-(1-methylpiperidin-4-yl) piperazine Difumarate.

The difumarate salt is conveniently prepared by dissolving the free base in methanol or 95% ethanol and warming to about 50° C. (for example at a concentration of 460 mg in 15 mL). Two molar equivalents of fumaric acid (for example 232.2 mg) are then added (for example, as a 0.25 M solution in methanol or as a suspension in 3 mL 95% ethanol). Following cooling and crystallization, and isolation and drying, the product is obtained as thin crystalline needles, with a sharp melting point at about 213° C. by DSC.

Example 49
1-(3-Methylindole-6-carbonyl-D-phenylglycinyl)-4-(1-methylpiperidin-4-yl)piperazine.

Prepared from 3-methylindole-6-carboxylic acid (50%).
1H-NMR
IS-MS, m/e 474.3 (M+1)
Analytical RPHPLC, Method A, RT=22.20 min (98%)

Example 50
1-(3-chloroindole-6-carbonyl-D-phenylglycinyl)-4-(1-methylpiperidin-4-yl)piperazine.
Prepared from 3-chloroindole-6-carboxylic acid (76%).
1H-NMR
IS-MS, m/e 493.9 (M+1)
Analytical RPHPLC, Method A, RT=22.66 min (100%)

Example 51
1-(3-Chloroindole-6-carbonyl-D-phenylglycinyl)-4-(4-piperidinylmethyl)piperazine Dihydrochloride.
Preparation of Starting Materials:
1-(1-Boc-piperidin-4-ylmethyl)piperazine.

To a stirring solution of 1-Boc-piperidine-4-carboxaldehyde (2.4 g, 11.3 mmol) in THF (60 mL) and acetonitrile (15 mL) was added piperazine (4.85 g, 56.3 mmol). After stirring for 5 h, sodium triacetoxyborohydride (2.87 g, 13.5 mmol) was added and the reaction was allowed to stir overnight. The next morning, the solvents were removed by rotary evaporation and the residue was dissolved in ethyl acetate, washed twice with satd aq. $NaHCO_3$, followed by water, then dried over $MgSO_4$, filtered and concentrated in vacuo. The residue was then chromatographed over silica gel, eluting with a step gradient of 2% through 15% (2 N ammonia/methanol) in dichloromethane. The product containing fractions were combined and concentrated in vacuo to give 4.03 g (48%) of the title compound.
1H-NMR
IS-MS, m/e 284.3 (M+1)
1-(Cbz-D-Phenylglycinyl)-4-(1-Boc-piperidin-4-ylmethyl)piperazine.

Prepared from Cbz-D-phenylglycine and 1-(1-Boc-piperidin-4-ylmethyl)piperazine using Method C-A. The title compound was purified by chromatography over silica gel, eluting with a step gradient of 1% to 3% (2 N ammonia/methanol in dichloromethane.
1H-NMR
IS-MS, m/e 551.3 (M+1)
1-(D-Phenylglycinyl)-4-(1-Boc-piperidin-4-ylmethyl)piperazine.

Prepared from 1-(Cbz-D-phenylglycinyl)-4-(1-Bocpiperidin-4-ylmethyl)piperazine using Method F-A.
1H-NMR
IS-MS, m/e 417.8 (M+1)
1-(3-Chloroindole-6-carbonyl-D-phenylglycinyl)-4-(4-piperidinylmethyl)piperazine Dihydrochloride.

Prepared from 3-chloroindole-6-carboxylic acid and 1-(D-phenylglycinyl)-4-(1-Boc-piperidin-4-ylmethyl)piperazine using Methods 1-C, D-B, and 1-D (using dichloromethane in place of ether/dichloromethane as an initial solvent).
1H-NMR
IS-MS, m/e 494.2 (M+1)

| Analysis for $C_{27}H_{32}N_5O_2Cl.2.2$ HCl.3.0 $H_2O$: | |
|---|---|
| Calcd: | C, 51.61; H, 6.45; N, 11.15; Cl, 18.06; |
| Found: | C, 51.40; H, 6.12; N, 11.02; Cl, 17.80. |

Analytical RPHPLC, Method A, RT=20.59 min (100%)

Example 52
1-(3-Methylindole-6-carbonyl-D-phenylglycinyl)-4-(4-piperidinylmethyl)piperazine Dihydrochloride.
Prepared from 3-methylindole-6-carboxylic acid and 1-(D-phenylglycinyl)-4-(1-Boc-piperidin-4-ylmethyl)piperazine using Methods 1-C, D-B, and 1-D (using dichloromethane in place of ether/dichloromethane as an initial solvent).
1H-NMR
IS-MS, m/e 474.2 (M+1)

| Analysis for $C_{28}H_{35}N_5O_2.2.3$ HCl.4.0 $H_2O$: | |
|---|---|
| Calcd: | C, 53.42; H, 7.25; N, 11.13; Cl, 12.95; |
| Found: | C, 53.14; H, 6.71; N, 10.99; Cl, 13.12. |

Analytical RPHPLC, Method A, RT=20.23 min (100%)

Example 53
1-[4-Chlorobenzoyl-D-phenylglycinyl]-4-benzylpiperazine Trifluoroacetate.

Boc-D-phenylglycine (753 mg, 3 mmol), TBTU (2-(1H-(benzotriazol-1-yl)-1,1,3,3-tetramethyluronium tetrafluoroborate) (963.3 mg, 3 mmol), diisopropylethylamine (894 mg, 6 mmol) and 4-benzylpiperazine (525 mg, 3 mmol) were combined in DMF (10 mL) and stirred overnight. The reaction mixture was taken into dichloromethane (25 mL) washed with water (50 mL) and evaporated to dryness.

The residue was treated with TFA (5 mL) for 1 h and the excess TFA evaporated in vacuo. Triethylamine (1 mL) was added and evaporated in vacuo. This mixture was then divided into three equal parts. One part was then treated with a mixture of 4-chlorobenzoic acid (156.5 mg, 1 mmol), HOBt (148.5 mg, 1.1 mmol) and EDCI (191 mg, 1 mmol) in DMF (3 mL) that had been stirred for 5 min. The reaction mixture was stirred overnight, diluted with water and acetonitile, and applied directly for purification by preparative RPHPLC to give the title compound, (120 mg).
1H-NMR By similar methods to those described in Example 53 the following compounds were prepared.

Example 54
1-[4-Chlorobenzoyl-D-phenylglycinyl]-4-(2-phenethyl)piperazine Trifluoroacetate.
1H-NMR
MS MALDI TOF M+1=462

Example 55
1-[4-Chlorobenzoyl-D-phenylglycinyl]-4-(cyclohexylmethyl)piperazine Trifluoroacetate.
1H-NMR
MS MALDI TOF M+1=454

Example 56
1-[Indole-6-carbonyl-D-phenylglycinyl]-4-[2-(thiazol-2-yl)ethyl]piperazine Hydrochloride.
Prepared from 1-(D-phenylglycinyl)-4-[2-(thiazol-2-yl)ethyl]piperazine trihydrochloride and indole-6-carboxylic acid using methods substantially equivalent to Method I-C followed by Method I-D.
Melting Point 135–142° C. with decomposition.
1H NMR ($CD_3OD$).
APCI-MS, m/e=474 ($C_{26}H_{27}N_5O_2S+1$)
HPLC Analysis (Method B): 98.8% $t_r$=14.2 min.

Example 57

No Example 57

Example 58a
1-[Indole-6-carbonyl-D-phenylglycinyl]-4-[2-(3-fluoropyridin-4-yl)ethyl]piperazine.

Prepared from 1-(D-phenylglycinyl)-4-[2-(3-fluoropyridin-4-yl)ethyl]piperazine and indole-6-carboxylic acid using a method substantially equivalent to Method I-C (66%).

1H NMR (CDCl$_3$)
APCI-MS, m/e=486 (C$_{28}$H$_{28}$FN$_5$O$_2$+1).

Example 58b
1-(Indole-6-carbonyl-D-phenylglycinyl)-4-(2-(3-fluoropyridin-4-yl)ethyl]piperazine Hydrochloride.

Prepared from 1-(indole-6-carbonyl-D-phenylglycinyl)-4-[2-(3-fluoropyridin-4-yl)ethyl]piperazine using a method substantially equivalent to Method I-D (89%).

$[\alpha]^{25}_D$ −98.8° (c 0.30, methanol)
Melting Point=135–145° C. with decomposition.
1H NMR (CD$_3$OD).
APCI-MS, m/e=486 (C$_{28}$H$_{28}$FN$_5$O$_2$+1)
TLC R$_f$=0.44 (7:3 CH$_2$Cl$_2$:CMA)

| Analysis for C$_{28}$H$_{31}$N$_3$O$_4$.1.25 HCl.1.2 H$_2$O: | |
|---|---|
| Calcd: | C, 60.84; H, 5.77; N, 12.67; Cl, 8.02; |
| Found: | C, 61.14; H, 5.86; N, 12.34; Cl, 7.88. |

HPLC Analysis (Method B): 98.2% t$_r$=13.2 min.

Example 59a
1-[Indole-6-carbonyl-D-phenylglycinyl]-4-[2-(2-cyanopyridin-4-yl)ethyl]piperazine.

Method I-E 1-(D-Phenylglycinyl)-4-[2-(2-cyanopyridin-4-ylethyl) piperazine trihydrochloride (580 mg, 1.26 mmol), indole-6-carboxylic acid (205 mg, 1.26 mmol), HOBt (171 mg, 1.26 mmol), and triethylamine (0.88 mL, 6.9 mmol) were dissolved in DMF (20 mL). To this solution, DCC (390 mg, 1.89 mmol) was added, and the mixture stirred at room temperature overnight. Ethyl acetate (100 mL) and heptane (20 mL) were added and solids removed by filtration. The solvents were removed under vacuum and residue re-dissolved in toluene/ethyl acetate (200 mL, 1:1) and solids removed by filtration. The filtrate was washed with water and brine, dried (Na$_2$SO$_4$), filtered, and concentrated under vacuum to provide crude product (800 mg). The crude product was purified by chromatography (SiO$_2$, 1000:10:1–250:10:1 CH$_2$Cl$_2$:methanol:concentrated ammonium hydroxide) to provide the sub-titled compound (443 mg, 71%).

1H NMR (CDCl$_3$).
TLC=0.3 (200:10:1, CH$_2$Cl$_2$:methanol:concentrated ammonium hydroxide)

Example 59b
1-[Indole-6-carbonyl-D-phenylglycinyl]-4-[2-(2-cyanopyridin-4-yl)ethyl]piperazine Hydrochloride.

Prepared from 1-(indoyl-6-carbonyl-D-phenylglycinyl)-4-[2-(2-cyanopyridin-4-yl)ethyl]piperazine using methods substantially equivalent to those described in Method I-D, (96%).

$[\alpha]^{25}_D$ −92.0° (c 0.27, methanol)
Melting Point=156–169° C.
IR (ATR).
1H NMR (CD$_3$OD).
APCI-MS, m/e=493 (C$_{29}$H$_{28}$N$_6$O$_2$+1)

| Analysis for C$_{28}$H$_{31}$N$_3$O$_4$.1.1 HCl.0.9 H$_2$O: | |
|---|---|
| Calcd: | C, 63.44; H, 5.68; N, 15.31; Cl, 7.10; |
| Found: | C, 63.53; H, 5.68; N, 15.41; Cl, 6.88. |

HPLC Analysis (Method B): 98.9% t$_r$=15.2 min.

Example 60
1-[4-Methoxybenzoyl-D,L-(2-chlorophenyl) glycinyl]-4-(1-methylpiperidin-4-yl)piperazine Hydrochloride.

Prepared from 1-[D,L-(2-chlorophenyl)glycinyl]-4-(1-methylpiperidin-4-yl)piperazine and p-anisoyl chloride using procedures substantially equivalent to those described in Method I-B, using dichloromethane for aqueous dioxane and TEA for K$_2$CO$_3$, followed by Method I-D.

1H NMR
IS-MS, m/e 485.3 (M+1)

| Analysis for C$_{27}$H$_{32}$N$_5$O$_2$Cl.2.2 HCl.2.0 H$_2$O: | |
|---|---|
| Calcd: | C, 53.14; H, 6.31; N, 11.48; Cl, 18.59; |
| Found: | C, 53.04; H, 5.86; N, 11.36; Cl, 18.13. |

HPLC Analysis (Method A): 100% t$_r$=19.78 min.

Example 61
1-[4-Methoxybenzoyl-D-(2-chlorophenyl)glycinyl]-4-(1-methylpiperidin-4-yl)piperazine Hydrochloride.

1-[4-Methoxybenzoyl-D,L-(2-chlorophenyl)glycinyl]-4-(1-methylpiperidin-4-yl)piperazine (8.20 g, 18.16 mmol) was divided into 2 g lots and each lot was dissolved in a mixture of chloroform (1.0 mL), isopropanol (13 mL) and heptane (26 mL). These samples were then individually chromatographed using preparative chiral HPLC (Chiralcel OD, 8×34 cm, eluting with 35% isopropanol/65% heptane with 0.4% DMEA for 21 min at a flow rate of 350 mL/min). Analytical HPLC of the the racemic mixture (Chiralcel OD, 4.6×250 mm, eluting with 35% isopropanol/65% heptane with 0.4% DMEA, 1.0 mL/min, UV detection at 260 nm) revealed two peaks, baseline resolved. The fractions from the preparative HPLC runs containing the peak with the shorter retention time were combined and concentrated in vacuo to give 3.71 g of isomer 1. The fractions containing the later running isomer were combined and concentrated to give 3.80 g of isomer 2. Biological evaluation of the two samples revealed isomer 1 to be over ten times more potent than isomer 2 and on that basis, isomer 1 was tentatively assigned as the D-isomer. Isomer 1 was then chromatographed over silica gel (Biotage Quad 12/25 System, 25 mm KP-Sil [32–63 um particle size] columns, eluting with a gradient of 0–6% 2N ammonia/methanol in dichloromethane) and the product containing fractions were combined and concentrated. The residue was then redissolved in dichloromethane and to this stirring solution was added 1 M HCl in diethyl ether (4.33 mL, 4.33 mmol). The precipitate was filtered and dried in vacuo to give 2.3 g (49%) of the title compound.

1H NMR
IS-MS, m/e 485.3 (M+1)

| Analysis for $C_{26}H_{33}N_4O_3Cl.1.3$ HCl.0.5 $H_2O$: | |
| --- | --- |
| Calcd: | C, 57.68; H, 6.57; N, 10.35; Cl, 15.06; |
| Found: | C, 57.42; H, 6.76; N, 10.06; Cl, 14.89. |

Example 62

1-[Indole-6-carbonyl-D,L-(2-chlorophenyl)glycinyl]-4-(1-methylpiperidin-4-yl)piperazine Dihydrochloride.

Method I-F

To a stirring solution of D,L-(2-chlorophenyl)glycinyl]-4-(1-methylpiperidin-4-yl)piperazine (0.458 g, 1.31 mmol) in dichloromethane (5 mL) and DMF (2 mL) was added indole-6-carboxylic acid (0.233 g, 1.44 mmol). The solution was cooled to 0° C. and DEPC (0.218 mL, 1.44 mmol) was added. After 24 h, the solution was concentrated in vacuo and the residue was dissolved in 5% acetic acid/methanol and loaded onto an SCX column. The column was washed with methanol, and then the compound was eluted with 50% (2 N ammonia/methanol) in dichloromethane. The product containing fractions were combined and concentrated in vacuo. The residue was then chromatographed over silica gel, eluting with a gradient of 0–5% (2 N ammonia/methanol) in dichloromethane. Again, the product containing fractions were combined and concentrated in vacuo to give 0.6 g of off-white solid. The HCl salt was then prepared using Method I-D to give 290 mg (39%) of the title compound.

1H NMR

IS-MS, m/e 494.2 (M+1)

| Analysis for $C_{26}H_{33}N_4O_3Cl.2.2$ HCl.0.5 $H_2O$: | |
| --- | --- |
| Calcd: | C, 54.38; H, 6.35; N, 9.76; Cl, 19.76; |
| Found: | C, 54.08; H, 6.12; N, 9.59; Cl, 19.44. |

HPLC Analysis (Method A): 100% $t_r$=21.59 min.

Example 63

1-[Indole-6-carbonyl-D-(2-chlorophenyl)glycinyl]-4-(1-methylpiperidin-4-yl)piperazine Dihydrochloride.

1-[Indole-6-carbonyl-D,L-(2-chlorophenyl)glycinyl]-4-(1-methylpiperidin-4-yl)piperazine (18.8 mmol theoretical) was divided into 0.5 g lots and each lot was dissolved in a mixture of isopropanol (5 mL) and heptane (20 mL). These samples were then individually chromatographed using preparative chiral HPLC (Chiralcel OD, 8×34 cm, eluting with 30% iso-propanol/70% heptane with 0.2% DMEA for 14 min at a flow rate of 370 mL/min). Analytical HPLC of the racemic mixture (Chiralcel OD, 4.6×250 mm, eluting with 30% isopropanol/70% heptane with 0.2% DMEA, 1.0 mL/min, UV detection at 260 nm) revealed two peaks, baseline resolved. The fractions from the preparative HPLC runs containing the peak with the shorter retention time were combined and concentrated in vacuo to give 2.8 g of isomer 1. The fractions containing the later running isomer were combined and concentrated to give 2.80 g of isomer 2. Biological evaluation of the two samples revealed isomer 1 to be about 100 times more potent than isomer 2; and, on that basis, isomer 1 was tentatively assigned as the D-isomer. Isomer 1 (2.6 g) was then redissolved in dichloromethane, and to this stirring solution was added 1 M HCl in diethyl ether (5.26 mL, 5.26 mmol). The precipitate was filtered and dried in vacuo to give 244 g (48%) of the title compound.

1H NMR

IS-MS, m/e 494.0 (M+1)

| Analysis for $C_{27}H_{32}N_5O_2Cl.2.1$ HCl.0.7 $H_2O$: | |
| --- | --- |
| Calcd: | C, 59.31; H, 6.36; N, 12.81; Cl, 13.62; |
| Found: | C, 59.57; H, 6.41; N, 12.42; Cl, 13.31. |

Example 64

1-[Indole-6-carbonyl-D,L-(quinolin-8-yl)glycinyl]-4-(1-methylpiperidin-4-yl)piperazine Dihydrochloride.

Prepared from indole-6-carboxylic acid and D,L-(quinolin-8-yl)glycinyl]-4-(1-methylpiperidin-4-yl)piperazine using procedures substantially equivalent to those described in Method I-C followed by Method I-D. The final product was purified by preparative RPHPLC (Vydac C18, 90% A through 65% A; A=0.01% aq. HCl, B=acetonitrile).

1H NMR

IS-MS, m/e 511.1 (M+1)

| Analysis for $C_{30}H_{34}N_6O_2.1.9$ HCl.3.0 $H_2O$: | |
| --- | --- |
| Calcd: | C, 56.84; H, 6.66; N, 13.26; Cl, 10.63; |
| Found: | C, 56.79; H, 6.81; N, 13.12; Cl, 10.62. |

HPLC Analysis (Method A): 98.6% $t_r$=17.84 min.

Example 65

1-[3-Chloroindole-6-carbonyl-D,L-(quinolin-8-yl) glycinyl]-4-(1-methylpiperidin-4-yl)piperazine Hydrochloride.

Prepared from 3-chloroindole-6-carboxylic acid and D,L-(quinolin-8-yl)glycinyl]-4-(1-methylpiperidin-4-yl)piperazine using procedures substantially equivalent to those described in Method I-C followed by Method I-D.

1H NMR

IS-MS, m/e 545.0 (M+1)

| Analysis for $C_{30}H_{33}N_6O_2Cl.1.6$ HCl.1.5 $H_2O$: | |
| --- | --- |
| Calcd: | C, 57.15; H, 6.01; N, 13.33; Cl, 14.62; |
| Found: | C, 56.86; H, 5.64; N, 13.02; Cl, 14.37. |

HPLC Analysis (Method A): 100% $t_r$=25.08 min.

Example 66

1-[3-Methylindole-6-carbonyl-D,L-(quinolin-8-yl) glycinyl]-4-(1-methylpiperidin-4-yl)piperazine Trihydrochloride.

Prepared from 3-methylindole-6-carboxylic acid and D,L-(quinolin-8-yl)glycinyl]-4-(1-methylpiperidin-4-yl)piperazine using procedures substantially equivalent to those described in Method I-C followed by Method I-D.

1H NMR

IS-MS, m/e 525.1 (M+1)

| Analysis for $C_{31}H_{36}N_6O_2 \cdot 3.0$ HCl $\cdot 2.6$ $H_2O$: | |
|---|---|
| Calcd: | C, 54.68; H, 6.54; N, 12.34; Cl, 15.62; |
| Found: | C, 54.41; H, 6.25; N, 12.00; Cl, 15.99. |

HPLC Analysis (Method A): 99% $t_r$=23.06 min.

Example 67

1-[4-Methoxybenzoyl-D,L-(2-trifluoromethylphenyl)glycinyl]-4-(1-methylpiperidin-4-yl)piperazine Hydrochloride.

Prepared from using procedures substantially equivalent to those described in Method I-C followed by 1-D.
1H NMR
IS-MS, m/e 519.0 (M+1)
HPLC Analysis (Method A): 98% $t_r$=20.18 min.

Example 68

1-[4-Methoxybenzoyl-D-(2-trifluoromethylphenyl)glycinyl]-4-(1-methylpiperidin-4-yl)piperazine Dihydrochloride.

1-[4-Methoxybenzoyl-D,L-(2-trifluoromethylphenyl)glycinyl]-4-(1-methylpiperidin-4-yl)piperazine (6.14. g, 11.8 mmol) was divided into 0.5 g lots and each lot was dissolved in a mixture of isopropanol (20 mL) and heptane (30 mL). These samples were then individually chromatographed using preparative chiral HPLC (Chiralpak AD, 8×40 cm, eluting with 45% isopropanol/55% heptane with 0.2% DMEA for 18 min at a flow rate of 450 mL/min). Analytical HPLC of the racemic mixture (Chiralpak AD, 4.6×250 mm, eluting with 45% isopropanol/55% heptane with 0.2% DMEA, 1.0 mL/min, UV detection at 260 nm) revealed two peaks, baseline resolved. The fractions from the preparative HPLC runs containing the peak with the shorter retention time were combined and concentrated in vacuo to give 2.9 g of isomer 1. The fractions containing the later running isomer were combined and concentrated to give 2.8 g of isomer 2. Biological evaluation of the two samples revealed isomer 1 to be over 100 times more potent than isomer 2; and, on that basis, isomer 1 was tentatively assigned as the D-isomer. Isomer 1 (2.7 g) was then redissolved in dichloromethane and to this stirring solution was added 1 M HCl in diethyl ether (10.4 mL, 10.4 mmol). The precipitate was filtered and dried in vacuo to give 2.8 g (75%) of the title compound.
1H NMR
IS-MS, m/e 520.1 (M+1)

| Analysis for $C_{27}H_{33}N_4O_3F \cdot 2.1$ HCl $\cdot 1.4$ $H_2O$: | |
|---|---|
| Calcd: | C, 52.43; H, 6.14; N, 9.06; Cl, 12.04; |
| Found: | C, 52.06; H, 6.03; N, 9.41; Cl, 11.91. |

Example 69

1-[Indole-6-carbonyl-D,L-(2-trifluoromethylphenyl)glycinyl]-4-(1-methylpiperidin-4-yl)piperazine Hydrochloride.

Prepared from 1-[D,L-(2-trifluoromethylphenyl)glycinyl]-4-(1-methylpiperidin-4-yl)piperazine and 6-carboxyindole using procedures substantially equivalent to those described in Method I-C followed by 1-D.
1H NMR
IS-MS, m/e 528.0 (M+1)

| Analysis for $C_{28}H_{32}N_5O_2F_3 \cdot 1.9$ HCl $\cdot 2.5$ $H_2O$: | |
|---|---|
| Calcd: | C, 52.39; H, 6.10; N, 10.91; Cl, 10.50; |
| Found: | C, 52.12; H, 5.61; N, 10.71; Cl, 10.63. |

HPLC Analysis (Method A): 97% $t_r$=21.10 min.

Example 70

1-[4-Methoxybenzoyl-D-cyclopentylglycinyl]-4-(1-methylpiperidin-4-yl)piperazine Dihydrochloride.

Method I-G

To a stirring solution of HOBt (0.388 g, 2.87 mmol) in DMF (2 mL) was added DCC (0.684 g, 2.65 mmol). To this solution was added a solution of p-methoxybenzoic acid (0.404 g, 2.65 mmol) and 1-[D-cyclopentylglycinyl]-4-(1-methylpiperidin-4-yl)piperazine (0.683 g, 2.21 mmol) in DMF (9 mL). After stirring overnight, the solution was filtered; and the filtrate was loaded onto an SCX column (pretreated with 5% acetic acid/methanol and washed with methanol). The column was washed with methanol and then the product was eluted with 1 N ammonia/methanol followed by dichloromethane. The product containing fractions were combined and concentrated in vacuo to give 0.687 g, (70%, 1H NMR; IS-MS, m/e 443.4 (M+1)) of the free base of the title compound.

The HCl salt was prepared using Method I-D to give 737 mg (95%) of the title compound.
1H NMR
IS-MS, m/e 443.4 (M+1)

| Analysis for $C_{25}H_{38}N_4O_3 \cdot 2.1$ HCl $\cdot 2.0$ $H_2O$: | |
|---|---|
| Calcd: | C, 54.08; H, 8.01; N, 10.09; Cl, 13.41; |
| Found: | C, 54.35; H, 7.76; N, 10.06; Cl, 13.64. |

HPLC Analysis (Method A): 99.4% $t_r$=17.84 min.

Example 71

1-[Indole-6-carbonyl-D-cyclopentylglycinyl]-4-(1-methylpiperidin-4-yl)piperazine Dihydrochloride.

Prepared from indole-6-carboxylic acid and 1-[D-cyclopentylglycinyl]-4-(1-methylpiperidin-4-yl)piperazine using procedures substantially equivalent to those used in Method I-G, using HOBt in place of HOAt and EDCI for DCC, and Method I-D.
1H NMR
IS-MS, m/e 452.3 (M+1)

| Analysis for $C_{26}H_{37}N_5O_2 \cdot 1.9$ HCl $\cdot 2.5$ $H_2O$: | |
|---|---|
| Calcd: | C, 55.18; H, 7.82; N, 12.38; Cl, 11.90; |
| Found: | C, 55.46; H, 7.47; N, 12.35; Cl, 11.79. |

HPLC Analysis (Method A): 96.7% $t_r$=17.76 min.

Example 72

1-[4-Methoxybenzoyl-D-cyclohexylglycinyl]-4-(1-methylpiperidin-4-yl)piperazine Dihydrochloride. Prepared from 4-methoxybenzoic acid and 1-[D-cyclohexylglycinyl]-

4-(1-methylpiperidin-4-yl)piperazine using procedures substantially equivalent to those in Method I-G and Method I-D.
1H NMR
IS-MS, m/e 457.4 (M+1)

| Analysis for $C_{26}H_{40}N_4O_3 \cdot 2.0$ HCl $\cdot 0.6$ $H_2O$: | |
|---|---|
| Calcd: | C, 57.79; H, 8.06; N, 10.37; Cl, 13.12; |
| Found: | C, 57.54; H, 8.02; N, 10.19; Cl, 13.22. |

HPLC Analysis (Method A): 100% $t_r$=19.35 min.

Example 73

1-[Indole-6-carbonyl-D-cyclohexylglycinyl]-4-(1-methylpiperidin-4-yl)piperazine Dihydrochloride.

Prepared from indole-6-carboxylic acid and 1-[D-cyclohexylglycinyl]-4-(1-methylpiperidin-4-yl)piperazine using procedures substantially equivalent to those in Method I-G, substituting HOAt for HOBt and EDCI for DCC, and Method I-D.
1H NMR
IS-MS, m/e 466.3 (M+1)

| Analysis for $C_{27}H_{38}N_5O_2 \cdot 2.1$ HCl $\cdot 2.0$ $H_2O$: | |
|---|---|
| Calcd: | C, 56.08; H, 7.86; N, 12.11; Cl, 12.88; |
| Found: | C, 56.29; H, 7.47; N, 12.11; Cl, 12.76. |

HPLC Analysis (Method A): 97.8% $t_r$=20.08 min.

Example 74a

1-[Indole-6-carbonyl-D-phenylglycinyl]-4-(2-phenethyl)piperazine.

Prepared from 1-(D-phenylglycinyl)-4-(2-phenethyl)piperazine and indole-6-carboxylic acid using methods substantially equivalent to those described in Method I-C (62%)
1H NMR (CDCl$_3$).
APCI-MS, m/e=467 (M+1).

Example 74b

1-[Indole-6-carbonyl-D-phenylglycinyl]-4-(2-phenethyl)piperazine Hydrochloride.

Prepared from 1-(indole-6-carbonyl-D-phenylglycinyl)-4-(2-phenethyl)piperazine using methods substantially equivalent to those described in Method I-D (96%).
$[\alpha]^{25}_D$ =−96.8° C. (c 0.25, methanol).
Melting Point=210–215° C. (dec.)
1H NMR (CD$_3$OD).
HPLC Analysis (Method B): 98.6% $t_r$=16.5 min.

| Analysis for $C_{29}H_{30}N_4O_2 \cdot 1.0$ HCl $\cdot 0.5$ $H_2O$: | |
|---|---|
| Calcd: | C, 68.02; H, 6.30; N, 10.94; Cl, 6.92 |
| Found: | C, 68.21; H, 6.32; N, 10.78; Cl, 6.78 |

APCI-MS, m/e=467 (M+1)

Example 75

1-[4-Methoxybenzoyl-D,L-thiazol-2-ylglycinyl]-4-(1-methylpiperidin-4-yl)piperazine.

Prepared from 1-[D,L-(thiazol-2-yl)glycinyl]-4-(1-methylpiperidin-4-yl)piperazine trihydrochloride and anisoyl chloride using method I-B, substituting N,N-diisopropylethylamine for potassium carbonate and substituting dichloromethane for dioxane.
1H-NMR
LCMS m/z 458.4 (M+1)

Example 76a

1-[4-Methoxybenzoyl-D,L-(benzo[b]thiophen-3-yl)glycinyl]-4-(1-methylpiperidin-4-yl)piperazine.

Prepared from 1-[D,L-(benzo[b]thiophen-3-yl)glycinyl]-4-(1-methylpiperidin-4-yl)piperazine trihydrochloride and anisoyl chloride using method G-A, substituting triethylamine for potassium carbonate and substituting dichloromethane for dioxane.
1H-NMR
LCMS m/z 507.4 (M+1)

Example 76b

1-[4-Methoxybenzoyl-D,L-benzothiophene-3-ylglycinyl]-4-(1-methylpiperidin-4-yl)piperazine Dihydrochloride.

Prepared from 1-[4-methoxybenzoyl-D,L-(benzo[b]thiophen-3-yl)glycinyl]-4-(1-methylpiperidin-4-yl)piperazine and 0.2 N HCl, followed by lyophilization.
LCMS m/z 507.4

Example 77a

1-[4-Methoxybenzoyl-D,L-naphthalene-1-ylglycinyl]-4-(1-methylpiperidin-4-yl)piperazine.

Prepared from 1-[D,L-(naphthalen-1-yl)glycinyl]-4-(1-methylpiperidin-4-yl)piperazine trihydrochloride and anisoyl chloride using method G-A, substituting triethylamine for potassium carbonate and substituting dichloromethane for dioxane.
1H-NMR
IS-MS m/e 501.0 (M+1)

Example 77b

1-[4-Methoxybenzoyl-D,L-naphthalene-1-ylglycinyl]-4-(1-methylpiperidin-4-yl)piperazine Dihydrochloride.

Prepared from 1-[D,L-(naphthalen-1-yl)glycinyl]-4-(1-methylpiperidin-4-yl)piperazine and 0.2 N HCl, followed by lyophilization.
1H-NMR
LCMS m/z 501.4 (M+1)

Example 78

1-[Indole-6-carbonyl-D,L-naphthalene-1-ylglycinyl]-4-(1-methylpiperidin-4-yl)piperazine.

Prepared from 1-[D,L-(naphthalen-1-yl)glycinyl]-4-(1-methylpiperidin-4-yl)piperazine trihydrochloride and 6-carboxyindole using method I-C, substitutuing EDCI for DCC and substituting N,N-diisopropylamine for triethylamine.
IS-MS m/e 510.0 (M+1)

Example 79

1-[4-Methoxybenzoyl-D,L-(2-methylsulfonylphenyl)glycinyl]-4-(1-methylpiperidin-4-yl)piperazine Hydrochloride.

Prepared from 1-[D,L-(2-methylsulfonylphenyl)glycinyl]-4-(1-methylpiperidin-4-yl)piperazine and anisoyl chloride using Method I-B, substituting triethylamine for potassium carbonate and substituting dichloromethane for dioxane. The HCl salt was prepared by Method I-D, substituting ethyl acetate for dichloromethane.
1H-NMR
IS-MS, m/e 529-(M+1)

Example 80
1-[4-Methoxybenzoyl-D,L-(thiazol-5-yl)glycinyl]-4-[2-(pyridin-4-yl)ethyl]piperazine Dihydrochloride.

To a stirred solution of 4-methoxybenzoic acid (760 mg, 5.0 mmol), 1-[D,L-(thiazol-5-yl)glycinyl]-4-[2-(pyridin-4-yl)ethyl]piperazine (circa 5.0 mmol) and HOAt (750 mg, 5.5 mmol) in DMF (40 mL) was added EDCI (1.05 g, 5.5 mmol). The mixture was stirred at room temperature for 20 h, and the solvent removed in vacuo. The residues were taken up in chloroform: isopropyl alcohol (2:1) and washed with satd sodium bicarbonate. The aqueous phase was back extracted with chloroform:isopropyl alcohol (2:1) (x3), and the combined organic extracts were dried ($MgSO_4$) and concentrated in vacuo. The crude product was purified by preparative RPHPLC; and the product fractions concentrated, taken up in chloroform:isopropyl alcohol (2:1), washed with satd sodium bicarbonate, dried ($MgSO_4$) and concentrated in vacuo. The free base thus obtained was dissolved in methanol and treated with 2 equivalents of HCl in ether and evaporated to dryness. The residue was dissolved in water/acetonitrile and freeze dried to yield 786 mg of the-title compound.

LCMS M+1 466
NMR

Example 81
1-[4-Methoxybenzoyl-D,L-(2-methylthiazol-4-yl)glycinyl]-4-[2-(pyridin-4-yl)ethyl]piperazine Dihydrochloride.

Prepared from 1-[D,L-(2-methylthiazol-4-yl)glycinyl]-4-[2-(pyridin-4-yl)ethyl]piperazine and 4-methoxybenzoic acid using methods substantially equivalent to those described in Example 80.

LCMS M+1 480
NMR

Example 82
1-[4-Methoxybenzoyl-D,L-(2-aminothiazol-4-yl)glycinyl]-4-[2-(pyridin-4-yl)ethyl]piperazine Dihydrochloride.

Prepared from 1-(Boc-D,L-2-aminothiazol-4-ylglycinyl)-4-[2-(pyridin-4-yl)ethyl]piperazine and 4-methoxybenzoic acid using methods substantially equivalent to those described in Example 80.

LCMS M+1 481
NNR

The following compounds are prepared using similar procedures to those described above and the appropriate starting materials:

1-[Indole-6-carbonyl-D-phenylglycinyl]-4-[2-(2-aminothiazol-4-yl)ethyl]piperazine. (For example by coupling indole-6-carboxylic acid with Intermediate A-10, followed by deprotection of the amino group.)
1-[Indole-6-carbonyl-D-phenylglycinyl]-4-[2-(2-methylpyridin-4-yl)ethyl]piperazine.
1-[Indole-6-carbonyl-D-phenylglycinyl]-4-[2-(2-trifluoromethylpyridin-6-yl)ethyl]piperazine.
1-[Indole-6-carbonyl-D-(2-chlorophenyl)glycinyl]-4-[2-(pyridin-4-yl)ethyl]piperazine.
1-[Indole-6-carbonyl-D-(2-chlorophenyl)glycinyl]-4-[2-(pyridazin-3-yl)ethyl]piperazine.
1-[Indole-6-carbonyl-D-(2-chlorophenyl)glycinyl]-4-[2-(imidazol-1-yl)ethyl]piperazine.
1-[Indole-6-carbonyl-D-(2-chlorophenyl)glycinyl]-4-[2-(imidazol-4-yl)ethyl]piperazine.
1-[Indole-6-carbonyl-D-(2-chlorophenyl)glycinyl]-4-[2-(pyrazol-4-yl)ethyl]piperazine.
1-[4-Methoxybenzoyl-D,L-(quinolin-8-yl)glycinyl]-4-(1-methylpiperidin-4-yl)piperazine.

Assay Protocols
Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay 1

Enzyme assays were carried out at room temperature in 0.1M phosphate buffer, pH 7.4 according to the method of Tapparelli et al (J. Biol. Chem. 1993,268,4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 40Snm in 96 well microplates using a Dynatech $MR^{5000}$ reader (Dynex Ltd, Billingshurst, UK). Km and Ki were calculated using SAS PROC NLIN(SAS Institute, Cary, N.C., USA, Release 6.11) $K_m$ values were determined as 100.9 $\mu$M for factor Xa/pefachrome-FXA and 81.6 $\mu$M for trypsin/pefachrome-TRY. Inhibitor stock solutions were prepared at 40 mM in Me2SO and tested at 500 $\mu$M, 50M and 5 $\mu$M. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 $\mu$M, 21M, 330 nM, 200 nM and 100 nM respectively. NAPAP inhibited thrombin with a Ki value of 3 nM. Compounds of the invention were found to have activity in these assays.

Enzyme Inhibition Assay 2

Human factor Xa and human thrombin were purchased from Enzyme Research Laboratories (South Bend, Ind., USA). Other proteases were from other commercial sources. Chromogenic para-nitroanilide peptide protease substrates were purchased from Midwest Biotech (Fishers, Ind., USA).

The binding affinities for human factor Xa were measured as apparent association constants (Kass) derived from protease inhibition kinetics as described previously.[a,b,c,d] The apparent Kass values were obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol was: 50 $\mu$l buffer (0.06 M tris, 0.3 M NaCl, pH 7.4); 25 $\mu$l inhibitor test solution (in MeOH); 25 $\mu$l human factor Xa (32 nM in 0.03 M tris, 0.15 M NaCl, 1 g/ml HSA); finally, 150 $\mu$l BzIleGluGlyArgpNA (0.3 mM in water) dded within 2 min to start hydrolysis. Final factor Xa was 3.2 nM. Free [Xa] and bound [Xa] were determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=$[E:T]/[E_f][I_f]=[E_b]/[E_f][I^\circ-I_b]$ The apparent Kass values so obtained are approximately the inverse of the Ki for the respective inhibitors [1/appKass =app Ki]. The variability of mean apparent Kass values determined at the single substrate concentration was +/−15%. The assay system Km was measured as 0.347+/− 0.031 mM [n=4]; and Vmax was 13.11+/−0.76 $\mu$M/min.

Kass values were determined with thrombin and other proteases using the same protocol with the following enzyme and substrate concentrations: thrombin 5.9 nM with 0.2 mM BzPheValArgpNA; XIa 1.2 nM with 0.4 mM pyroGluProArgpNA; XIIa 10 nM with 0.2 mM HDProPheArgpNA; plasmin 3.4 nM with 0.5 mM HDValLeuLyspNA; nt-PA 1.2 nM with 0.8 mM HDIleProArgpNA; and urokinase 0.4 nM with 0.4 mM pyroGluGlyArgpNA; aPC 3 nM with 0.174 mM pyroGluProArgpNA; plasma kallikrein 1.9 nM with D ProPheArgpNA; bovine trypsin 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H—S Lin, J R McCowan, A D Palkowitz, G F Smith, M E Richett, K Takeuchi, K J Thrasher, J M Tinsley, B G Utterback, S—C B Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, J A Bastian, N Y Chirgadze, M L Denny, M J Fisher, D S Gifford-Moore, R W Harper, V J Klimkowski, T J Kohn, H S Lin, J R McCowan, M E Richett, G F Smith, K Takeuchi, J E Toth, M Zhang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. In press, J Med Chem (1999).

In general, the compounds of formula (I) exemplified herein have been found to exhibit a Ki of 10 $\mu$M or less in Assay 1 and/or a Kass of at least $0.1 \times 10^6$ L/mole in Assay 2.

The ability of a test compound to elongate Partial Thromboplastin Time (Prothrombin Time) may be evaluated in the following test protocols.

Partial Thromboplastin Time (Prothrombin) Test Protocol

Venous blood was collected into 3.2% (0.109 m) trisodium citrate vacutainer tubes at 1 volume of anticoagulant to nine volumes of blood. The blood cells were separated by centrifugation at 700 g for ten minutes to yield plasma, which was frozen at 70° C. until required.

To perform the test, 100 $\mu$l of plasma was pipetted into in a glass test tube, 1 $\mu$l of test compound in DMSO was added, and allowed to warm to 37° over two minutes. 100 $\mu$l of warm (37°) Manchester (tissue thromboplasin) reagent (Helena Biosciences, UK) was added, allowed to equilibrate for two minutes. 100 $\mu$l of warm (370) 25 mM calcium chloride solution was added to initiate clotting. The test tube was tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention were found to significantly elongate the partial thromboplastin time (Prothrombin time).

Alternative Prothrombin Time and APTT Protocols

Coagulation Determinations. Prothrombin Times and APTT values were determined in HUMAN PLASMA with a STA instrument (Stago). BioPT is a special non-plasma clotting assay triggered with human tissue factor (Innovin). Possible binding to albumen or to lipid was assessed by comparing the BioPT effects in the presence/absence of 30 mg/ml human albumen (HSA) and 1 mg/ml phosphatidyl choline (PC). Inhibitors were delivered in 50% MeOH vehicle.

APTT Assay

75 $\mu$l plasma Citrol Baxter-Dade Citrated Normal Human Plasma

25 $\mu$l test sol'n

75 $\mu$l Actin Baxter-Dade Activated Cephaloplastin incubate 2 min min. @ 37°

75 $\mu$l CaCl$_2$ (0.02 M)

PT Assay

75 $\mu$l plasma

25 $\mu$l test sol'n

75 $\mu$l saline incubate 1 min. @ 37° C.

75 $\mu$l Innovin Baxter-Dade Recombinant Human Tissue Factor

Compounds of the invention were found to be potent inhibitors of factor Xa.

What is claimed is:

1. 1-(Indole-6-carbonyl-D-phenylglycinyl)-4-(1-methylpiperidin-4-yl) piperazine; or a physiologically-tolerable salt thereof.

2. A pharmaceutical composition, which comprises a compound as claimed in claim 1 together with at least one pharmaceutically acceptable carrier or excipient.

3. A method of treatment of a human or non-human animal body to combat a thrombotic disorder selected from venous thrombosis, pulmonary embolism, arterial thrombosis, myocardial ischaemia, myocardial infarction and cerebral thrombosis, which comprises administering to said body an effective amount of a compound as claimed in claim 1.

4. A method as claimed in claim 3, in which said body is a human body.

* * * * *